United States Patent
Lawrence et al.

(10) Patent No.: US 9,221,808 B2
(45) Date of Patent: Dec. 29, 2015

(54) PYRIDYLTHIAZOLE-BASED UREAS AS INHIBITORS OF RHO ASSOCIATED PROTEIN KINASE (ROCK) AND METHODS OF USE

(75) Inventors: Nicholas J. Lawrence, Tampa, FL (US); Roberta Pireddu, Tampa, FL (US); Said M. Sebti, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 211 days.

(21) Appl. No.: 13/640,385

(22) PCT Filed: Apr. 18, 2011

(86) PCT No.: PCT/US2011/032893
§ 371 (c)(1),
(2), (4) Date: Oct. 10, 2012

(87) PCT Pub. No.: WO2011/130740
PCT Pub. Date: Oct. 20, 2011

(65) Prior Publication Data
US 2013/0059839 A1    Mar. 7, 2013

Related U.S. Application Data

(60) Provisional application No. 61/325,158, filed on Apr. 16, 2010.

(51) Int. Cl.
*C07D 417/04* (2006.01)
*C07D 417/14* (2006.01)

(52) U.S. Cl.
CPC ............ *C07D 417/04* (2013.01); *C07D 417/14* (2013.01)

(58) Field of Classification Search
CPC .................................................... C07D 417/04
USPC ..................................................... 546/270.4
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,167,649 A | 12/1992 | Zook | |
| 6,410,533 B1 | 6/2002 | Hirth et al. | |
| 6,960,648 B2 | 11/2005 | Bonny | |
| 2002/0035243 A1 | 3/2002 | Imfeld et al. | |
| 2002/0120100 A1 | 8/2002 | Bonny | |
| 2002/0173507 A1* | 11/2002 | Santora et al. | 514/227.5 |
| 2003/0032594 A1 | 2/2003 | Bonny | |

FOREIGN PATENT DOCUMENTS

| | | |
|---|---|---|
| WO | WO2004/041813 | 5/2004 |
| WO | WO2004/064730 | 8/2004 |
| WO | WO2007/026920 | 3/2007 |
| WO | WO2007/060028 | 5/2007 |
| WO | WO2007/133622 | 11/2007 |
| WO | WO2009/027392 | 3/2009 |
| WO | WO2009/114552 | 9/2009 |
| WO | WO2010/036316 | 4/2010 |

OTHER PUBLICATIONS

Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Austin et al., Policy forum: Molecular Biology: NIH molecular libraries initiative, Science, 306:1138-1139 (2004).
Chang et al., Activation of Rho-associated coiled-coil protein kinase 1 (ROCK-I) by caspase-3 cleavage plays an essential role in cardiac myocyte apoptosis, Proc. Nat'l Acad. Sci. USA, 103:14495-14500 (2006).
Chen et al., Chroman-3-amides as potent Rho kinase inhibitors, Bioorg. Med. Chem. Lett., 18:6406-6409 (2008).
Coleman et al., Membrane blebbing during apoptosis results from caspase-mediated activation of ROCK I, Nat. Cell Biol., 3:339-345 (2001).
Dong et al., Current status of Rho-associated kinases (ROCKs) in coronary atherosclerosis and vasospasm, Cardiovasc. Hematol. Agents Med. Chem., 7:322-330 (2009).
Feng et al., Discovery of Substituted 4-(Pyrazol-4-yl)-phenylbenzodioxane-2-carboxamides as Potent and Highly Selective Rho Kinase (ROCK-II) Inhibitors, J Med. Chem., 51:6642-6645 (2008).
Goodman et al., Development of Dihydropyridone Indazole Amides as Selective Rho-Kinase Inhibitors, J. Med. Chem., 50:6-9 (2007).
Hampson et al., Analogues of Y27632 increase gap junction communication and suppress the formation of transformed NIH3T3 colonies, Br. J. Cancer, 101:829-839 (2009).
Huryn et al., The molecular libraries screening center network (MLSCN): identifying chemical probes of biological systems, Annu. Rep. Med. Chem., 42:401-416 (2007).
Igishi et al., Enhancement of cisplatin-induced cytotoxicity by ROCK inhibitor through suppression of focal adhesion kinaseindependent mechanism in lung carcinoma cells, Int. J. Oncol., 23:1079-1085 (2003).
Imamura et al., Y-27632, an inhibitor of rho-associated protein kinase, suppresses tumor cell invasion via regulation of focal adhesion and focal adhesion kinase, Jpn. J. Cancer Res., 91:811-816 (2000).
International Search Report and Written Opinion for Application No. PCT/US2013/022965 dated May 9, 2013.

(Continued)

*Primary Examiner* — Patricia L Morris
(74) *Attorney, Agent, or Firm* — Meunier Carlin & Curfman LLC

(57) ABSTRACT

Compounds and compositions having activity as inhibitors of Rho-associated proteinkinases (ROCKs), and methods of making and using the subject compounds are disclosed.

12 Claims, 6 Drawing Sheets

(56) References Cited

OTHER PUBLICATIONS

International Search Report and Written Opinion for Application No. PCT/US2011/032893 dated Dec. 26, 2011.
Ishizaki et al., Pharmacological properties of Y-27632, a specific inhibitor of Rho-associated kinases, Mol. Pharmacal., 57:976-983 (2000).
Itoh et al., An essential part for Rho-associated kinase in the transcellular invasion of tumor cells, Nat. Med, 5(2):221-225 (1999).
Iwakubo et al., Design and synthesis of rho kinase inhibitors (III), Bioorg. Med. Chem., 15:1022-1033 (2007).
Jacobs et al., The structure of ROCK1 reveals the mechanism for ligand selectivity, J. Biol. Chem. 281(1):260-268 (2006).
Kamai et al., Overexpression of RhoA, Rac1, and Cdc42 GTPases is associated with progression in testicular cancer, Clinical Cancer Research, 10:4799-4805 (2004).
Kang et al., Identification of small molecules that inhibit GSK-3β through virtual screening, Bioorg. Med. Chem. Lett., 19:533-537 (2009).
Koresawa et al., High-throughput screening with quantitation of ATP consumption: A universal non-radioisotope, homogeneous assay for protein kinase, Assay Drug Dev. Technol., 2(2):153-160 (2004).
Kubo et al., The therapeutic effects of Rho-ROCK inhibitors on CNS disorders, Ther. Clin. Risk Manage., 4:605-615 (2008).
Kubo et al., Rho-ROCK inhibitors for the treatment of CNS injury, Recent Pat. CNS Drug Discov., 2:173-179 (2007).
Liao et al., Rho kinase (ROCK) inhibitors, J. Cardiovasc. Pharmacol., 50(1):17-24 (2007).
Liu et al., Inhibition of Rho-Associated Kinase Signaling Prevents Breast Cancer Metastasis to Human Bone, Cancer Res., 69:8742-8751 (2009).
LoGrasso et al., Rho kinase (ROCK) inhibitors and their application to inflammatory disorders, Curr. Top Med. Chem., 9(8):704-723 (2009).
Nakagawa et al., ROCK-I and ROCK-II, two isoforms of Rho-associated coiled-coil forming protein serine/threonine kinase in mice, FEBS Lett., 392:189-193 (1996).
Nakajima et al., Effect of Wf-536, a novel ROCK inhibitor, against metastasis of B16 melanoma, Cancer Chemother Pharmacal., 52:319-324 (2003).
Nakajima et al., Wf-536 prevents tumor metastasis by inhibiting both tumor motility and angiogenic actions, Eur. J. Pharmacal., 459(2-3):113-120 (2003).
Narumiya et al., Use and properties of ROCK-specific inhibitor Y-27632, Methods Enzymal, 325:273-284 (2000).
Ogata et al., Fasudil inhibits lysophosphatidic acid-induced invasiveness of human ovarian cancer cells, Int. J. Gynecol. Cancer, 19(9):1473-1480 (2009).
Rikitake et al., Decreased Perivascular Fibrosis but Not Cardiac Hypertrophy in ROCK 1$^{+/-}$ Haploinsufficient Mice, Circulation, 112:2959-2965 (2005).
Sapet et al., Thrombin-induced endothelial microparticle generation: Identification of a novel pathway involving ROCK-II activation by caspase-2, Blood, 108:1868-1876 (2006).
Schmitz et al., Rho GTPases: Signaling, Migration, and Invasion, Exp. Cell Res., 261(1):1-12 (2000).
Sebbagh et al., Direct cleavage of ROCK II by granzyme B induces target cell membrane blebbing in a caspase-independent manner, J. Exp. Med., 201:465-471 (2005).
Sebbagh et al., Caspase-3-mediated cleavage of ROCK I induces MLC phosphorylation and apoptotic membrane blebbing, Nat. Cell Biol., 3(4):346-352 (2001).
Sehon et al., Potent, Selective and Orally Bioavailable Dihydropyrimidine Inhibitors of Rho Kinase (ROCK1) as Potential Therapeutic Agents for Cardiovascular Diseases, J. Med. Chem., 51(21):6631-6634 (2008).
Sessions et al., Benzimidazole and benzoxazole-based inhibitors of Rho kinase, Bioorg. Med. Chem. Lett., 18(24):6390-6393 (2008).
Shimizu et al., ROCK-I regulates closure of the eyelids and ventral body wall by inducing assembly of actomyosin bundles, J. Cell Biol., 168:941-953 (2005).
Shimokawa et al., Development of Rho-kinase inhibitors for cardiovascular medicine, Trends Pharmacol. Sci., 28:296-302 (2007).
Shimokawa et al., Rho-kinase is an important therapeutic target in cardiovascular medicine, Arterioscler. Thromb. Vasc. Biol, 25:1767-1775 (2005).
Somlyo et al., Rho kinase and matrix metalloproteinase inhibitors cooperate to inhibit angiogenesis and growth of human prostate cancer xenotransplants, FASEB J., 17:223-234 (2003).
Somlyo et al., Rho-kinase inhibitor retards migration and in vivo dissemination of human prostate cancer cells, Biochem. Biophys. Res. Commun., 269(3):652-659 (2000).
Suwa et al., Overexpression of the rhoC gene correlates with progression of ductal adenocarcinoma of the pancreas, Br. J. Cancer, 77(1):147-152 (1998).
Takami et al., Design and synthesis of Rho kinase inhibitors (I), Bioorg. Med. Chem., 12:2115-2137 (2004).
Thomas et al., The pilot phase of the NIH chemical genomics center, Curr. Top. Med. Chem., 9(13):1181-1193 (2009).
Thumkeo et al., Targeted disruption of the mouse Rho-associated Kinase 2 gene results in intrauterine growth retardation and fetal death, Mol. Cell Biol., 23(14):5043-5055 (2003).
Toyoizumi et al., Combined therapy with chemotherapeutic agents and herpes simplex virus type 1 ICP34.5 mutant (HSV-1716) in human non-small cell lung cancer, Human Gene Therapy, 10(18):3013-3029 (1999).
Uchida et al., The suppression of small GTPase Rho signal transduction pathway inhibits angiogenesis in vitro and in vivo, Biochem. Biophys. Res. Commun., 269(2):633-640 (2000).
Uehata et al., Calcium sensitization of smooth muscle mediated by a Rho-associated protein kinase in hypertension, Nature, 389:990-994 (1997).
Xing et al., Rho-kinase as a potential therapeutic target for the treatment of pulmonary hypertension, Drug News Perspect., 19(9):517-522 (2006).
Yin et al., Discovery of potent and selective urea-based ROCK inhibitors and their effects on intraocular pressure in rats, ACS Med. Chem. Lett., 1:175-179 (2010).
Ying et al., The Rho kinase inhibitor fasudil inhibits tumor progression in human and rat tumor models, Mol. Cancer Ther., 5:2158-2164 (2006).
Yoshimi et al., Antinociceptive effects of AS1892802, a novel Rho kinase inhibitor, in rat models of inflammatory and noninflammatory arthritis, J. Pharma. Exp. Thera., 334(3):955-963 (2010).
Zhang et al., Targeted deletion of ROCK1 protects the heart against pressure overload by inhibiting reactive fibrosis, FASEB J., 20:916-925 (2006).
Zohrabian et al., Rho/ROCK and MAPK signaling pathways are involved in glioblastoma cell migration and proliferation, Anticancer Res., 29:119-123 (2009).

\* cited by examiner

PYRIDYLTHIAZOLE-BASED UREAS AS INHIBITORS OF RHO ASSOCIATED PROTEIN KINASE (ROCK) AND METHODS OF USE

CROSS REFERENCE TO RELATED APPLICATIONS

This application claims the benefit of priority to U.S. Provisional Application 61/325,158, filed Apr. 16, 2010, which is incorporated by reference herein in its entirety.

ACKNOWLEDGMENT OF GOVERNMENT SUPPORT

This invention was made with government support under grant number CA067771, awarded by the National Institutes of Health. The U.S. Government has certain rights in the invention.

BACKGROUND

Rho associated protein kinases (ROCKs) are Ser/Thr protein kinases, activated by small GTPases of the Rho family that act as molecular switches to mediate cell signaling. The Rho/ROCK signaling pathway is known to participate in the regulation of numerous cellular functions such as actin cytoskeleton organization, contraction, cell adhesion, motility, and morphology, proliferation, cytokinesis, gene expression, and angiogenesis.

Two isoforms, ROCK1 and ROCK2, have been identified and they share 65% homology in amino acid sequence and 92% homology in their kinase domains. The two isoforms, although ubiquitously expressed, have been found to possess differential tissue distribution. ROCK1 is expressed in lung, liver, stomach, spleen, kidney and testis, whereas ROCK2 is highly expressed in brain, heart and muscle tissues (Nakagawa, et al., "ROCK-I and ROCK-II, two isoforms of Rho-associated coiled-coil forming protein serine/threonine kinase in mice," *FEBS Lett,* 1996, 392:189-193). Despite the differential tissue distribution, little is known about the functional differences between the two ROCK isoforms (Sapet, et al., "Thrombin-induced endothelial microparticle generation: identification of a novel pathway involving ROCK-II activation by caspase-2," *Blood,* 2006, 108:1868-1876; Chang, et al., "Activation of Rho-associated coiled-coil protein kinase 1 (ROCK-1) by caspase-3 cleavage plays an essential role in cardiac myocyte apoptosis," *Proc Natl Acad Sci USA,* 2006, 103:14495-14500; Sebbagh, et al., "Caspase-3-mediated cleavage of ROCK I induces MLC phosphorylation and apoptotic membrane blebbing," *Nat Cell Biol,* 2001, 3:346-352; Thumkeo, et al., "Targeted disruption of the mouse rho-associated kinase 2 gene results in intrauterine growth retardation and fetal death," *Mol Cell Biol,* 2003, 23:5043-55; Shimizu, et al., "ROCK-I regulates closure of the eyelids and ventral body wall by inducing assembly of actomyosin bundles," *J Cell Biol,* 2005, 168:941-53; Zhang, et al., "Targeted deletion of ROCK1 protects the heart against pressure overload by inhibiting reactive fibrosis," *Faseb J,* 2006, 20:916-925; Rikitake, et al., "Decreased Perivascular Fibrosis but Not Cardiac Hypertrophy in ROCK1+/−Haploinsufficient Mice," *Circulation,* 2005, 112:2959-2965; Coleman, et al., "Membrane blebbing during apoptosis results from caspase-mediated activation of ROCK I," *Nat Cell Biol,* 2001, 3:339-45; Sebbagh, et al., "Direct cleavage of ROCK II by granzyme B induces target cell membrane blebbing in a caspase-independent manner," *J Exp Med,* 2005, 201:465-471).

ROCKs have been subjected to growing attention, having been implicated in a range of therapeutic areas including cardiovascular diseases (Shimokawa, et al., "Development of Rho-kinase inhibitors for cardiovascular medicine," *Trends Pharmacol Sci,* 2007, 28:296-302; Xing, et al., "Rho-kinase as a potential therapeutic target for the treatment of pulmonary hypertension," *Drug News Perspect,* 2006, 19:517-522; Liao, et al., "Rho kinase (ROCK) inhibitors," *J Cardiovasc Pharmacol,* 2007, 50:17-24; Shimokawa, et al., "Rho-kinase is an important therapeutic target in cardiovascular medicine," *Arterioscler Thromb Vasc Biol,* 2005, 25:1767-1775; Dong, et al., "Current status of Rho-associated kinases (ROCKs) in coronary atherosclerosis and vasospasm," *Cardiovasc Hematol Agents Med Chem,* 2009, 7:322-330), CNS disorders (Kubo, et al., "Rho-ROCK inhibitors for the treatment of CNS injury," *Recent Pat CNS Drug Discov,* 2007, 2:173-9; Kubo, et al., "The therapeutic effects of Rho-ROCK inhibitors on CNS disorders," *Ther Clin Risk Manage,* 2008, 4:605-615), inflammation (LoGrasso Philip, et al., "Rho kinase (ROCK) inhibitors and their application to inflammatory disorders," *Curr Top Med Chem,* 2009, 9:704-23), and cancer (Suwa, et al., "Overexpression of the rhoC gene correlates with progression of ductal adenocarcinoma of the pancreas," *Br J Cancer,* 1998, 77:147-152; Kamai, et al., "Overexpression of RhoA, Rac1, and Cdc42 GTPases is associated with progression in testicular cancer," *Clinical Cancer Research,* 2004, 10:4799-4805; Schmitz, et al., "Rho GTPases: Signaling, Migration, and Invasion," *Exp Cell Res,* 2000, 261:1-12; Imamura, et al., "Y-27632, an inhibitor of rho-associated protein kinase, suppresses tumor cell invasion via regulation of focal adhesion and focal adhesion kinase, "*Jpn J Cancer Res,* 2000, 91:811-816; Somlyo, et al., "Rho-kinase inhibitor retards migration and in vivo dissemination of human prostate cancer cells," *Biochem Biophys Res Commun,* 2000, 269:652-659; Uchida, et al., "The suppression of small GTPase Rho signal transduction pathway inhibits angiogenesis in vitro and in vivo," *Biochem Biophys Res Commun,* 2000, 269:633-640; Itoh, et al., "An essential part for Rho-associated kinase in the transcellular invasion of tumor cells," *Nat Med (NY),* 1999, 5:221-225; Uehata, et al., "Calcium sensitization of smooth muscle mediated by a Rho-associated protein kinase in hypertension," *Nature,* 1997, 389:990-4; Ishizaki, et al., "Pharmacological properties of Y-27632, a specific inhibitor of Rho-associated kinases," *Mol Pharmacol,* 2000, 57:976-983; Narumiya, et al., "Use and properties of ROCK-specific inhibitor Y-27632," *Methods Enzymol,* 2000, 325:273-84; Nakajima, et al., "Effect of Wf-536, a novel ROCK inhibitor, against metastasis of B16 melanoma," *Cancer Chemother Pharmacol,* 2003a, 52:319-24; Nakajima, et al., "Wf-536 prevents tumor metastasis by inhibiting both tumor motility and angiogenic actions," *Eur J Pharmacol,* 2003b, 459:113-20; Ying, et al., "The Rho kinase inhibitor fasudil inhibits tumor progression in human and rat tumor models," *Mol Cancer Ther,* 2006, 5:2158-2164; Somlyo, et al., "Rho kinase and matrix metalloproteinase inhibitors cooperate to inhibit angiogenesis and growth of human prostate cancer xenotransplants," *Faseb J,* 2003, 17:223-234; Hampson, et al., "Analogues of Y27632 increase gap junction communication and suppress the formation of transformed NIH3T3 colonies," *Br J Cancer,* 2009, 101:829-839; Igishi, et al., "Enhancement of cisplatin-induced cytotoxicity by ROCK inhibitor through suppression of focal adhesion kinase-independent mechanism in lung carcinoma cells," *Int J Oncol,* 2003, 23:1079-1085; Liu, et al., "Inhibition of Rho- Associated Kinase Signaling Prevents Breast Cancer Metastasis to Human Bone," *Cancer Res,* 2009, 69:8742-8751; Ogata, et al., "Fasudil inhibits lysophosphatidic acid-induced invasiveness of human ovarian cancer cells," *Int J Gynecol Cancer,* 2009, 19:1473-80; Zohrabian, et al., "Rho/ROCK and MAPK signaling pathways are involved in glioblastoma cell migration and proliferation," *Anticancer Res,* 2009, 29:119-123).

Co-overexpression of Rho and ROCK proteins in cancer cells has been reported in ovarian cancer, pancreatic, testicular, and bladder cancer (Suwa et al. (1998); Kamai et al. (2004)). Malignant transformation and metastasis require changes in the migratory, invasive and adhesive properties of tumor cells, and changes in the regulation cellular processes depending on the proper assembly/disassembly of actin-cytoskeleton. Each of these events is regulated by Rho/ROCK pathway and plays an important role in the development and progression of cancer (Schmitz et al. (2000)). The implication of Rho/ROCK signalling pathway in invasion by tumor cells (Imamura et al. (2000); Somlyo et al. (2000)), angiogenesis (Uchida et al. (2000)), and their evolution to metastasis (Itoh et al. (1999)) has been amply documented. In light of these findings, the pharmacological inhibition of ROCKs has been suggested as a promising strategy in the prevention of cell invasion, a central event in the process of metastasis (Itoh et al. (1999); Uehata et al. (1997); Ishizaki et al. (2000); Narumiya et al. (2000)).

The potential of ROCK inhibitors as anticancer drugs was demonstrated by the identification of specific ATP competitive inhibitors, Y27632, and Wf536 (FIG. 1) (Itoh et al. (1999); Nakajima et al. (2003a); Nakajima et al. (2003b); Somlyo et al. (2000)), displaying high inhibitory potency for ROCKs. Specifically, Y27632 was reported to reduce metastasis in animal model systems (Itoh et al. (1999)), while Wf-536 has shown efficacy in preventing tumor metastasis in vivo models by inhibiting tumor-induced angiogenesis as well as tumor motility (Nakajima et al. (2003a); Nakajima et al. (2003b); Somlyo et al. (2003)). Han and coworkers have also investigated the ability of Fasudil (5-(1,4-diazepane-1-sulfonyl)isoquinoline) (the only ROCK inhibitor clinically approved in Japan for the treatment of cerebral vasospasm) to inhibit tumor progression in human and rat tumor models (Ying et al. (2006)).

Significant research efforts have been directed towards the identification of more potent and more selective ROCK inhibitors and their use for the treatment of cardiocascular diseases and CNS disorders (Chen, et al., "Chroman-3-amides as potent Rho kinase inhibitors," *Bioorg Med Chem Lett,* 2008, 18:6406-6409; Sessions, et al., "Benzimidazole- and benzoxazole-based inhibitors of Rho kinase," *Bioorg Med Chem Lett,* 2008, 18:6390-6393; Iwakubo, et al., "Design and synthesis of rho kinase inhibitors (III)," *Bioorg Med Chem,* 2007, 15:1022-1033; Goodman, et al., "Development of Dihydropyridone Indazole Amides as Selective Rho-Kinase Inhibitors," *J Med Chem,* 2007, 50:6-9; Feng, et al., "Discovery of Substituted 4-(Pyrazol-4-yl)-phenylbenzo-dioxane-2-carboxamides as Potent and Highly Selective Rho Kinase (ROCK-II) Inhibitors," *J Med Chem,* 2008, 51:6642-6645; Sehon, et al., "Potent, Selective and Orally Bioavailable Dihydropyrimidine Inhibitors of Rho Kinase (ROCK1) as Potential Therapeutic Agents for Cardiovascular Diseases," *J Med Chem,* 2008, 51:6631-6634). The antitumor properties of these inhibitors have yet to be shown or published.

The aminothiazole derivative CID5056270 (FIG. 2) has been reported to potently inhibit ROCK2 enzymatic activity with an $IC_{50}$ values<3 nM (Molecular Libraries Screening Centers Network (MLSCN) (Thomas, et al., "The pilot phase of the NIH chemical genomics center," *Curr Top Med Chem (Sharjah, United Arab Emirates),* 2009, 9:1181-1193; Austin, et al., "Policy forum: Molecular biology: NIH molecular libraries initiative," *Science,* 2004, 306:1138-1139; Huryn, et al., "The molecular libraries screening center network (MLSCN): identifying chemical probes of biological systems," *Annu Rep Med Chem,* 2007, 42:401-416), assay ID 644). CID5056270 displayed a high potency in FRET-based Z'-Lyte biological assay (FIG. 3) (Kang, et al., "Identification of small molecules that inhibit GSK-3b through virtual screening," *Bioorg Med Chem Lett,* 2009, 19:533-537; Koresawa, et al., "High-throughput screening with quantitation of ATP consumption: A universal non-radioisotope, homogeneous assay for protein kinase," *Assay Drug Dev Technol,* 2004, 2:153-160) (ROCK2 $IC_{50}$ 40 nM) (FIG. 2) and also inhibited ROCK1 with an $IC_{50}$ of 76 nM (FIG. 2). In light of its potency and preliminary kinase-selectivity profile (Aurora-A $IC_{50}$ values>100000 nM) (FIG. 2), CID5056270 was chosen as a starting point for the design of a focused library of aminothiazole-based small molecules as ROCK1 inhibitors. Chemical modifications of CID5056270 to improve potency, selectivity, and determine the structural features responsible for the activity, led to the identification of the urea analog 1aa (ROCK1 $IC_{50}$ 170 nM, ROCK2 $IC_{50}$ 50 nM, FIG. 2) as a novel and potent inhibitor of ROCK1.

SUMMARY

In accordance with the purposes of the disclosed materials, compounds, compositions, articles, devices, and methods, as embodied and broadly described herein, the disclosed subject matter relates to compositions and methods of making and using the compositions. In other aspect, the disclosed subject matter relates to compounds having activity as inhibitors of Rho-associated proteinkinases (ROCKs), methods of making and using the compounds, and compositions comprising the compounds. In certain aspects, the disclosed subject matter relates to compounds having the chemical structure shown in Formula I.

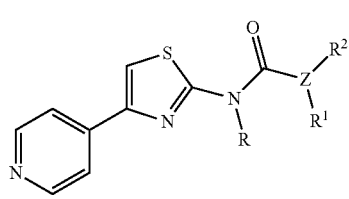

wherein
Z is CR or N;
R is H, alkyl, acetyl, or heteroalkyl;
$R^1$ is H, alkyl, acetyl, or heteroalkyl;
$R^2$ is H, alkyl, cycloalkyl, heterocycloalkyl, or aryl, any of which can be optionally substituted with one or more of —OH, —C(O)NH$_2$, acetyl, carbonyl, alkyl, cycloalkyl, heterocycloalkyl, aryl, or heteroaryl, any of which can be optionally substituted with one or more of —OH, —NO$_2$, —NH$_2$, —NR$^6$R$^7$, alkyl, alkoxy, alkylalkoxy, alkoxylalkoxy, halogenated alkoxy, heteroarylcarbonyl, heteroaryl, —OCX$_3$, —OCHX$_2$, —OCH$_2$X, —OSO$_2$CH$_3$, tosyl, or halogen;
$R^6$ and $R^7$ are, independently, H, alkyl, —SO$_2$CH$_3$, —C(O)CH$_3$, or —C(O)NH$_2$;
X is independently H or halogen;
or a pharmaceutically acceptable salt or hydrate thereof.

In still further aspects, the disclosed subject matter relates to methods for treating oncological disorders in a patient. For example, disclosed herein are methods whereby an effective amount of a compound or composition disclosed herein is administered to a patient having an oncological disorder and who is in need of treatment thereof. Similarly, the disclosed subject matter relates to methods of treating cardiovascular disorders.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
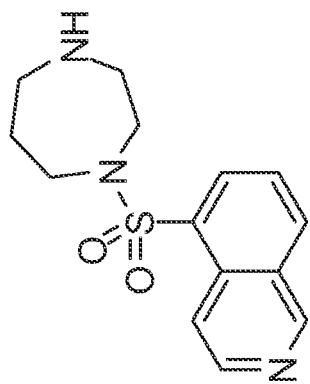
FIG. 1 shows known Rho kinase inhibitors.
Figure 1:
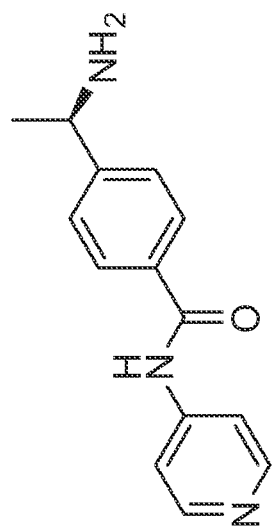
Figure 1:
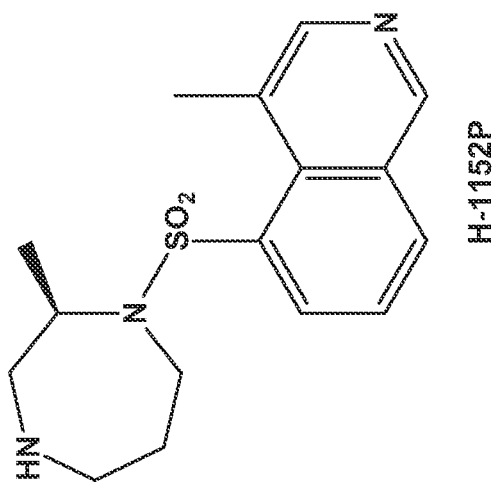
Figure 1:
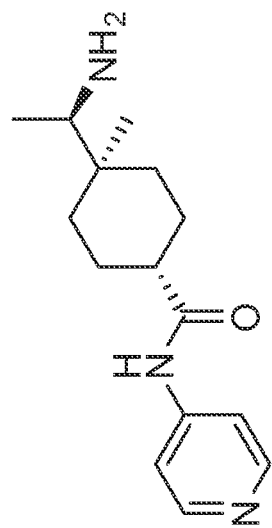
Figure 2:
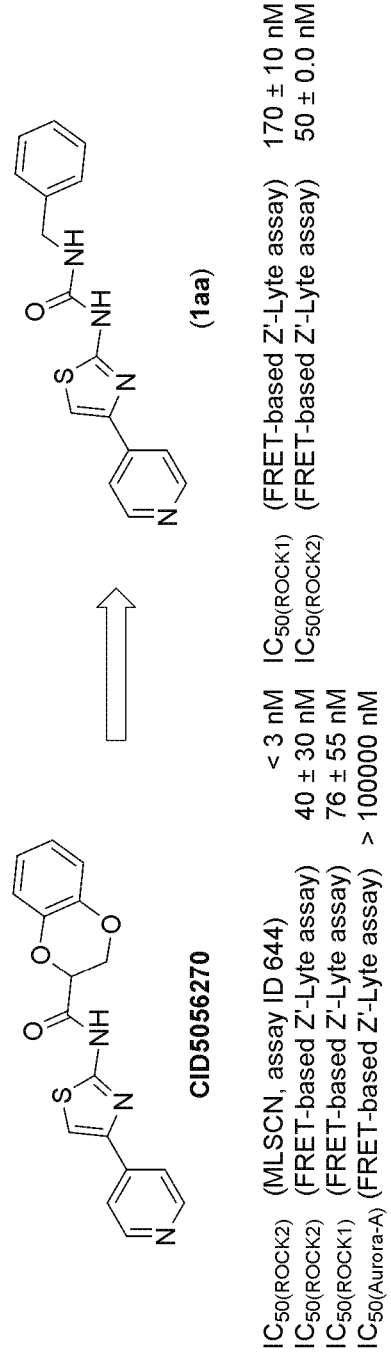
FIG. 2 shows the structure of CDI5056270 and compound 1aa.
Figure 3:
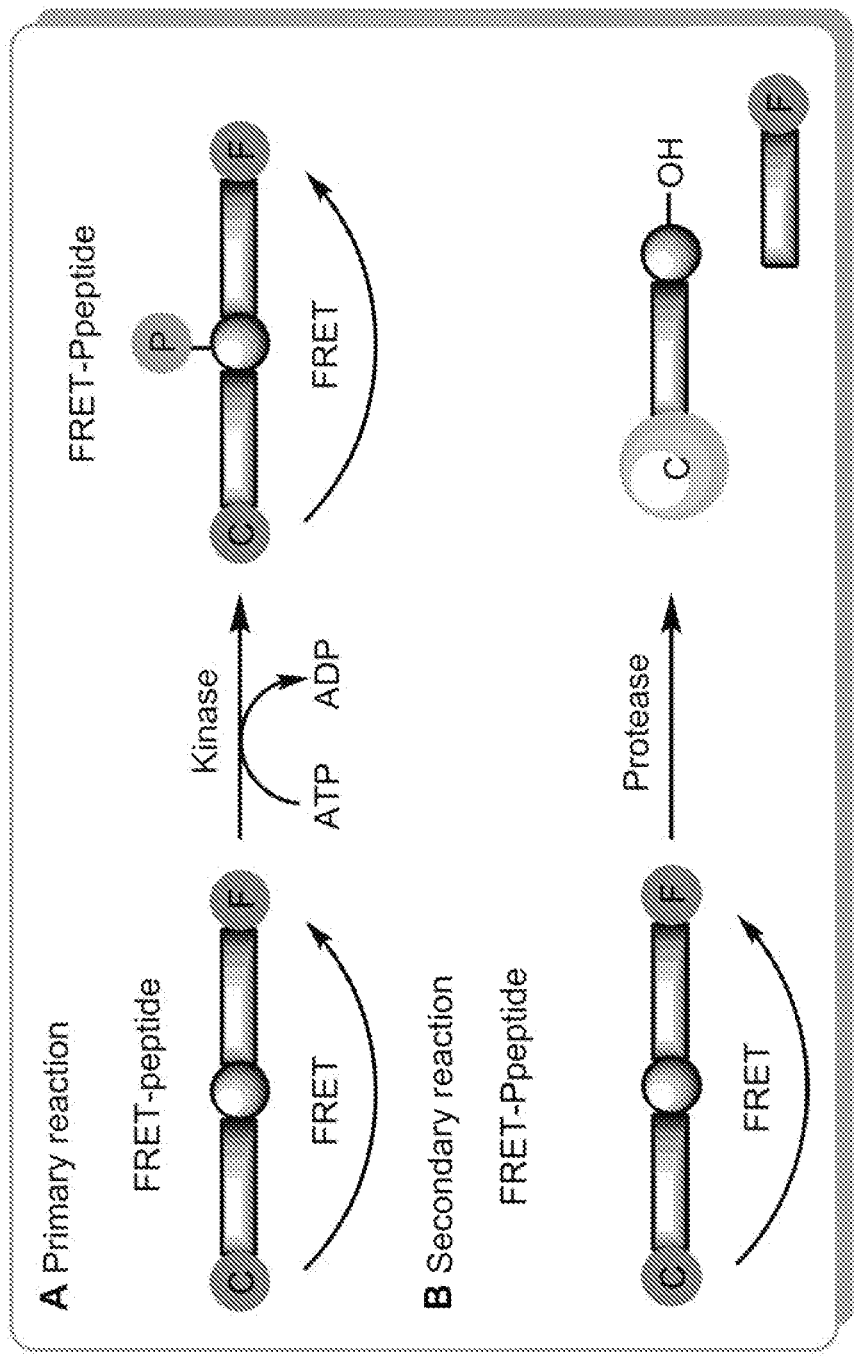
FIG. 3 shows a FRET-based Z'-Lyte assay. A) In the primary reaction, the Rho kinases phosphorylates a single serine or threonine residue in a synthetic FRET-peptide. This FRET-peptide is doubly labeled with a fluorophore at each end—coumarin (the FRET donor) on one end and fluorescein (the FRET acceptor) on the other—and also contains a single phosphorylation site which either overlaps with or lies adjacent to the proteolytic site. B) In the secondary reaction, a site-specific protease recognizes and cleaves the non-phosphorylated FRET-peptide. Cleavage disrupts FRET between the donor and acceptor fluorophores on the FRET-peptide, whereas uncleaved, phosphorylated FRET-peptides maintain FRET. Kinases phosphorylated FRET-peptides cannot be cleaved by the protease. Upon excitation of the donor fluorophore (coumarin) due to FRET, the uncleaved FRET-peptide yields a coumarin fluorescence signal (at 445 nm) and a fluorescein fluorescence signal (at 520 nm). Cleavage disrupts FRET and causes a decrease in the fluorescein fluorescence signal and a strong increase in the coumarin fluorescence signal. Therefore the extension of the phosphprylation can be measured by FRET-signal remaining the protease reaction. The assay uses a ratiometric method, which calculates the ratio of donor emission to acceptor emission (the emission ratio) after excitation of the donor fluorophore at 400 nm, to quantitate reaction progress.

The compounds, compositions, articles, devices, and methods described herein may be understood more readily by reference to the following detailed description of specific aspects of the disclosed subject matter and the Examples included therein and to the Figures.

Before the present compounds, compositions, articles, devices, and methods are disclosed and described it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed compounds, compositions, articles, devices, and methods, examples of which are illustrated in the accompanying Examples and Figures.

Compounds

Disclosed are compounds that have activity as inhibitors of Rho-associated proteinkinases (ROCKs), methods of making and using the compounds, and compositions comprising the compounds. In certain embodiments, the disclosed compounds have the chemical structure shown in Formula I.

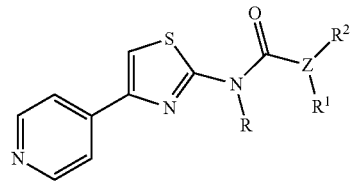

wherein
Z is CR or N;
R is H, alkyl, or heteroalkyl;
$R^1$ is H, alkyl, or heteroalkyl;
$R^2$ is H, alkyl, cycloalkyl, heterocycloalkyl, or aryl, any of which can be optionally substituted with one or more of —OH, —C(O)NH$_2$, acetyl, carbonyl, alkyl, cycloalkyl, heterocycloalkyl, aryl, or heteroaryl, any of which can be optionally substituted with one or more of —OH, —NO$_2$, —NH$_2$, —NR$^6$R$^7$, alkyl, alkoxy, alkylalkoxy, alkoxylalkoxy, halogenated alkoxy, heteroarylcarbonyl, heteroaryl, —OCX$_3$, —OCHX$_2$, —OCH$_2$X, —OSO$_2$CH$_3$, tosyl, or halogen;
$R^6$ and $R^7$ are, independently of one another, H, alkyl, —SO$_2$CH$_3$, —C(O)CH$_3$, or —C(O)NH$_2$;
X is independently H or halogen;
or a pharmaceutically acceptable salt or hydrate thereof.

In one embodiment, $R^2$ is alkyl. In a specific embodiment, $R^2$ is alkyl substituted with at least an aryl. In a more specific embodiment, $R^2$ is alkyl (such as methyl) substituted with a phenyl. In a still further embodiment, $R^2$ is alkyl (such as methyl) substituted with a phenyl which is substituted with an alkoxy group (such as methoxy or ethoxy).

In a more specific aspect, disclose herein are compounds having a chemical structure shown in Formula II.

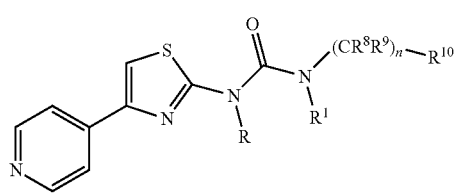

wherein
n is 1, 2, or 3;
R and $R^1$ are as described herein;
$R^8$ and $R^9$ are, independently of one another, H, —OH, acetyl, —C(O)NH$_2$, alkyl, cycloalkyl, hereterocycloalkyl, aryl, or heteroaryl, wherein any one of the alkyl, cycloalkyl, hereterocycloalkyl, aryl, or heteroaryl groups is optionally substituted with one or more of —OH, —NO$_2$, —NH$_2$, —NR$^6$R$^7$, carbonyl, alkoxy, alkyl, —OCX$_3$, —OCHX$_2$, —OCH$_2$X, or halogen, or both $R^8$ together form a carbonyl;
$R^{10}$ is cycloalkyl, heterocycloalkyl, aryl, or heteroaryl, any of which is optionally substituted with one or more of —OH, —C(O)NH$_2$, —C(O)CH$_3$, —NO$_2$, —NH$_2$, —NR$^6$R$^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —OCX$_3$, —OCHX$_2$, —OCH$_2$X, —OSO$_2$CH$_3$, -tosyl, or halogen;
$R^6$, $R^7$, and X are as described herein;
or a pharmaceutically acceptable salt or hydrate thereof.

In specific examples, n is preferably 1. $R^8$ and $R^9$ can be, independently of one another, H, alkyl, or alkyl substituted with —OH, —$NH_2$, alkoxy, or halogen. In some examples, n is 1, and $CR^8R^9$ can be the R isomer of CHalkyl or the S isomer of CHalkyl, wherein the alkyl group is substituted with —OH, $NH_2$, alkoxy, or halogen. $R^{10}$ can preferably be aryl or heteroaryl that is not substituted in the para-position. For example, $R^{10}$ can be an aryl or heteroaryl, optionally substituted in the meta-position with —OH, —C(O)$NH_2$, —$NO_2$, —$NH_2$, —$NR^6R^7$, alkoxy, alkylalkoxy, alkyl, or halogen. In other examples, n is 2 and each $R^8$ and $R^9$ are H, and $R^{10}$ is phenyl.

In still other embodiments, the disclosed compounds have the chemical structure shown in Formula III.

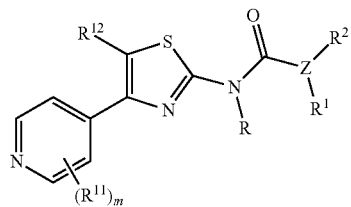

III wherein
Z, R, $R^1$, $R^2$, $R^6$, $R^7$, and X are as defined herein;
m is 1, 2, 3, or 4, indicating that there can be 1, 2, 3, or 4 $R^{11}$ substituents on the pyridiyl ring;
Each $R^{11}$ is, independently of one another, H, —C(O)$NH_2$, —C(O)$CH_3$, —$CO_2H$, —$CO_2$alkyl, —$NO_2$, —$NH_2$, —$NR^6R^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —$OCX_3$, —$OCHX_2$, —$OCH_2X$, —$OSO_2CH_3$, -tosyl, or halogen; and
$R^{12}$ is H, —C(O)$NH_2$, —C(O)$CH_3$, —$CO_2H$, —$CO_2$alkyl, —$NO_2$, —$NH_2$, —$NR^6R^7$, carbonyl, alkyl, alkoxy, alkylalkoxy, alkoxylalkoxy, halogenated alkoxyl, cycloalkyl, heterocycloalkyl, heteroarylcarbonyl, aryl, heteroaryl, —$OCX_3$, —$OCHX_2$, —$OCH_2X$, —$OSO_2CH_3$, -tosyl, or halogen;
or a pharmaceutically acceptable salt or hydrate thereof.

In still other embodiments, the disclosed compounds have the chemical structure shown in Formula IV.

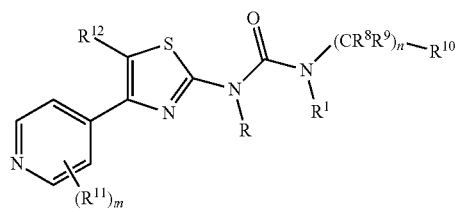

IV wherein
R, $R^1$, $R^2$, $R^6$, $R^7$, $R^8$, $R^9$, $R^{10}$, $R^{11}$, $R^{12}$, X, n, and m are as defined herein.

The structures in Formulas III and IV are similar to those of Formulas I and II, respectively, except for the presence of substituents on the pyridine and/or thiazole rings. A binding analysis indicates that there is space in the binding pocket to accommodate substituents on the pyridine and/or thiazole ring. Thus, disclosed herein are compounds of Formulas III and IV where m can be 1 and $R^{11}$ is at the 2 position or the 3 position of the pyridyl ring. In other embodiments, m can be 2 and the two $R^{11}$ substituents are at the 2 and 3 positions, the 2 and 5 positions, or the 2 and 6 positions of the pyridyl ring. Still further, m can be 3 and the three $R^{11}$ substituents can be at the 2, 3, and 5 positions, the 2, 3, and 6 positions of the pyridyl ring. Also, m can be 4 and thus four $R^{11}$ substituents are present at the 2, 3, 5, and 6 positions of the pyridyl ring. Any of these examples can likewise have $R^{12}$ as defined herein. In a preferred example, $R^{11}$ is an electron donating substituent.

In certain examples, m is 1 and $R^{11}$ is at the 2 position and is F, Cl, Me, or $NH_2$. In other examples, $R^{12}$ is alkyl or $CO_2$alkyl.

Making reference to Formulas II and IV, some specific examples of compounds disclosed herein have n as 1, $R^8$ and $R^9$ as both H, and $R^{10}$ having a structure selected from the following. With reference to Formulas I and III, additional compounds disclosed herein have $R^2$ being selected from the following structures.

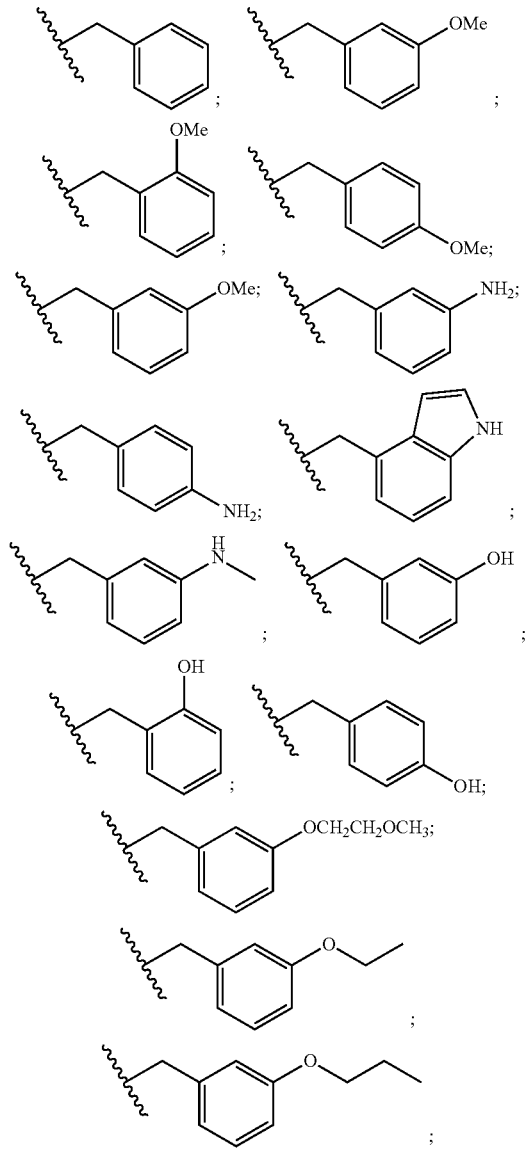

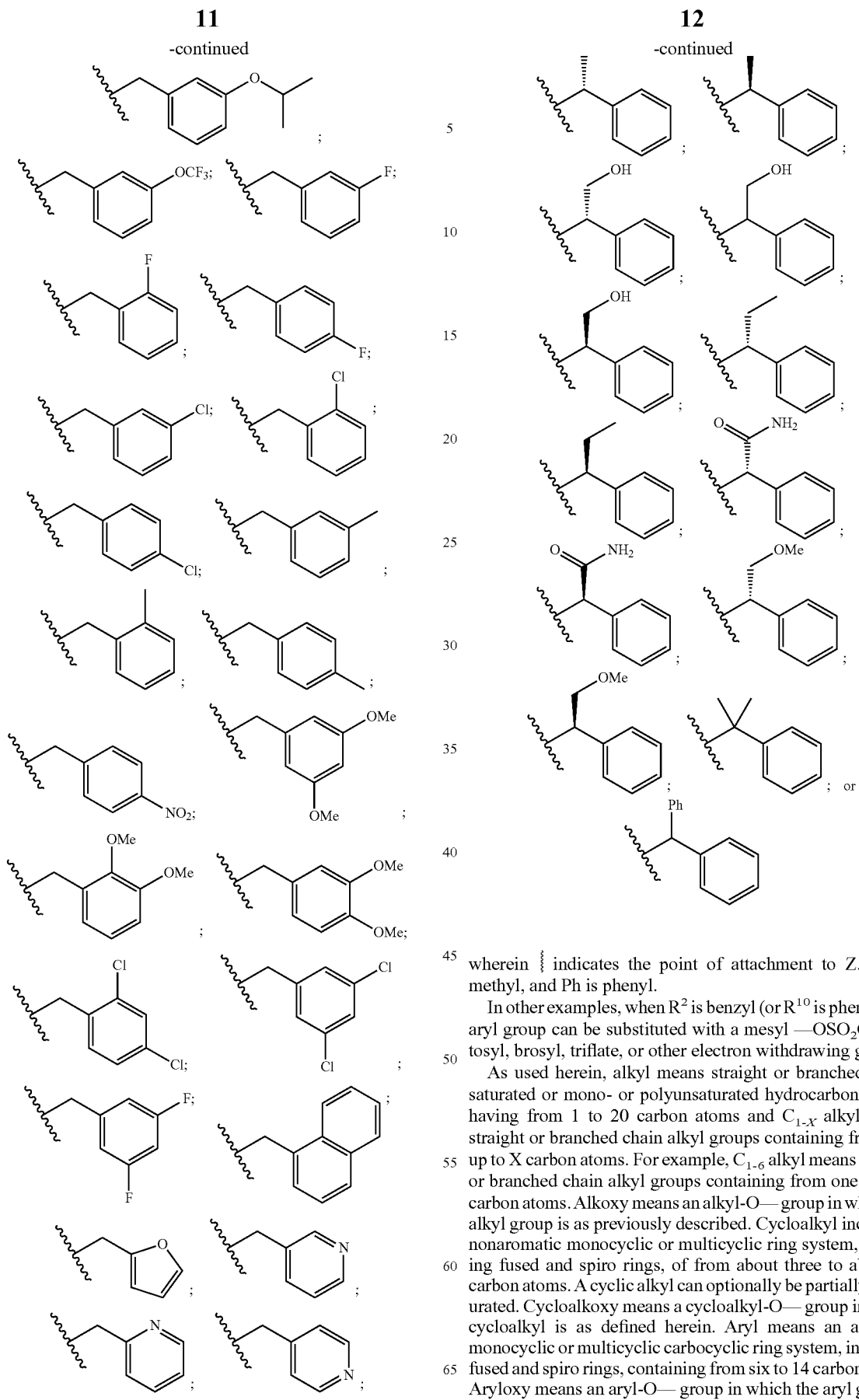

wherein ⁞ indicates the point of attachment to Z. Me is methyl, and Ph is phenyl.

In other examples, when $R^2$ is benzyl (or $R^{10}$ is phenyl), the aryl group can be substituted with a mesyl —$OSO_2CH_3$, or tosyl, brosyl, triflate, or other electron withdrawing group.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl can optionally be partially unsaturated. Cycloalkoxy means a cycloalkyl-O— group in which cycloalkyl is as defined herein. Aryl means an aromatic monocyclic or multicyclic carbocyclic ring system, including fused and spiro rings, containing from six to 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described. The notation C(O) is shorthand for C=O.

Heteroalkyl means a straight or branched-chain having from one to 20 carbon atoms and one or more heteroatoms selected from nitrogen, oxygen, or sulphur, wherein the nitrogen and sulphur atoms can optionally be oxidized, i.e., in the form of an N-oxide or an S-oxide. Heterocycloalkyl means a monocyclic or multicyclic ring system (which can be saturated or partially unsaturated), including fused and spiro rings, of 5 to about 10 atoms in the ring wherein one or more of the atoms in the ring system is an atom other than carbon and is selected from nitrogen, oxygen, silicon, or sulphur atoms. Heteroaryl means a 5 to a 14-membered aromatic monocyclic or multicyclic hydrocarbon ring system, including fused and spiro rings, in which one or more of the atoms in the ring system is an atom other than carbon and is selected from nitrogen, oxygen, silicon, or sulphur and wherein an N atom can be in the form of an N-oxide. Arylcarbonyl means an aryl-C(O)— group in which the aryl group is as described herein. Heteroarylcarbonyl means a heteroaryl-C(O)— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heteroaryloxy means a heteroaryl-O— group in which the heteroaryl group is as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), Bromine (Br), and iodine (I).

Also disclosed herein are pharmaceutically-acceptable salts and hydrates of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It will be appreciated by those skilled in the art that certain of the disclosed compounds can contain one or more asymmetrically substituted carbon atoms which can give rise to stereoisomers. It is understood that the compounds disclosed herein include all such stereoisomers, including enantiomers, and diastereoisomers and mixtures, including racemic and sclameic mixtures thereof.

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a person or animal having a disorder or condition associated with aberrant or excessive ROCK activity or expression in a cell. In one embodiment, the disorder or condition is an oncological disorder or condition. In another embodiment, the disorder or condition is a cardiovascular-related disorder or condition. Examples of cardiovascular disorders and conditions that can be treated using the compounds and/or compositions disclosed herein include, but are not limited to, cerebral and coronary vasospasm, angina, hypertension, pulmonary hypertension, arteriosclerosis, ischemia/reperfusion injury, restenosis, stroke, and heart failure. In a further embodiment, the disorder or condition is a central nervous system (CNS) disorder or condition. Examples of CNS disorders and conditions that can be treated using the compounds and/or compositions disclosed herein include, but are not limited to, spinal cord injury, stroke, and Alzheimer's disease (AD). In one embodiment, a person or animal in need of treatment is administered an effective amount of one or more inhibitor compounds or compositions disclosed herein. In a specific embodiment, the compound is the compound designated herein as 1aa. In a specific embodiment, the compound is the compound designated herein as 1bo. In another embodiment, the compound is the compound designated herein as 1af. In one embodiment, compounds and compositions disclosed herein can be used in the methods of treatment in combination with other ROCK inhibitors, including, but not limited to, Y27632, Wf536, Fasudil, H-1152P, and/or CID5056270.

The disclosed subject matter also concerns methods of inhibiting migratory or invasive capacity of a cell, or inhibiting metastatic potential of a cell. In one embodiment, a cell is contacted with an effective amount of one or more inhibitor compounds or compositions disclosed herein. In a specific embodiment, the compound is the compound designated herein as 1aa. In a specific embodiment, the compound is the compound designated herein as 1bo. In another embodiment, the compound is the compound designated herein as 1af. Cells can be any animal cell, such as a mammalian cell. Cells can be any mammalian cell, such as a human cell, canine cell, feline cell, or equine cell. In one embodiment the cell is a tumor cell, a cancer cell or a transformed cell. In one embodiment, compounds and compositions disclosed herein can be used in combination with other ROCK inhibitors, including, but not limited to, Y27632, Wf536, Fasudil, H-1152P, and/or CID5056270.

The disclosed subject matter also concerns methods for inhibiting ROCK activity in a cell. In one embodiment, a cell is contacted with an effective amount of one or more inhibitor compounds or compositions disclosed herein. In a specific embodiment, the compound is the compound designated herein as 1aa. In a specific embodiment, the compound is the compound designated herein as 1bo. In another embodiment, the compound is the compound designated herein as 1af. Cells can be any animal cell, such as a mammalian cell. Cells can be any mammalian cell, such as a human cell, canine cell, feline cell, or equine cell. In one embodiment the cell is a tumor cell, a cancer cell or a transformed cell. In one embodiment, compounds and compositions disclosed herein can be used in combination with other ROCK inhibitors, including, but not limited to, Y27632, Wf536, Fasudil, H-1152P, and/or CID5056270.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating compounds for administration to a patient are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Examples of cancers that can be treated according to the methods disclosed herein are listed in Table 1.

TABLE 1

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| Acute Myeloid Leukemia, Adult | Hepatocellular (Liver) Cancer, Adult (Primary) |
| Acute Myeloid Leukemia, Childhood | Hepatocellular (Liver) Cancer, Childhood (Primary) |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and Visual Pathway Glioma, Childhood |
| Astrocytoma, Childhood Cerebellar | |
| Astrocytoma, Childhood Cerebral | Intraocular Melanoma |
| Basal Cell Carcinoma | Islet Cell Carcinoma (Endocrine Pancreas) |
| Bile Duct Cancer, Extrahepatic | Kaposi's Sarcoma |
| Bladder Cancer | Kidney (Renal Cell) Cancer |
| Bladder Cancer, Childhood | Kidney Cancer, Childhood |
| Bone Cancer, Osteosarcoma/Malignant Fibrous Histiocytoma | Laryngeal Cancer |
| | Laryngeal Cancer, Childhood |
| Brain Stem Glioma, Childhood | Leukemia, Acute Lymphoblastic, Adult |
| Brain Tumor, Adult | Leukemia, Acute Lymphoblastic, Childhood |
| Brain Tumor, Brain Stem Glioma, Childhood | Leukemia, Acute Myeloid, Adult |
| | Leukemia, Acute Myeloid, Childhood |
| Brain Tumor, Cerebellar Astrocytoma, Childhood | Leukemia, Chronic Lymphocytic |
| | Leukemia, Chronic Myelogenous |
| Brain Tumor, Cerebral Astrocytoma/Malignant Glioma, Childhood | Leukemia, Hairy Cell |
| | Lip and Oral Cavity Cancer |
| | Liver Cancer, Adult (Primary) |
| Brain Tumor, Ependymoma, Childhood | Liver Cancer, Childhood (Primary) |

TABLE 1-continued

Examples of Cancer Types

- Brain Tumor, Medulloblastoma, Childhood
- Brain Tumor, Supratentorial Primitive Neuroectodermal Tumors, Childhood
- Brain Tumor, Visual Pathway and Hypothalamic Glioma, Childhood
- Brain Tumor, Childhood
- Breast Cancer
- Breast Cancer, Childhood
- Breast Cancer, Male
- Bronchial Adenomas/Carcinoids, Childhood
- Burkitt's Lymphoma
- Carcinoid Tumor, Childhood
- Carcinoid Tumor, Gastrointestinal
- Carcinoma of Unknown Primary
- Central Nervous System Lymphoma, Primary
- Cerebellar Astrocytoma, Childhood
- Cerebral Astrocytoma/Malignant Glioma, Childhood
- Cervical Cancer
- Childhood Cancers
- Chronic Lymphocytic Leukemia
- Chronic Myelogenous Leukemia
- Chronic Myeloproliferative Disorders
- Colon Cancer
- Colorectal Cancer, Childhood
- Cutaneous T-Cell Lymphoma, see Mycosis Fungoides and Sézary Syndrome
- Endometrial Cancer
- Ependymoma, Childhood
- Esophageal Cancer
- Esophageal Cancer, Childhood
- Ewing's Family of Tumors
- Extracranial Germ Cell Tumor, Childhood
- Extragonadal Germ Cell Tumor
- Extrahepatic Bile Duct Cancer
- Eye Cancer, Intraocular Melanoma
- Eye Cancer, Retinoblastoma
- Gallbladder Cancer
- Gastric (Stomach) Cancer
- Gastric (Stomach) Cancer, Childhood
- Gastrointestinal Carcinoid Tumor
- Germ Cell Tumor, Extracranial, Childhood
- Germ Cell Tumor, Extragonadal
- Germ Cell Tumor, Ovarian
- Gestational Trophoblastic Tumor
- Glioma, Adult
- Glioma, Childhood Brain Stem
- Glioma, Childhood Cerebral Astrocytoma
- Glioma, Childhood Visual Pathway and Hypothalamic
- Skin Cancer (Melanoma)
- Skin Carcinoma, Merkel Cell
- Small Cell Lung Cancer
- Small Intestine Cancer
- Soft Tissue Sarcoma, Adult
- Soft Tissue Sarcoma, Childhood
- Squamous Cell Carcinoma, see Skin Cancer (non-Melanoma)
- Squamous Neck Cancer with Occult Primary, Metastatic
- Stomach (Gastric) Cancer
- Stomach (Gastric) Cancer, Childhood
- Supratentorial Primitive Neuroectodermal Tumors, Childhood
- T-Cell Lymphoma, Cutaneous, see Mycosis Fungoides and Sézary Syndrome
- Testicular Cancer
- Thymoma, Childhood
- Thymoma and Thymic Carcinoma
- Thyroid Cancer
- Lung Cancer, Non-Small Cell
- Lung Cancer, Small Cell
- Lymphoma, AIDS-Related
- Lymphoma, Burkitt's
- Lymphoma, Cutaneous T-Cell, see Mycosis Fungoides and Sezary Syndrome
- Lymphoma, Hodgkin's, Adult
- Lymphoma, Hodgkin's, Childhood
- Lymphoma, Hodgkin's During Pregnancy
- Lymphoma, Non-Hodgkin's, Adult
- Lymphoma, Non-Hodgkin's, Childhood
- Lymphoma, Non-Hodgkin's During Pregnancy
- Lymphoma, Primary Central Nervous System
- Macroglobulinemia, Waldenström's
- Malignant Fibrous Histiocytoma of Bone/Osteosarcoma
- Medulloblastoma, Childhood
- Melanoma
- Melanoma, Intraocular (Eye)
- Merkel Cell Carcinoma
- Mesothelioma, Adult Malignant
- Mesothelioma, Childhood
- Metastatic Squamous Neck Cancer with Occult Primary
- Multiple Endocrine Neoplasia Syndrome, Childhood
- Multiple Myeloma/Plasma Cell Neoplasm
- Mycosis Fungoides
- Myelodysplastic Syndromes
- Myelodysplastic/Myeloproliferative Diseases
- Myelogenous Leukemia, Chronic
- Myeloid Leukemia, Adult Acute
- Myeloid Leukemia, Childhood Acute
- Myeloma, Multiple
- Myeloproliferative Disorders, Chronic
- Nasal Cavity and Paranasal Sinus Cancer
- Nasopharyngeal Cancer
- Nasopharyngeal Cancer, Childhood
- Neuroblastoma
- Non-Hodgkin's Lymphoma, Adult
- Non-Hodgkin's Lymphoma, Childhood
- Non-Hodgkin's Lymphoma During Pregnancy
- Non-Small Cell Lung Cancer
- Oral Cancer, Childhood
- Oral Cavity Cancer, Lip and Oropharyngeal Cancer
- Osteosarcoma/Malignant Fibrous Histiocytoma of Bone
- Ovarian Cancer, Childhood
- Ovarian Epithelial Cancer
- Ovarian Germ Cell Tumor
- Ovarian Low Malignant Potential Tumor
- Pancreatic Cancer
- Pancreatic Cancer, Childhood
- Pancreatic Cancer, Islet Cell
- Paranasal Sinus and Nasal Cavity Cancer
- Parathyroid Cancer
- Penile Cancer
- Pheochromocytoma
- Pineoblastoma and Supratentorial Primitive Neuroectodermal Tumors, Childhood
- Pituitary Tumor
- Plasma Cell Neoplasm/Multiple Myeloma
- Pleuropulmonary Blastoma
- Pregnancy and Breast Cancer
- Pregnancy and Hodgkin's Lymphoma
- Pregnancy and Non-Hodgkin's Lymphoma
- Primary Central Nervous System Lymphoma
- Prostate Cancer
- Rectal Cancer
- Renal Cell (Kidney) Cancer
- Renal Cell (Kidney) Cancer, Childhood
- Renal Pelvis and Ureter, Transitional Cell Cancer
- Retinoblastoma
- Rhabdomyosarcoma, Childhood
- Salivary Gland Cancer
- Salivary Gland Cancer, Childhood

TABLE 1-continued

Examples of Cancer Types

| | |
|---|---|
| Thyroid Cancer, Childhood | Sarcoma, Ewing's Family of Tumors |
| Transitional Cell Cancer of the Renal Pelvis and Ureter | Sarcoma, Kaposi's |
| | Sarcoma, Soft Tissue, Adult |
| Trophoblastic Tumor, Gestational | Sarcoma, Soft Tissue, Childhood |
| Unknown Primary Site, Carcinoma of, Adult | Sarcoma, Uterine |
| | Sezary Syndrome |
| Unknown Primary Site, Cancer of, Childhood | Skin Cancer (non-Melanoma) |
| | Skin Cancer, Childhood |
| Unusual Cancers of Childhood | |
| Ureter and Renal Pelvis, Transitional Cell Cancer | |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

Also disclosed are methods for inhibiting a ROCK protein in a cell by contacting the cell with an effective amount of a compound, agent, or composition disclosed herein. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of a ROCK protein (e.g., ROCK1). In a specific embodiment, the compound is the compound designated herein as 1aa. In a specific embodiment, the compound is the compound designated herein as 1bo. In another embodiment, the compound is the compound designated herein as 1af.

Also disclosed herein are methods for treating a person or animal having a disorder associated with constitutive, abnormal, or elevated expression of a ROCK protein in a cell, wherein a therapeutically effective amount of a compound, agent, or composition disclosed herein is administered to the person or animal. In many examples herein, the elevated ROCK protein expression is ROCK1. The disorder can be one characterized, for example, by abnormal cell proliferation, cell survival, cell migration, and/or cell differentiation. In a specific embodiment, the compound is the compound designated herein as 1aa. In a specific embodiment, the compound is the compound designated herein as 1bo. In another embodiment, the compound is the compound designated herein as 1af.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that can benefit from the disclosed methods include fish, amphibians, avians, and reptiles. As used herein, the terms "patient" and "subject" are used interchangeably and are intended to include such human and non-human species. Likewise, in vitro methods disclosed herein can be carried out on cells of such human and non-human species.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. In one embodiment, compounds and compositions disclosed herein can be used in combination with other ROCK inhibitors, including, but not limited to, Y27632, Wf536, Fasudil, H-1152P, and CID5056270.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzumab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Examples of some chemotherapeutic agents that can be used according to the disclosed methods are listed in Table 2.

TABLE 2

| Examples of Chemotherapeutic Agents | |
|---|---|
| 13-cis-Retinoic Acid | Mylocel |
| 2-Amino-6-Mercaptopurine | Letrozole |
| 2-CdA | Neosar |
| 2-Chlorodeoxyadenosine | Neulasta |
| 5-fluorouracil | Neumega |
| 5-FU | Neupogen |
| 6-TG | Nilandron |
| 6-Thioguanine | Nilutamide |
| 6-Mercaptopurine | Nitrogen Mustard |
| 6-MP | Novaldex |
| Accutane | Novantrone |
| Actinomycin-D | Octreotide |
| Adriamycin | Octreotide acetate |
| Adrucil | Oncospar |
| Agrylin | Oncovin |
| Ala-Cort | Ontak |
| Aldesleukin | Onxal |
| Alemtuzumab | Oprevelkin |
| Alitretinoin | Orapred |
| Alkaban-AQ | Orasone |
| Alkeran | Oxaliplatin |
| All-transretinoic acid | Paclitaxel |
| Alpha interferon | Pamidronate |
| Altretamine | Panretin |
| Amethopterin | Paraplatin |
| Amifostine | Pediapred |
| Aminoglutethimide | PEG Interferon |
| Anagrelide | Pegaspargase |
| Anandron | Pegfilgrastim |
| Anastrozole | PEG-INTRON |
| Arabinosylcytosine | PEG-L-asparaginase |
| Ara-C | Phenylalanine Mustard |
| Aranesp | Platinol |
| Aredia | Platinol-AQ |
| Arimidex | Prednisolone |
| Aromasin | Prednisone |
| Arsenic trioxide | Prelone |
| Asparaginase | Procarbazine |
| ATRA | PROCRIT |
| Avastin | Proleukin |
| BCG | Prolifeprospan 20 with Carmustine implant |
| BCNU | Purinethol |
| Bevacizumab | Raloxifene |
| Bexarotene | Rheumatrex |
| Bicalutamide | Rituxan |
| BiCNU | Rituximab |
| Blenoxane | Roveron-A (interferon alfa-2a) |
| Bleomycin | Rubex |
| Bortezomib | Rubidomycin hydrochloride |
| Busulfan | Sandostatin |
| Busulfex | Sandostatin LAR |
| C225 | Sargramostim |
| Calcium Leucovorin | Solu-Cortef |
| Campath | Solu-Medrol |
| Camptosar | STI-571 |
| Camptothecin-11 | Streptozocin |
| Capecitabine | Tamoxifen |
| Carac | Targretin |
| Carboplatin | Taxol |
| Carmustine | Taxotere |
| Carmustine wafer | Temodar |
| Casodex | Temozolomide |
| CCNU | Teniposide |

TABLE 2-continued

| Examples of Chemotherapeutic Agents | |
|---|---|
| CDDP | TESPA |
| CeeNU | Thalidomide |
| Cerubidine | Thalomid |
| cetuximab | TheraCys |
| Chlorambucil | Thioguanine |
| Cisplatin | Thioguanine Tabloid |
| Citrovorum Factor | Thiophosphoamide |
| Cladribine | Thioplex |
| Cortisone | Thiotepa |
| Cosmegen | TICE |
| CPT-11 | Toposar |
| Cyclophosphamide | Topotecan |
| Cytadren | Toremifene |
| Cytarabine | Trastuzumab |
| Cytarabine liposomal | Tretinoin |
| Cytosar-U | Trexall |
| Cytoxan | Trisenox |
| Dacarbazine | TSPA |
| Dactinomycin | VCR |
| Darbepoetin alfa | Velban |
| Daunomycin | Velcade |
| Daunorubicin | VePesid |
| Daunorubicin hydrochloride | Vesanoid |
| Daunorubicin liposomal | Viadur |
| DaunoXome | Vinblastine |
| Decadron | Vinblastine Sulfate |
| Delta-Cortef | Vincasar Pfs |
| Deltasone | Vincristine |
| Denileukin diftitox | Vinorelbine |
| DepoCyt | Vinorelbine tartrate |
| Dexamethasone | VLB |
| Dexamethasone acetate | VP-16 |
| dexamethasone sodium phosphate | Vumon |
| | Xeloda |
| Dexasone | Zanosar |
| Dexrazoxane | Zevalin |
| DHAD | Zinecard |
| DIC | Zoladex |
| Diodex | Zoledronic acid |
| Docetaxel | Zometa |
| Doxil | Gliadel wafer |
| Doxorubicin | Glivec |
| Doxorubicin liposomal | GM-CSF |
| Droxia | Goserelin |
| DTIC | granulocyte - colony stimulating factor |
| DTIC-Dome | Granulocyte macrophage colony stimulating factor |
| Duralone | Halotestin |
| Efudex | Herceptin |
| Eligard | Hexadrol |
| Ellence | Hexalen |
| Eloxatin | Hexamethylmelamine |
| Elspar | HMM |
| Emcyt | Hycamtin |
| Epirubicin | Hydrea |
| Epoetin alfa | Hydrocort Acetate |
| Erbitux | Hydrocortisone |
| Erwinia L-asparaginase | Hydrocortisone sodium phosphate |
| Estramustine | Hydrocortisone sodium succinate |
| Ethyol | Hydrocortone phosphate |
| Etopophos | Hydroxyurea |
| Etoposide | Ibritumomab |
| Etoposide phosphate | Ibritumomab Tiuxetan |
| Eulexin | Idamycin |
| Evista | Idarubicin |
| Exemestane | Ifex |
| Fareston | IFN-alpha |
| Faslodex | Ifosfamide |
| Femara | IL-2 |
| Filgrastim | IL-11 |
| Floxuridine | Imatinib mesylate |
| Fludara | Imidazole Carboxamide |
| Fludarabine | Interferon alfa |
| Fluoroplex | Interferon Alfa-2b (PEG conjugate) |
| Fluorouracil | Interleukin-2 |
| Fluorouracil (cream) | Interleukin-11 |
| Fluoxymesterone | Intron A (interferon alfa-2b) |
| Flutamide | Leucovorin |

TABLE 2-continued

Examples of Chemotherapeutic Agents

| | |
|---|---|
| Folinic Acid | Leukeran |
| FUDR | Leukine |
| Fulvestrant | Leuprolide |
| G-CSF | Leurocristine |
| Gefitinib | Leustatin |
| Gemcitabine | Liposomal Ara-C |
| Gemtuzumab ozogamicin | Liquid Pred |
| Gemzar | Lomustine |
| Gleevec | L-PAM |
| Lupron | L-Sarcolysin |
| Lupron Depot | Meticorten |
| Matulane | Mitomycin |
| Maxidex | Mitomycin-C |
| Mechlorethamine | Mitoxantrone |
| Mechlorethamine | M-Prednisol |
| Hydrochlorine | MTC |
| Medralone | MTX |
| Medrol | Mustargen |
| Megace | Mustine |
| Megestrol | Mutamycin |
| Megestrol Acetate | Myleran |
| Melphalan | Iressa |
| Mercaptopurine | Irinotecan |
| Mesna | Isotretinoin |
| Mesnex | Kidrolase |
| Methotrexate | Lanacort |
| Methotrexate Sodium | L-asparaginase |
| Methylprednisolone | LCR |

Kits

The disclosed subject matter also concerns a packaged dosage formulation comprising in one or more containers at least one inhibitor compound or composition disclosed herein, e.g., any compound of Formulas I, II, III, or IV. In one embodiment, a packaged dosage formulation comprises a compound designated herein as 1bo. In another embodiment, the compound is the compound designated herein as 1af. A packaged dosage formulation can optionally comprise in one or more containers a pharmaceutically acceptable carrier or diluent. A packaged dosage formulation can also optionally comprise, in addition to an inhibitor compound or composition disclosed herein, other ROCK inhibitors, including, but not limited to, Y27632, Wf536, Fasudil, H-1152P, and/or CID5056270.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form. A kit can also optionally comprise, in addition to an inhibitor compound or composition disclosed herein, other ROCK inhibitors, including, but not limited to, Y27632, Wf536, Fasudil, H-1152P, and/or CID5056270.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process.

All reagents were purchased from commercial suppliers and used without further purification. Melting points were determined using a Barnstead international melting point apparatus and remain uncorrected. $^1$H NMR spectra were recorded on a Varian Mercury 400 MHz spectrometer with CDCl$_3$ or DMSO-d$_6$ as the solvent. $^{13}$C NMR spectra are recorded at 100 MHz. All coupling constants are measured in Hertz (Hz) and the chemical shifts ($\delta_H$ and $\delta_C$) are quoted in parts per million (ppm) relative to TMS ($\delta$0), which was used as the internal standard. High resolution mass spectroscopy was carried out on an Agilent 6210 LC/MS (ESI-TOF). Microwave reactions were performed in CEM 908005 model and Biotage initiator 8 machines. HPLC analysis was performed using a JASCO HPLC system equipped with a PU-2089 Plus quaternary gradient pump and a UV-2075 Plus UV-VIS detector, using an Alltech Kromasil C-18 column (150×4.6 mm, 5 µm). Thin layer chromatography was performed using silica gel 60 F254 plates (Fisher), with observation under UV when necessary. Anhydrous solvents (acetonitrile, dimethyl formamide, ethanol, isopropanol, methanol and tetrahydrofuran) were used as purchased from Aldrich. HPLC grade solvents (methanol, acetonitrile and water) were purchased from Burdick and Jackson for HPLC and mass analysis.

Synthesis

Compound 1aa and additional analogs 1ab-al, 6a-e, and 8 were prepared via microwave heating following the synthetic routes depicted in Scheme 1. The aminothiazoles 3 were reacted with commercially available isocyanates 4 and 5 and 7 to afford compounds 1, 6, and 8 in poor to moderate yields. Analysis of the crude reaction mixtures by $^1$H NMR revealed complete consumption of the starting materials 3a-b when two equivalents of isocyanate were employed. In addition, concomitant side-reaction, leading to the conversion of the isocyanates into the corresponding diphenylurea A and B, took place under the reaction conditions (NMP, 150° C., μwave, 20 min or DMF, 150° C., μwave, 20 min). Shortening the reaction time, or reducing the equivalents of isocyanate did not prevent the side reaction from occurring. Chromatography on silica gel followed by recrystallization or trituration led to the isolation of the pure products at the expense of the yield.

An initial SAR study revealed the new urea analogs as a promising class of ROCK1 inhibitors. An alternative synthetic approach was developed that allowed efficient production of the target molecules in good yields. A limitation of the initial synthetic route was the lack of inexpensive commercially available isocyanates; a limiting factor to the SAR around the benzyl moiety of compound 1aa). The carbamate 9, prepared from the aminothiazole 3a and phenyl chloroformate, provided a key intermediate and offered an alternative opportunity for the introduction of significant chemical and structural diversity at the benzyl terminus of 1aa via coupling with inexpensive and readily available benzylamines, amino acids, anilines, and aliphatic amines. This proved to be successful, allowing expansion of library 1 under much milder and efficient conditions than those previously followed.

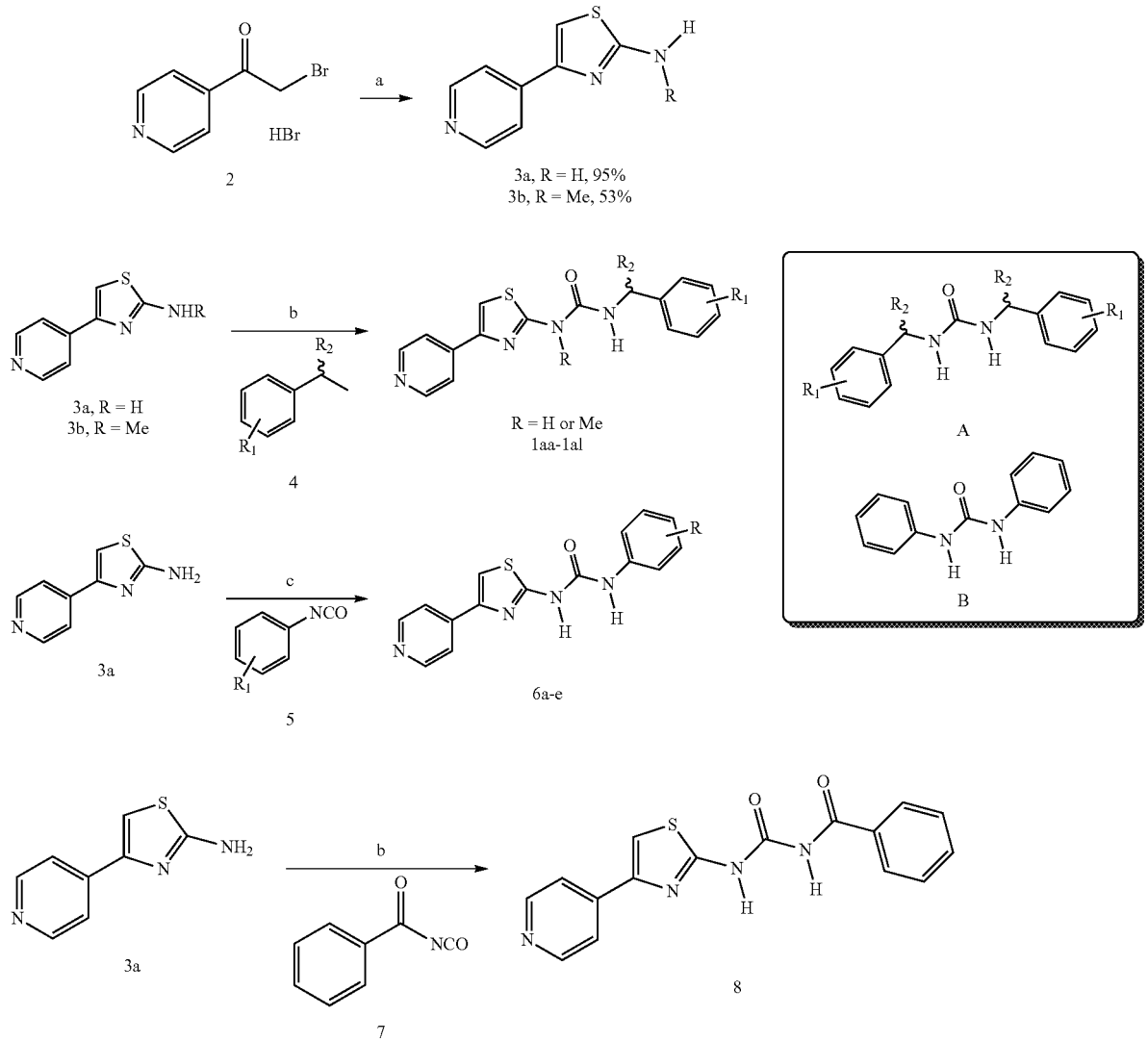

Scheme 1. First approach to the synthesis of ureas 1, 6, and 8

Reagents & Conditions: a) EtOH, Thiourea or N-methyl thiourea, 100° C., Biotage μw, 30 min; b) NMP, 150° C., Biotage μw, 20 min; c) DMF, 150° C., Biotage μw, 10 min;

Scheme 2. Second approach to the synthesis of ureas 1

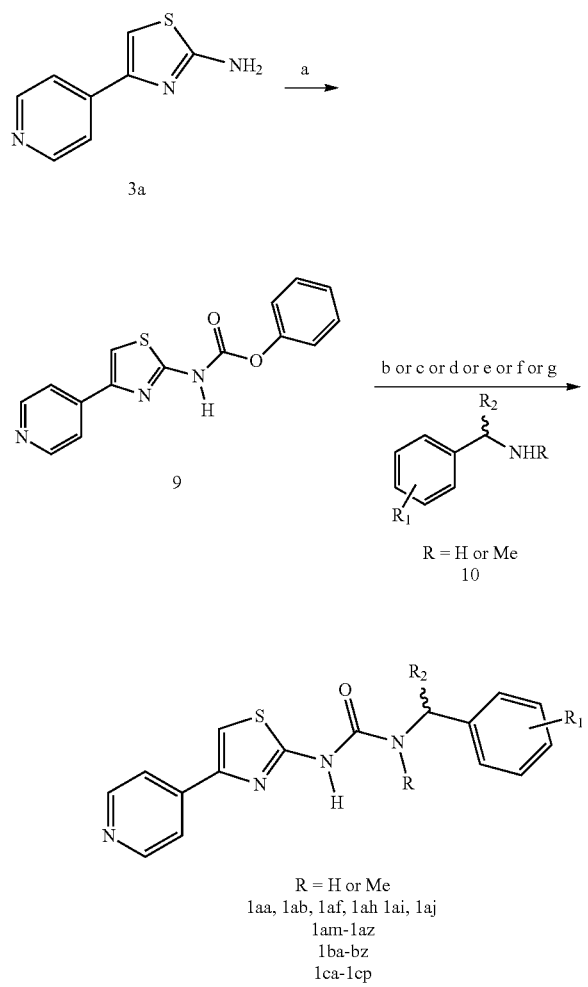

Reagents & Conditions: a) Py, DCM, Phenylchloroformate, rt, 3 h, Ar; b) THF, 120° C., sealed tube, heating block, 1 h; c) THF, 100° C., CEM µw, 20 min, d) THF, DIPEA, 100° C., CEM µw, 20 min, e) THF, Et₃N, 100° C., CEM µw, 20 min, f) THF, CH₃CN, 80° C., Biotage µw, 20 min, g) THF, Sealed tube, 159° C., 4 h.

As shown in Scheme 2, library 1 could be prepared by heating the reaction mixture in a sealed tube at 120° C. (Scheme 2, conditions b). By means of a heating block parallel station, the generation of the library was performed in a combinatorial fashion. Moreover, microwave heating provided an efficient and convenient alternative to conventional heating for the synthesis of library 1 (Scheme 2, conditions c, d, e, and f). Under the optimized conditions, no side reactions occurred, and the pure products were generally isolated in good yields (Scheme 2). In order to validate the new synthetic protocol, the original hit 1aa and the most active analogs 1ab, 1af, 1ah, 1ai, and 1aj (originally prepared as described in Scheme 1) were synthesized using the new synthetic route. The different batches displayed comparable analytical data and comparable potency in the ROCK1 FRET-based Z'-Lyte kinase assay.

The corresponding Mesilate and HCl salts of selected library members were also synthesized according to the conditions described in Scheme 3.

Scheme 3. Synthesis of the corresponding Mesylate and HCl salts of selected compounds of library 1

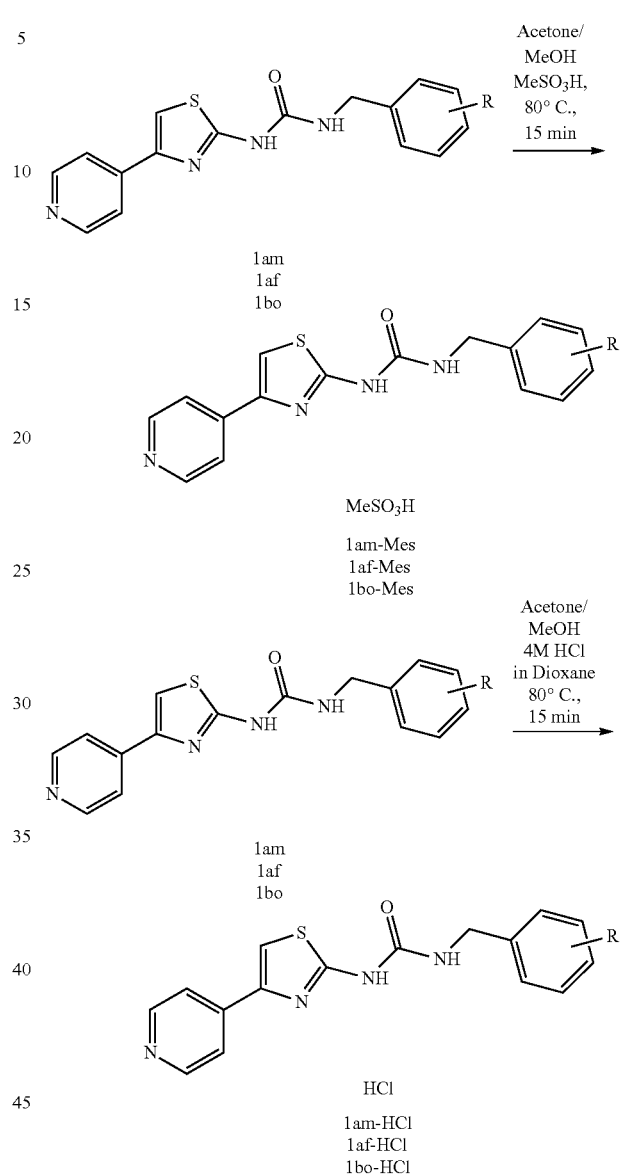

Finally, in order to expand the SAR around the urea scaffold, further analogs were synthesized following the routes described in the Scheme 4 and 5.

Scheme 4. Expansion of library 1

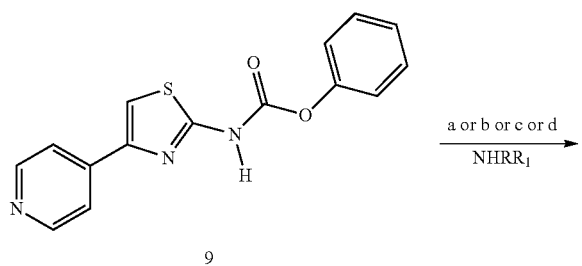

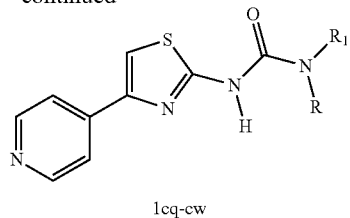

1cq-cw

Reagents & Conditions: a) THF, 100° C., CEM μw, 40 min, b) THF, 100° C., CEM μw, 20 min, c) THF, DIPEA, 100° C., CEM μw, 20 min, d) THF, 120° C., sealed tube, heating block, 1 h;

Scheme 5. Synthesis of piperazine analogs of 1aa

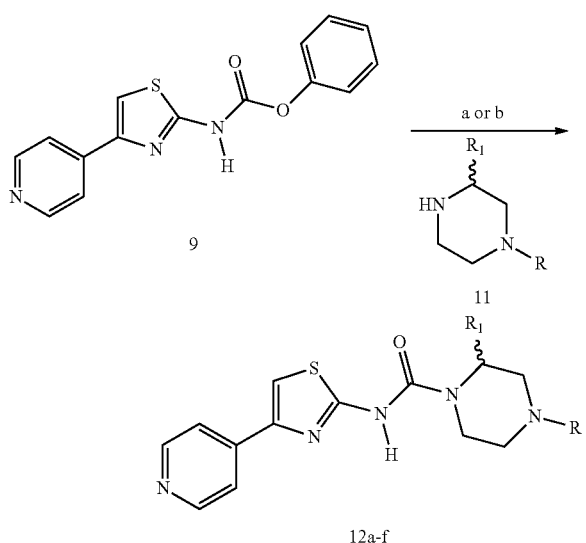

12a-f

Reagents & Conditions: a) THF, 100° C., CEM μw, 40 min, b) THF, 120° C., sealed tube, heating block, 1 h;

The structures of all the final compounds were confirmed by their spectroscopy data. In addition, HPLC methods (typically two methods) were also developed to assess the purity (generally >96%) of the compounds prior to biological screening. Additionally, HPLC methods were developed for the chiral compounds in order to determine the enantiomeric purity (generally >95%).

Compound 3a

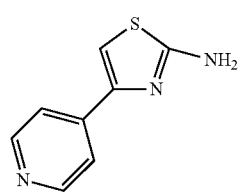 [SMILES: Nc1nc(-c2ccncc2)cs1]

4-(Pyridin-4-yl)thiazol-2-amine

Synthesis of batch 1. A mixture of 4-(bromoacetyl)pyridine hydrobromide (2) (2.21 g, 7.90 mmol), thiourea (0.60 g, 7.90 mmol) in anhydrous EtOH (10 ml) was stirred in a Biotage microwave at 100° C. for 30 min. After colling to room temperature, the solid precipitate was filtered, dried under vacuum.

Synthesis of batch 2. A mixture of 4-(bromoacetyl)pyridine hydrobromide (2) (2.54 g, 9.06 mmol), thiourea (0.69 g, 9.06 mmol) in anhydrous EtOH (10 ml) was stirred in a Biotage microwave at 100° C. for 30 min. After colling to room temperature, the solid precipitate was filtered, dried under vacuum.

Synthesis of batch 3. A mixture of 4-(bromoacetyl)pyridine hydrobromide (2) (2.16 g, 7.73 mmol), thiourea (0.58 g, 7.73 mmol) in anhydrous EtOH (10 ml) was stirred in a Biotage microwave at 100° C. for 30 min. After colling to room temperature, the solid precipitate was filtered, dried under vacuum.

Batches 1, 2, and 3 were combined, suspended in an aqueous sat. solution of $NaHCO_3$, filtered, dried under vacuum to provide the title compound as a pale pink solid (5.53 g, 31.27 mmol, 95%). $^1$H NMR (400 MHz, $CD_3OD$) δ 8.49 (d, J=6.3 Hz, 2H), 7.79 (d, J=6.3 Hz, 2H), 7.25 (s, 1H).

Compound 1aa

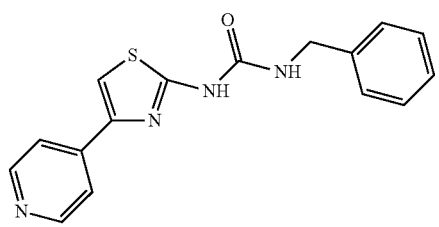 [SMILES: O=C(NCc1ccccc1)Nc1nc(-c2ccncc2)cs1]

1-Benzyl-3-(4-(pyridin-4-yl)thiazol-2-yl)urea

A mixture of 3a (0.251 g, 1.41 mmol), benzyl isocyanate (0.357 g, 2.82 mmol) in anhydrous NMP (1.4 ml), was stirred in a Biotage microwave reactor at 150° C. for 20 min. After cooling to room temperature, DCM was added and the organic layer washed with water and brine, dried over $Na_2SO_4$ and the solvent removed under reduced pressure. Chromatography on silica gel performed using the FlashMaster 3 purification station afforded 1aa as an off white solid (0.156 g, 0.503 mmol, 35%). $^1$H NMR (400 MHz, DMSO-$d_6$) δ 10.82 (s, 1H), 8.56 (d, J=5.8 Hz, 2H), 7.81 (s, 1H), 7.77 (d, J=5.7 Hz, 2H), 7.34-7.22 (m, 5H), 7.01 (t, J=5.6 Hz, 1H), 4.34 (d, J=6.0 Hz, 2H); $^{13}$C NMR (400 MHz, DMSO-$d_6$) δ 161.00, 154.63, 150.85, 146.80, 141.70, 140.18, 129.08, 127.82, 127.62, 120.48, 111.74, 43.57. HRMS (ESI+ve) m/z calculated for $C_{16}H_{14}N_4OS$ $(M+H)^+$ 311.0961, found 311.0970.

Compound 1ab

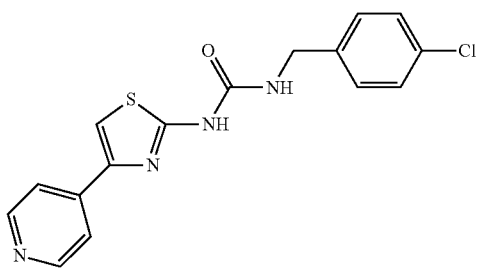 [SMILES: O=C(NCc1ccc(Cl)cc1)Nc1nc(-c2ccncc2)cs1]

1-(4-Chlorobenzyl)-3-(4-(pyridin-4-yl)thiazol-2-yl)urea

This was prepared from 3a (0.097 g, 0.548 mmol) and 4-chlorobenzyl isocyanate (0.183 g, 1.09 mmol) in the same manner as described for 1aa. Chromatography on silica gel performed using the FlashMaster 3 purification station afforded 1ab as an off white solid (0.019 g, 0.055 mmol, 10%). ¹H NMR (DMSO-d₆) δ 10.89 (s, 1H), 8.56 (d, J=6.0 Hz, 2H), 7.81 (s, 1H), 7.77 (d, J=6.1 Hz, 2H), 7.38 (d, J=8.4 Hz, 2H), 7.31 (d, J=8.3 Hz, 2H), 7.04 (t, J=7.0 Hz, 1H), 4.32 (d, J=5.7 Hz, 2H); HPLC purity 9% {$t_R$=min, Flow 1 ml/min, [(CH₃CN/(0.1% TFA in H₂O):30/70]}; purity % {$t_R$=min, Flow 1 ml/min, [(MeOH/(0.1% TFA in H₂O):50/50]}; HRMS (ESI+ve) m/z calculated for $C_{16}H_{14}FlN_4OS$ (M+H)⁺ 345.0571, found.

Compound 1ac

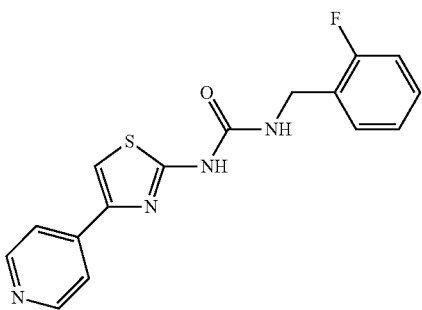 [SMILES: O=C(NCc1ccccc1F)Nc1nc(-c2ccncc2)cs1]

1-(2-Fluorobenzyl)-3-(4-(pyridin-4-yl)thiazol-2-yl)urea

This was prepared from 3a (0.113 g, 0.638 mmol) and 2-fluorobenzyl isocyanate (0.192 g, 1.27 mmol) in the same manner as described for 1aa. Chromatography on silica gel performed using the FlashMaster 3 purification station afforded 1ac as a pale yellow solid (0.134 g, 0.408 mmol, 64%). ¹H NMR (400 MHz, DMSO-d₆) δ 10.84 (s, 1H), 8.57 (d, J=6.1 Hz, 2H), 7.82 (s, 1H), 7.77 (d, J=6.1 Hz, 2H), 7.37-7.28 (m, 2H), 7.20-7.15 (m, 2H), 7.04 (t, J=6.2 Hz, 1H), 4.39 (d, J=5.9 Hz, 2H); HPLC purity 99.02% {$t_R$=5.987 min, Flow 1 ml/min, [(CH₃CN/(0.1% TFA in H₂O):30/70]}; purity 97.76% {$t_R$=6.827 min, Flow 1 ml/min, [(MeOH/(0.1% TFA in H₂O):50/50]}; HRMS (ESI+ve) m/z calculated for $C_{16}H_{14}FN_4OS$ (M+H)⁺ 329.0866, found 329.0867.

Compound 1ad

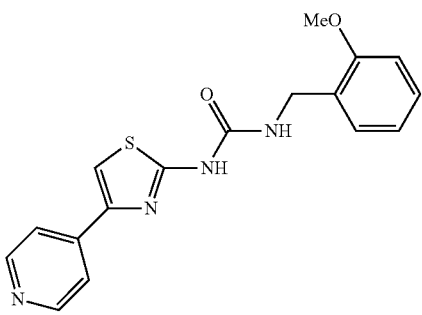 [SMILES: O=C(NCc1ccccc1Cl)Nc1nc(-c2ccncc2)cs1]

1-(2-Methoxybenzyl)-3-(4-(pyridin-4-yl)thiazol-2-yl)urea

This was prepared from 3a (0.112 g, 0.632 mmol) and 2-methoxybenzyl isocyanate (0.206 g, 1.26 mmol) in the same manner as described for 1aa. Chromatography on silica gel performed using the FlashMaster 3 purification station, followed by trituration with ethyl acetate afforded 1ad as a white solid (0.066 g, 0.194 mmol, 31%). ¹H NMR (400 MHz, DMSO-d₆) δ 10.77 (s, 1H), 8.57 (d, J=6.0, Hz, 2H), 7.81 (s, 1H), 7.77 (d, J=6.1 Hz, 2H), 7.26 (t, J=7.3 Hz, 1H), 7.20 (d, J=6.5 Hz, 1H), 7.00 (d, J=7.9 Hz, 1H), 6.92-6.88 (m 2H), 4.30 (d, J=6.0 Hz, 2H), 3.82 (s, 3H); HPLC purity 99.69% {$t_R$=6.840 min, Flow 1 ml/min, [(CH₃CN/(0.1% TFA in H₂O):30/70]}; purity 97.43% {$t_R$=8.400 min, Flow 1 ml/min, [(MeOH/(0.1% TFA in H₂O):50/50]}; HRMS (ESI+ve) m/z calculated for $C_{17}H_{17}N_4O_2S$ (M+H)⁺ 341.1066, found 341.1063.

Compound 1ae

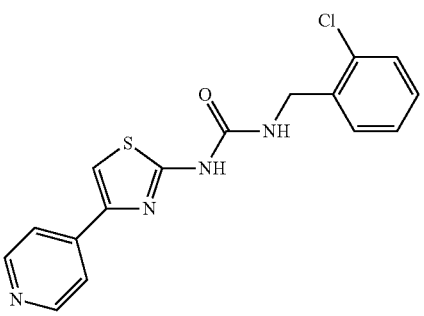

1-(2-Chlorobenzyl)-3-(4-(pyridin-4-yl)thiazol-2-yl)urea

This was prepared from 3a (0.115 g, 0.649 mmol) and 2-chlorobenzyl isocyanate (0.217 g, 1.29 mmol) in the same manner as described for 1aa. Chromatography on silica gel performed twice using the FlashMaster 3 purification station, afforded 1ae as an off white solid (0.027 g, 0.078 mmol, 12%). ¹H NMR (400 MHz, DMSO-d₆) δ 10.77 (s, 1H), 8.57 (d, J=6.0, Hz, 2H), 7.81 (s, 1H), 7.77 (d, J=6.1 Hz, 2H), 7.26 (t, J=7.3 Hz, 1H), 7.20 (d, J=6.5 Hz, 1H), 7.00 (d, J=7.9 Hz, 1H), 6.92-6.88 (m 2H), 4.30 (d, J=6.0 Hz, 2H), 3.82 (s, 3H). HPLC purity 98.99% {$t_R$=9.360 min, Flow 1 ml/min, [(CH₃CN/(0.1% TFA in H₂O):30/70]}; purity 99.04% {$t_R$=11.440 min, Flow 1 ml/min, [(MeOH/(0.1% TFA in H₂O):50/50]}; HRMS (ESI+ve) m/z calculated for $C_{16}H_{14}ClN_4OS$ (M+H)⁺ 345.0571, found 345.0570.

Compound 1af

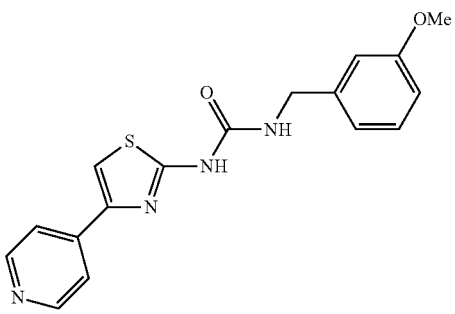 [SMILES: COc1cccc(CNC(=O)Nc2nc(-c3ccncc3)cs2)c1]

1-(3-Methoxybenzyl)-3-(4-(pyridin-4-yl)thiazol-2-yl)urea

This was prepared from COMPOUND834 (0.123 g, 0.694 mmol) and 3-methoxybenzyl isocyanate (0.226 g, 1.38 mmol) in the same manner as described for 1aa. Chromatography on silica gel performed using the FlashMaster 3 purification station, afforded 1af as an off white solid (0.122 g, 0.350 mmol, 52%). $^1$H NMR (400 MHz, DMSO-$d_6$) δ 10.82 (s, 1H), 8.57 (d, J=6.0 Hz, 2H), 7.82 (s, 1H), 7.77 (d, J=6.2 Hz, 2H), 7.24 (t, J=8.1 Hz, 1H), 7.00 (t, J=6.0 Hz, 1H), 6.79-6.82 (m, 3H), 4.31 (d, J=5.9 Hz, 1H), 3.72 (s, 3H).); $^{13}$C NMR (400 MHz, DMSO-$d_6$) δ 161.01, 160.01, 154.64, 150.84, 146.80, 141.79, 141.70, 130.18, 120.48, 119.91, 113.49, 112.90, 111.74, 55.66, 43.52; HPLC purity 99.01% {$t_R$=5.640 min, Flow 1 ml/min, [(CH$_3$CN/(0.1% TFA in H$_2$O):30/70]}; purity 98.78% {$t_R$=6.427 min, Flow 1 ml/min, [(MeOH/(0.1% TFA in H$_2$O):50/50]}; HRMS (ESI+ve) m/z calculated for $C_{17}H_{17}N_4O_2S$ (M+H)$^+$ 341.1066, found 341.1064.

Compound 1ag

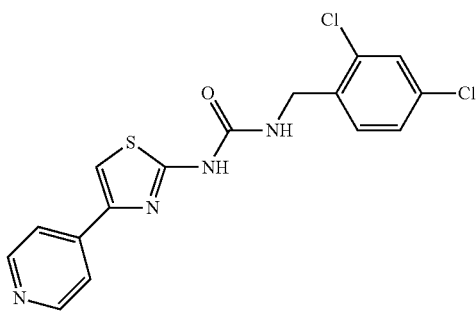 [SMILES: O=C(NCc1ccc(Cl)cc1Cl)Nc1nc(-c2ccncc2)cs1]

1-(2,4-Dichlorobenzyl)-3-(4-(pyridin-4-yl)thiazol-2-yl)urea

This was prepared from 3a (0.120 g, 0.677 mmol) and 3,4-dichlorobenzyl isocyanate (0.273 g, 1.35 mmol) in the same manner as described for 1aa. Chromatography on silica gel performed twice using the FlashMaster 3 purification station, afforded 1ag as an off white solid (0.071 g, 0.187 mmol, 28%). $^1$H NMR (400 MHz, DMSO-$d_6$) δ 11.00 (s, 1H), 8.57 (d, J=6.1 Hz, 2H), 7.83 (s, 1H), 7.78 (d, J=6.1 Hz, 2H), 7.63 (d, J=2.1 Hz, 1H), 7.44 (dd, J=2.1, 8.3 Hz, 1H), 7.37 (d, J=8.3 Hz, 1H), 7.13 (t, J=5.8 Hz, 1H), 4.38 (d, J=6.1 Hz, 2H); HPLC purity 98.65% {$t_R$=5.373 min, Flow 1 ml/min, [(CH$_3$CN/(0.1% TFA in H$_2$O):30/70]}; purity 97.89% {$t_R$=9.480 min, Flow 1 ml/min, [(MeOH/(0.1% TFA in H$_2$O): 60/40]}; HRMS (ESI+ve) m/z calculated for $C_{16}H_{13}Cl_2N_4OS$ (M+H)$^+$ 379.0181, found 379.0173.

Compound 1ah

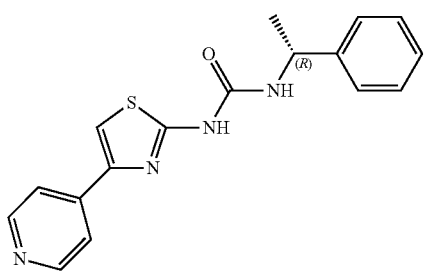

(R)-1-(1-Phenylethyl)-3-(4-(pyridin-4-yl)thiazol-2-yl)urea

This was prepared from 3a (0.126 g, 0.711 mmol) and (R)-(+)-alpha-methylbenzyl isocyanate (0.209 g, 1.42 mmol) in the same manner as described for 1aa. Chromatography on silica gel performed twice using the FlashMaster 3 purification station, afforded 1ah as a white solid (0.125 g, 0.385 mmol, 54%). $^1$H NMR (400 MHz, DMSO-$d_6$) δ 10.51 (s, 1H), 8.56 (d, J=5.8 Hz, 2H), 7.80 (s, 1H), 7.76 (d, J=6.0 Hz, 2H), 7.36-7.31 (m, 4H), 7.26-7.24 (m, 1H), 7.02 (d, J=7.7 Hz, 1H), 4.84 (quint, J=7.3 Hz, 1H), 1.40 (d, J=6.9 Hz, 6H); $^{13}$C NMR (400 MHz, DMSO-$d_6$) δ 160.80, 153.72, 150.84, 146.77, 145.01, 141.64, 129.14, 127.61, 126.47, 120.48, 111.71, 49.71, 23.54; HPLC purity 99.22% {$t_R$=7.907 min, Flow 1 ml/min, [(CH$_3$CN/(0.1% TFA in H$_2$O):30/70]}; purity 99.51% {$t_R$=8.653 min, Flow 1 ml/min, [(MeOH/(0.1% TFA in H$_2$O):50/50]}; HRMS (ESI+ve) m/z calculated for $C_{17}H_{17}N_4OS$ (M+H)$^+$ 3251117, found 325.1116.

The enantiomeric excess was determined by HPLC using a Chiralcel OJ column [(Iso-propanol/Hexane:50/50), Flow 1 ml/min], $t_{R1}$=9.067 min, Area % 0.404 (minor), $t_{R2}$=14.300 min, Area % 98.378 (major).

Compound 1ai

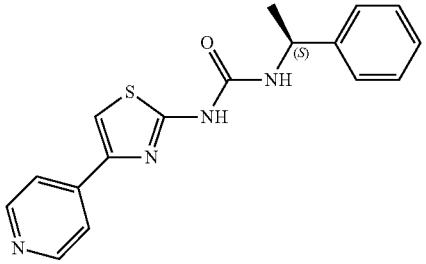

(S)-1-(1-Phenylethyl)-3-(4-(pyridin-4-yl)thiazol-2-yl)urea

This was prepared from 3a (0.110 g, 0.621 mmol) and (S)-(−)-alpha-methylbenzyl isocyanate (0.182 g, 1.24 mmol) in the same manner as described for 1aa. Chromatography on silica gel performed twice using the FlashMaster 3 purification station, afforded 1ai as a white solid (0.87 g, 0.268 mmol, 43%). $^1$H NMR (400 MHz, DMSO-$d_6$) δ 10.52 (s, 1H), 8.57 (d, J=6.0 Hz, 2H), 7.80 (s, 1H), 7.76 (d, J=6.1 Hz, 2H), 7.37-7.32 (m, 4H), 7.27-7.21 (m, 1H), 7.03 (d, J=8.3 Hz, 1H), 4.84 (p, J=6.6 Hz, 1H), 1.41 (d, J=6.9 Hz, 3H); $^{13}$C NMR (100 MHz, DMSO-$d_6$) δ 160.79, 153.71, 150.85, 146.76, 145.01, 141.64, 129.14, 127.61, 126.47, 120.48, 111.72, 49.71, 23.54; HPLC purity 99.74% {$t_R$=7.480 min, Flow 1 ml/min, [(CH$_3$CN/(0.1% TFA in H$_2$O):30/70]}; purity 99.541% {$t_R$=8.653 min, Flow 1 ml/min, [(MeOH/(0.1% TFA in H$_2$O): 50/50]}; HRMS (ESI+ve) m/z calculated for $C_{17}H_{17}N_4OS$ (M+H)$^+$ 3251117, found 325.1116.

The enantiomeric excess was determined by HPLC using a Chiralcel OJ column [(Iso-propanol/Hexane:50/50), Flow 1 ml/min], $t_{R1}$=9.067 min, Area % 99.503 (major).

Compound 1aj

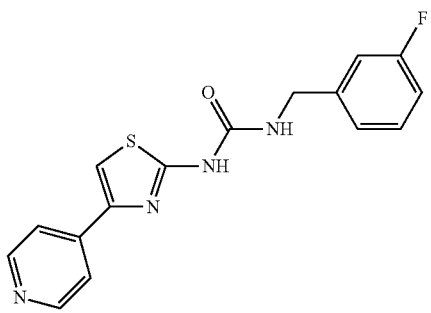 [SMILES: O=C(NCc1cccc(F)c1)Nc1nc(-c2ccncc2)cs1]

1-(3-Fluorobenzyl)-3-(4-(pyridin-4-yl)thiazol-2-yl)urea

This was prepared from 3a (0.105 g, 0.593 mmol) and 3-fluorobenzyl isocyanate (0.179 g, 1.18 mmol) in the same manner as described for 1aa. Chromatography on silica gel performed using the FlashMaster 3 purification station afforded 1aj as an off white solid (0.019 g, 0.030 mmol, 5%). $^1$H NMR (400 MHz, DMSO-$d_6$) δ 10.90 (s, 1H, disappeared on D$_2$O shake), 8.57 (d, J=6.1 Hz, 2H,), 7.82 (s, 1H), 7.78 (d, J=6.1 Hz, 2H,), 7.39-7.34 (m, 1H), 7.149-7.04 (m, 4H), 4.36 (d, J=6.0 Hz, 2H); $^{13}$C NMR (100 MHz, DMSO-$d_6$) δ 162.90 (d, J=241.9 Hz, C—F), 160.98, 154.72, 150.85, 146.81, 143.39 (d, J=7.0 Hz, C), 141.70, 131.02 (d, J=8.25 Hz, CH), 123.74 (d, J=2.67 Hz, CH), 120.49, 114.48 (d, J=11.8 Hz, CH), 114.26 (d, J=11.15 Hz, CH), 111.79, 43.10 (d, J=1.4 Hz, CH$_2$); HPLC purity 99.27% {$t_R$=6.400 min, Flow 1 ml/min, [(CH$_3$CN/(0.1% TFA in H$_2$O):30/70]}; purity 99.11% {$t_R$=7.133 min, Flow 1 ml/min, [(MeOH/(0.1% TFA in H$_2$O):50/50]}; HRMS (ESI+ve) m/z calculated for C$_{16}$H$_{14}$FN$_4$OS (M+H)$^+$ 329.0866, found 329.0870.

Compound 1ak

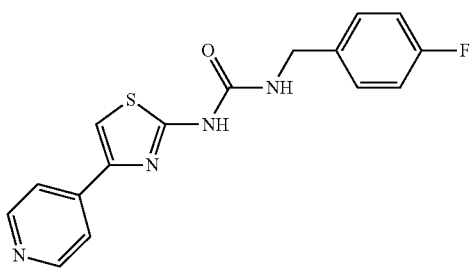 [SMILES: O=C(NCc1ccc(F)cc1)Nc1nc(-c2ccncc2)cs1]

1-(4-Fluorobenzyl)-3-(4-(pyridin-4-yl)thiazol-2-yl)urea

This was prepared from 3a (0.090 g, 0.508 mmol) and 4-fluorobenzyl isocyanate (0.153 g, 1.01 mmol) in the same manner as described for 1aa. Chromatography on silica gel performed using the FlashMaster 3 purification station afforded 1ak as an off white solid (0.026 g, 0.079 mmol, 16%). $^1$H NMR (400 MHz, DMSO-$d_6$) δ 10.52 (s, 1H), 8.57 (d, J=6.0 Hz, 2H), 7.80 (s, 1H), 7.76 (d, J=6.1 Hz, 2H), 7.37-7.32 (m, 4H), 7.27-7.21 (m, 1H), 7.03 (d, J=8.3 Hz, 1H), 4.84 (p, J=6.6 Hz, 1H), 1.41 (d, J=6.9 Hz, 3H); HPLC purity 99.59% {$t_R$=6.453 min, Flow 1 ml/min, [(CH$_3$CN/(0.1% TFA in H$_2$O):30/70]}; purity 98.54% {$t_R$=7.093 min, Flow 1 ml/min, [(MeOH/(0.1% TFA in H$_2$O):50/50]; HRMS (ESI+ve) m/z calculated for C$_{16}$H$_{14}$FN$_4$OS (M+H)$^+$ 329.0866, found 329.0866.

Compound 1ak1

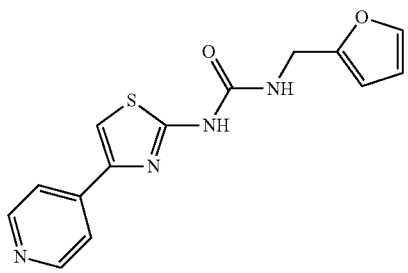 [SMILES: O=C(NCc1ccco1)Nc1nc(-c2ccncc2)cs1]

1-(Furan-2-ylmethyl)-3-(4-(pyridin-4-yl)thiazol-2-yl)urea

This was prepared from 3a (0.094 g, 0.531 mmol) and furfuryl isocyanate (0.130 g, 1.06 mmol) in the same manner as described for 1aa. Chromatography on silica gel performed using the FlashMaster 3 purification station afforded 1al as an off white solid (0.077 g, 0.256 mmol, 48%). $^1$H NMR (400 MHz, DMSO-$d_6$) 10.75 (s, 1H), 8.57 (d, J=5.8 Hz, 2H), 7.83 (s, 1H), 7.77 (d, J=6.0 Hz, 2H,), 7.59-7.58 (m, 1H), 6.94 (t, J=5.5 Hz, 1H), 6.39 (dd, J=1.8, 2.8 Hz, 1H), 6.27 (d, J=3.2 Hz, 1H), 4.34 (d, J=5.7 Hz, 2H). HPLC purity 99.57% {$t_R$=3.240 min, Flow 1 ml/min, [(CH$_3$CN/(0.1% TFA in H$_2$O):30/70]}; purity 99.81% {$t_R$=7.360 min, Flow 1 ml/min, [(MeOH/(0.1% TFA in H$_2$O):40/60]}; HRMS (ESI+ve) m/z calculated for C$_{14}$H$_{13}$N$_4$O$_2$S (M+H)$^+$ 301.0753, found 301.0751.

Compound 8

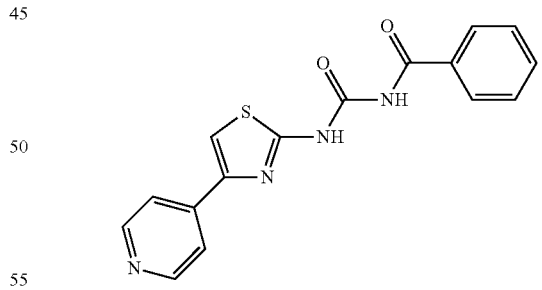

N-(4-(Pyridin-4-yl)thiazol-2-ylcarbamoyl)benzamide

This was prepared from 3a (0.109 g, 0.615 mmol), benzoyl isocyanate (0.181 g, 1.23 mmol) in anhydrous NMP (0.6 ml), in the same manner as described for 1aa. After cooling to room temperature, ethyl acetate was added to the reaction mixture, the solid precipitate was filtered, triturated with methanol, filtered and dried under vacuum. The pure product 8 was obtained as an off white solid (0.117 g, 0.360 mmol, 59%). $^1$H NMR (400 MHz, DMSO-$d_6$) δ 12.07 (s, 1H), 11.56

(s, 1H), 8.63 (d, J=6.2 Hz, 2H), 8.11 (s, 1H), 8.03 (d, J=7.3 Hz, 2H), 7.92 (d, J=6.2 Hz, 2H), 7.68 (t, J=7.4 Hz, 1H), 7.56 (t, J=7.8 Hz, 2H); HRMS (ESI+ve) m/z calculated for $C_{16}H_{13}N_4O_2S$ (M+H)$^+$ 325.0753, found 325.0744.

Compound 3b

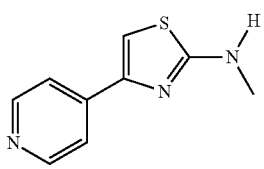

N-Methyl-4-(pyridin-4-yl)thiazol-2-amine

A mixture of 4-(bromoacetyl)pyridine hydrobromide 2 (0.429 g, 1.53 mmol), N-methyl thiourea (0.138 g, 1.53 mmol) in anhydrous EtOH (3 ml) was stirred in a Biotage microwave at 100° C. for 30 min. After cooling to room temperature, the solid precipitate was filtered, dried under vacuum, suspended in a saturated solution of sodium bicarbonate (aq., saturated), filtered, washed with water, and dried under vacuum. The pure aminothiazole 3b was obtained as a cream solid (0.154 g, 0.82 mmol, 53%). $^1$H NMR (400 MHz, DMSO-d$_6$) δ 8.52 (d, J=6.1 Hz, 2H), 7.74 (d, J=6.1 Hz, 2H), 7.70 (bs, 1H), 7.43 (s, 1H).

Compound 1al

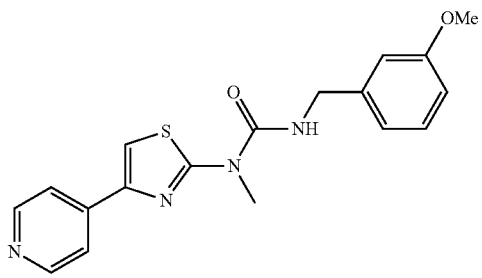 [SMILES: COc1cccc(CNC(=O)N(C)c2nc(-c3ccncc3)cs2)c1]

3-(3-Methoxybenzyl)-1-methyl-1-(4-(pyridin-4-yl)thiazol-2-yl)urea

This was prepared from 3b (0.086 g, 0.450 mmol) and 3-methoxybenzylisocyanate (0.146 g, 0.900 mmol) in the same manner as described for 1aa. After cooling to room temperature, the solvent was removed under reduced pressure. Chromatography on silica gel performed using the FlashMaster 3 purification station, followed by trituration with diethyl ether afforded 1al as a white solid (0.085 g, 0.240 mmol, 53%). $^1$H NMR (400 MHz, DMSO-d$_6$) δ 8.57 (d, J=6.1 Hz, 2H), 8.17 (t, J=5.8 Hz, 1H), 7.87 (s, 1H), 7.83 (d, J=6.1 Hz, 2H), 7.24 (t, J=8.1 Hz, 1H), 6.88-6.90 (s, 2H), 6.81 (dd, J=2.9, 7.9 Hz, 1H), 4.35 (d, J=5.7 Hz, 2H), 3.72 (s, 3H), 3.65 (s, 3H).

HPLC purity 99.49% {t$_R$=7.880 min, Flow 1 ml/min, [(MeOH/(0.1% TFA in H$_2$O):50/50]}; HRMS (ESI+ve) m/z calculated for $C_{18}H_{19}N_4O_2S$ (M+H)$^+$ 355.1223, found 355.1215.

Compound 6a

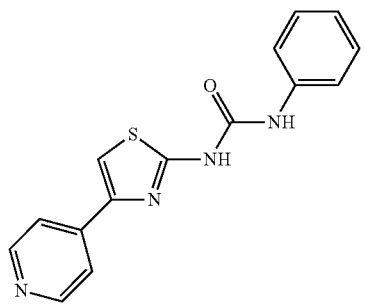 [SMILES: O=C(Nc1ccccc1)Nc1nc(-c2ccncc2)cs1]

1-Phenyl-3-(4-(pyridin-4-yl)thiazol-2-yl)urea

A mixture of 3a (0.081 g, 0.457 mmol), phenyl isocyanate (0.065 g, 0.559 mmol) in anhydrous DMF (0.5 ml), was stirred in a Biotage microwave at 150° C. for 10 min After cooling to room temperature, the solvent was removed under reduced pressure and chromatography on silica gel performed using the FlashMaster 3 purification station afforded 6a as an off white solid (0.072 g, 0.243 mmol, 53%). $^1$H NMR (400 MHz, DMSO-d$_6$) δ 10.77 (bs, 1H), 8.91 (bs, 1H), 8.60 (d, J=6.0 Hz, 2H), 7.90 (s, 1H), 7.81 (d, J=6.1 Hz, 2H), 7.47 (d, J=8.3 Hz, 2H), 7.32 (t, J=7.9 Hz, 2H), 7.04 (t, J=7.4 Hz, 1H); HRMS (ESI+ve) m/z calculated for $C_{15}H_{13}N_4OS$ (M+H)$^+$ 297.0804, found 297.0809.

Compound 6b

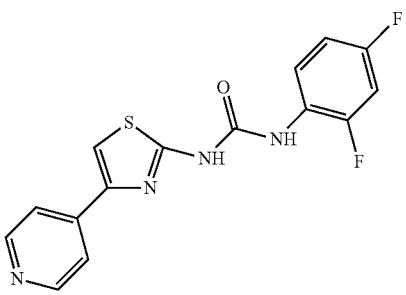 [SMILES: O=C(Nc1nc(-c2ccncc2)cs1)Nc1ccc(F)cc1F]

1-(2,4-Difluorophenyl)-3-(4-(pyridin-4-yl)thiazol-2-yl)urea

This was prepared from 3a (0.096 g, 0.542 mmol), 2,4-difluorophenyl isocyanate (0.168 g, 1.084 mmol) in anhydrous DMF (0.6 ml) in a similar manner as described for 6a. After cooling to room temperature, the solvent was removed under reduced pressure. Chromatography on silica gel performed using the FlashMaster 3 purification station, followed by trituration with DCM afforded 6b as an off white solid (0.045 g, 0.35 mmol, 25%). $^1$H NMR (400 MHz, DMSO-d$_6$) δ 11.05 (s, 1H), 8.89 (s, 1H), 8.60 (d, J=6.0 Hz, 2H), 8.08-8.01

(m, 1H), 7.93 (s, 1H), 7.81 (d, J=6.0 Hz, 2H), 7.38-7.33 (m, 1H), 7.10-7.05 (m, 1H); HRMS (ESI+ve) m/z calculated for $C_{15}H_{11}N_4F_2OS$ (M+H)$^+$ 333.0616, found 333.0618.

Compound 6c

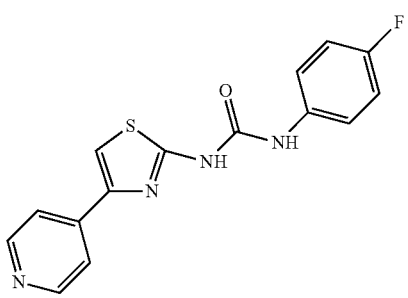 [SMILES: O=C(Nc1ccc(F)cc1)Nc1nc(-c2ccncc2)cs1]

1-(4-Fluorophenyl)-3-(4-(pyridin-4-yl)thiazol-2-yl) urea

A mixture of 3a (0.095 g, 0.536 mmol), 4-fluorophenyl isocyanate (0.147 g, 1.073 mmol) in anhydrous DMF (0.6 ml), was stirred in a Biotage microwave at 150° C. for 20 min After cooling to room temperature, the solvent was removed under reduced pressure and chromatography on silica gel performed using the FlashMaster 3 purification station afforded 6c as an off white solid (0.047 g, 0.149 mmol, 28%). $^1$H NMR (400 MHz, DMSO-d$_6$) δ 10.82 (s, 1H), 8.96 (s, 1H), 8.59 (d, J=6.0 Hz, 2H), 7.91 (s, 1H), 7.81 (d, J=6.0 Hz, 2H), 7.50-7.46 (m, 2H), 7.16 (t, J=8.8 Hz, 2H); HRMS (ESI+ve) m/z calculated for $C_{15}H_{12}N_4FOS$ (M+H)$^+$ 315.0710, found 315.0713.

Compound 6d

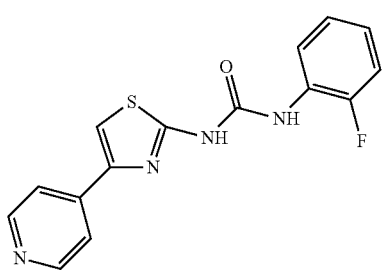 [SMILES: O=C(Nc1nc(-c2ccncc2)cs1)Nc1ccccc1F]

1-(2-Fluorophenyl)-3-(4-(pyridin-4-yl)thiazol-2-yl) urea

A mixture of 3a (0.099 g, 0.559 mmol), 2-fluorophenyl isocyanate (0.153 g, 1.118 mmol) in a similar manner as described for 6c. After cooling to room temperature, the solvent was removed under reduced pressure and chromatography on silica gel performed using the FlashMaster 3 purification station afforded 6d as an off white solid (0.059 g, 0.187 mmol, 34%). $^1$H NMR (400 MHz, DMSO-d$_6$) δ 11.07 (s, 1H), 8.97 (s, 1H), 8.60 (d, J=5.9 Hz, 2H), 8.14-8.09 (m, 1H), 7.93 (s, 1H), 7.82 (d, J=5.8 Hz, 2H), 7.30-7.25 (d, 1H), 7.18 (t, J=7.6 Hz, 1H), 7.08 (m, 1H); HRMS (ESI+ve) m/z calculated for $C_{15}H_{12}N_4FOS$ (M+H)$^+$ 315.0710, found 315.0721.

Compound 6e

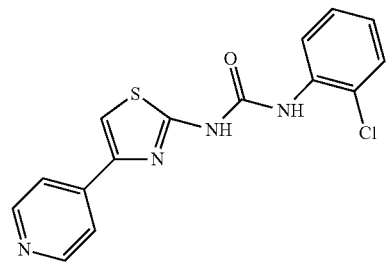 [SMILES: O=C(Nc1nc(-c2ccncc2)cs1)Nc1ccccc1Cl]

1-(2-Chlorophenyl)-3-(4-(pyridin-4-yl)thiazol-2-yl) urea

A mixture of 3a (0.100 g, 0.564 mmol), 2-chlorophenyl isocyanate (0.173 g, 1.129 mmol) in a similar manner as described for 6c. After cooling to room temperature, the solvent was removed under reduced pressure and chromatography on silica gel performed twice using the FlashMaster 3 purification station afforded 6e as an off white solid (0.046 g, 0.139 mmol, 25%). $^1$H NMR (400 MHz, DMSO-d$_6$) δ 11.49 (s, 1H), 8.72 (s, 1H), 8.60 (d, J=5.0 Hz, 2H), 8.16 (d, J=8.2 Hz, 1H), 7.93 (s, 1H), 7.82 (d, J=6.1 Hz, 2H), 7.49 (d, J=8.1 Hz, 1H), 7.33 (t, J=7.8 Hz, 1H), 7.09 (d, J=7.5 Hz, 1H); HRMS (ESI+ve) m/z calculated for $C_{15}H_{11}N_4ClOS$ (M+H)$^+$ 331.0414, found 331.0424.

Compound 9

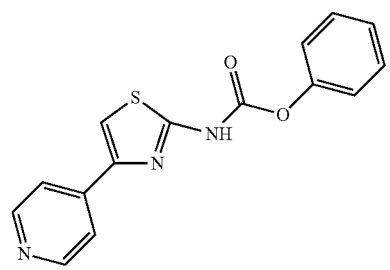 [SMILES: O=C(Nc1nc(-c2ccncc2)cs1)Oc1ccccc1]

Phenyl 4-(pyridin-4-yl)thiazol-2-ylcarbamate

Phenyl chlorophormate (2.10 g, 13.53 mmol) was added dropwise at 0° C., under Argon to a mixture of 3a (1.69 g, 9.59 mmol) in anhydrous pyridine (5 ml) and anhydrous DCM (5 ml) Anhydrous pyridine (4 ml) was then added. After stirring at room temperature for 3 h, the reaction mixture was quenched with sodium bicarbonate (aq. sat. solution). The crude material was extracted twice with DCM. The organic extracts were collected, dried over Na$_2$SO$_4$ and the solvent removed under reduced pressure. The solid residue was trituraturated with hexane/ethyl acetate (8/2, 30 ml), filtered, dried under vacuum. The pure carbamate 9 was obtained as a pale orange solid (2.15 g, 7.23 mmol, 73%). $^1$H NMR (400 MHz, DMSO-d$_6$) δ 12.58 (s, 1H), 8.61 (d, J=6.0 Hz, 2H), 8.02

(s, 1H), 7.82 (d, J=6.1 Hz, 2H), 7.44 (t, J=7.7 Hz, 2H), 7.30 (d, J=6.9 Hz, 2H), 7.27 (t, J=8.6 Hz, 1H).

Compound 1aa

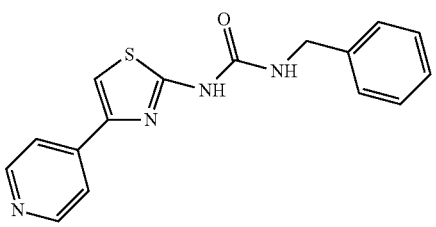 [SMILES: O=C(NCc1ccccc1)Nc1nc(-c2ccncc2)cs1]

1-Benzyl-3-(4-(pyridin-4-yl)thiazol-2-yl)urea

A mixture of 9 (0.110 g, 0.370 mmol), benzylamine (0.043 g, 0.407 mmol) in anhydrous THF (0.5 ml) and CH$_3$CN (0.3 ml) was stirred in a Biotage microwave at 80° C. for 30 min. After cooling to room temperature, the solid precipitate was filtered, washed with a solution ethyl acetate and hexane (1/9), and dried under vacuum to afford pure 1aa as an off white solid (0.079 g, 0.254 mmol, 69%). White solid, $^1$H NMR (400 MHz, DMSO-d$_6$) δ 10.82 (s, 1H), 8.56 (d, 2H, J=5.8), 7.81 (s, 1H), 7.77 (d, 2H, J=5.7), 7.34-7.22 (m, 5H), 7.01 (t, 1H, J=5.6), 4.34 (d, 2H, J=6.0); HPLC purity 99.30% {t$_R$=5.280 min, Flow 1 ml/min, [(CH$_3$CN/(0.1% TFA in H$_2$O):30/70]}; purity 99.31% {t$_R$=17.133 min, Flow 1 ml/min, [(MeOH/(0.1% TFA in H$_2$O):40/60]}; HRMS (ESI+ve) m/z calculated for C$_{16}$H$_{14}$N$_4$OS (M+H)$^+$ 311.0961, found 311.0963.

Compound 1am

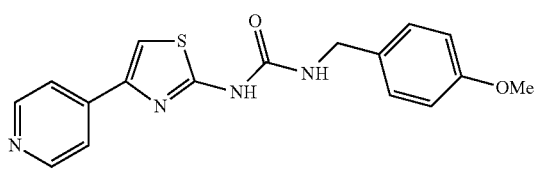 [SMILES: COc1ccc(CNC(=O)Nc2nc(-c3ccncc3)cs2)cc1]

1-(4-Methoxybenzyl)-3-(4-(pyridin-4-yl)thiazol-2-yl)urea

A mixture of 9 (0.102 g, 0.349 mmol), 4-methoxybenzylamine (0.057 g, 0.419 mmol) in anhydrous THF (0.6 ml) was stirred in a CEM microwave under the following conditions: power 150 W, ramp time 2 min, hold time 10 min, temperature 100° C., pressure 220 PSI. After cooling to room temperature, the solid precipitate was filtered, washed with THF, and dried under vacuum to afford pure 1am as an off white solid (0.088 g, 0.258 mmol, 74%). $^1$H NMR (400 MHz, DMSO-d$_6$) δ 10.76 (bs, 1H, disappeared on D$_2$O shake), 8.56 (d, J=6.12, 2H), 7.81 (s, 1H), 7.76 (d, J=6.16, 2H), 7.21 (d, J=8.68 Hz, 2H), 6.91 (bt, J=5.56 Hz, 1H, disappeared on D$_2$O shake), 6.88 (d, J=8.72, 2H), 4.25 (bd, J=5.8, 2H), 3.71 (s, 3H).; HPLC purity 99.15% {t$_R$=5.387 min, Flow 1 ml/min, [(CH$_3$CN/(0.1% TFA in H$_2$O):30/70]}; purity 97.74% {t$_R$=6.087 min, Flow 1 ml/min, [(MeOH/(0.1% TFA in H$_2$O): 50/50]}; HRMS (ESI+ve) m/z calculated for C$_{17}$H$_{17}$N$_4$O$_2$S (M+H)$^+$ 341.1066, found 341.1062.

Compound 1an

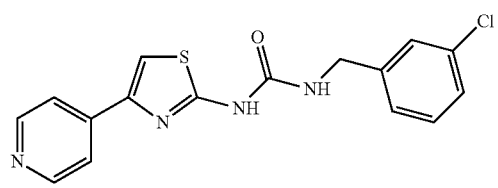 [SMILES: O=C(NCc1cccc(Cl)c1)Nc1nc(-c2ccncc2)cs1]

1-(3-Chlorobenzyl)-3-(4-(pyridin-4-yl)thiazol-2-yl)urea

A mixture of 9 (0.098 g, 0.329 mmol), 3-chlorobenzylamine (0.055 g, 0.395 mmol) in anhydrous THF (0.6 ml) was stirred in a CEM microwave under the following conditions: power 150 W, ramp time 2 min, hold time 20 min, temperature 100° C., pressure 220 PSI. After cooling to room temperature, the solid precipitate was filtered, washed with THF, and dried in vacuo to afford pure 1an as an off white solid (0.061 g, 0.177 mmol, 54%). $^1$H NMR (400 MHz, DMSO-d$_6$) δ 10.93 (bs, 1H, disappeared on D$_2$O shake), 8.57 (d, J=6.16, 2H), 7.82 (s, 1H), 7.77 (d, J=6.20, 2H), 7.38-7.24 (m, 4H), 7.00 (bt, J=5.52 Hz, 1H, disappeared on D$_2$O shake), 4.34 (bd, J=6.00, 2H); $^{13}$C NMR (400 MHz, DMSO-d$_6$) δ 160.96, 154.71, 150.85, 146.81, 143.01, 141.70, 133.67, 130.97, 127.59, 127.51, 126.48, 120.48, 111.80, 43.05; HPLC purity 98.60% {t$_R$=12.073 min, Flow 1 ml/min, [(CH$_3$CN/(0.1% TFA in H$_2$O):30/70]}; purity 97.43% {t$_R$=13.173 min, Flow 1 ml/min, [(MeOH/(0.1% TFA in H$_2$O):50/50]}; HRMS (ESI+ve) m/z calculated for C$_{16}$H$_{14}$N$_4$OSCl (M+H)$^+$ 345.0571, found 345.0573.

Compound 1af

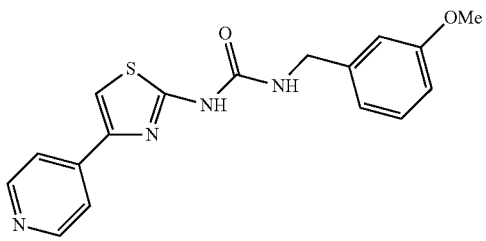 [SMILES: COc1cccc(CNC(=O)Nc2nc(-c3ccncc3)cs2)c1]

1-(3-Methoxybenzyl)-3-(4-(pyridin-4-yl)thiazol-2-yl)urea

This was prepared from 9 (0.112 g, 0.376 mmol), 3-methoxybenzylamine (0.062 g, 0.451 mmol) in the same manner as described for 1an. After cooling to room temperature, ethyl acetate was added followed by hexane. The solid precipitate was filtered, washed with hexane, and dried in vacuo to afford pure 1af as an off white solid (0.081 g, 0.238 mmol, 63%). $^1$H NMR (400 MHz, DMSO-d$_6$) δ 10.82 (s, 1H), 8.57 (d, J=6.0 Hz, 2H), 7.82 (s, 1H), 7.77 (d, J=6.2 Hz, 2H), 7.24 (t, J=8.1 Hz, 1H), 7.00 (t, J=6.0 Hz, 1H), 6.79-6.82 (m, 3H), 4.31 (d, J=5.9 Hz, 1H), 3.72 (s, 3H).); HPLC purity 98.94% {t$_R$=5.667 min, Flow 1 ml/min, [(CH₃CN/(0.1% TFA in H₂O):30/70]}; purity 97.99% {t_R=6.327 min, Flow 1 ml/min, [(MeOH/(0.1% TFA in H₂O):50/50]}; HRMS (ESI+ve) m/z calculated for C₁₇H₁₇N₄O₂S (M+H)⁺ 341.1065, found 341.1066.

Compound 1ah

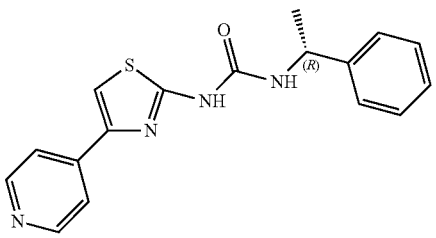

(R)-1-(1-Phenylethyl)-3-(4-(pyridin-4-yl)thiazol-2-yl)urea

This was prepared from 9 (0.142 g, 0.477 mmol) and (R)-(+)-alpha-methylbenzyl amine (0.069 g, 572 mmol) in the same manner as described for 1an. After cooling to room temperature, the solvent was removed under reduced pressure. The obtained solid was slurriee with acetonitrile (4 ml), filtered, washed with acetonitrile (1 ml×2), dried under vacuum to provide pure-1ah as an off white solid (0.104 g, 0320 mmol, 67%). ¹H NMR (400 MHz, DMSO-d₆) δ 10.51 (s, 1H), 8.56 (d, J=5.8 Hz, 2H), 7.80 (s, 1H), 7.76 (d, J=6.0 Hz, 2H), 7.36-7.31 (m, 4H), 7.26-7.24 (m, 1H), 7.02 (d, J=7.7 Hz, 1H), 4.84 (quint, J=7.3 Hz, 1H), 1.40 (d, J=6.9 Hz, 6H); HRMS (ESI+ve) m/z calculated for C₁₇H₁₇N₄OS (M+H)⁺ 325.1117, found 325.1120.

The enantiomeric excess was determined by HPLC using a Chiralcel OJ column [(Iso-propanol/Hexane:50/50), Flow 1 ml/min], t_{R1}=9.117 min, Area % 0.368 (minor), t_{R2}=14.467 min, Area % 94.933 (major).

Compound 1ai

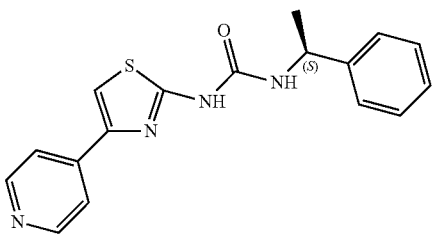

(S)-1-(1-Phenylethyl)-3-(4-(pyridin-4-yl)thiazol-2-yl)urea

This was prepared from 9 (0.164 g, 0.551 mmol) and (S)-(−)-alpha-methylbenzyl amine (0.080 g, 0.661 mmol) in the same manner as described for 1an. After cooling to room temperature, the solvent was removed under reduced pressure. The obtained solid was slurriee with acetonitrile (4 ml), filtered, washed with acetonitrile, dried under vacuum to provide pure 1ai as an off white solid (0.099 g, 0305 mmol, 55%). ¹H NMR (400 MHz, DMSO-d₆) δ 10.52 (s, 1H), 8.57 (d, J=6.0 Hz, 2H), 7.80 (s, 1H), 7.76 (d, J=6.1 Hz, 2H), 7.37-7.32 (m, 4H), 7.27-7.21 (m, 1H), 7.03 (d, J=8.3 Hz, 1H), 4.84 (p, J=6.6 Hz, 1H), 1.41 (d, J=6.9 Hz, 3H); HRMS (ESI+ve) m/z calculated for C₁₇H₁₇N₄OS (M+H)⁺ 3251117, found 325.1119.

The enantiomeric excess was determined by HPLC using a Chiralcel OJ column [(Iso-propanol/Hexane:50/50), Flow 1 ml/min], t_{R1}=9.467 min, Area % 99.243 (major).

Compound 1ab

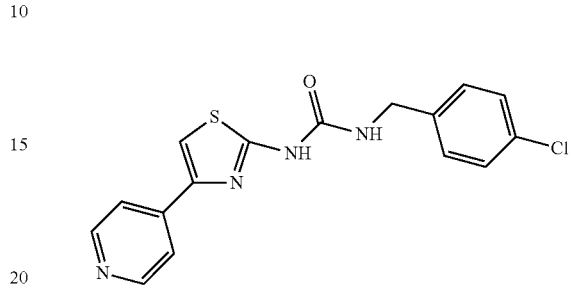

1-(4-Chlorobenzyl)-3-(4-(pyridin-4-yl)thiazol-2-yl)urea

This was prepared from 9 (0.105 g, 0.352 mmol) and 4-chlorobenzyl amine (0.054 g, 0.387 mmol) in the same manner as described for 1an. After cooling to room temperature, the solid precipitate was filtered, washed with THF, and dried in vacuo to afford pure 1ab as an off white solid (0.104 g, 0.301 mmol, 86%). ¹H NMR (DMSO-d₆) δ 10.89 (s, 1H), 8.56 (d, J=6.0 Hz, 2H), 7.81 (s, 1H), 7.77 (d, J=6.1 Hz, 2H), 7.38 (d, J=8.4 Hz, 2H), 7.31 (d, J=8.3 Hz, 2H), 7.04 (t, J=7.0 Hz, 1H), 4.32 (d, J=5.7 Hz, 2H); HPLC purity 99.52% {t_R=11.400 min, Flow 1 ml/min, [(CH₃CN/(0.1% TFA in H₂O):30/70]}; purity 99.22% {t_R=13.607 min, Flow 1 ml/min, [(MeOH/(0.1% TFA in H₂O):50/50]}; HRMS (ESI+ve) m/z calculated for C₁₆H₁₄F₁N₄OS (M+H)⁺ 345.0571, found 345.0570.

Compound 1cq

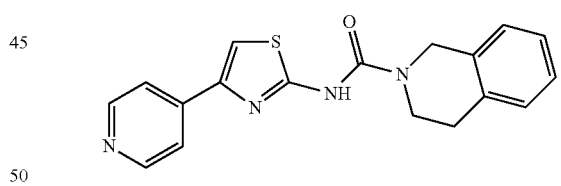

N-(4-(Pyridin-4-yl)thiazol-2-yl)-3,4-dihydroisoquinoline-2(1H)-carboxamide

This was prepared from 9 (0.095 g, 0.319 mmol), 1,2,3,4-tetrahydroisoquinoline (0.051 g, 0.383 mmol)) in the same manner as described for 1an. After cooling to room temperature, the reaction mixture washed with NaOH (aq. 1M) and extracted with DCM. The combined organic extracts were dried over Na₂SO₄ and the solvent removed under reduced pressure. Chromatography on silica gel using a FlashMaster 3 purification station (AcOEt/Hexane) afforded pure 1cq (0.058 g, 0.173 mmol, 54%) as an off white solid ¹H NMR (400 MHz, DMSO-d₆) δ 11.19 (s, 2H, disappeared on D₂O shake), 8.58 (d, J=6.1 Hz, 2H), 7.84 (s, 1H), 7.82 (d, J=6.1 Hz, 2H), 7.18 (s, 4H), 4.69 (s, 2H), 3.76 (t, J=6.0 Hz, 2H), 2.85 (t, J=5.9, 2H). HPLC purity 99.62% {t_R=8.860 min, Flow 1 ml/min, [(CH$_3$CN/(0.1% TFA in H$_2$O):30/70]}; purity 99.55% {$t_R$=12.387 min, Flow 1 ml/min, [(MeOH/(0.1% TFA in H$_2$O):50/50]}; HRMS (ESI+ve) m/z calculated for C$_{18}$H$_{17}$N$_4$OS (M+H)$^+$ 337.1117, found 337.1110.

Compound 1ao

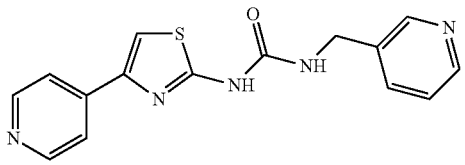 [SMILES: O=C(NCc1cccnc1)Nc1nc(-c2ccncc2)cs1]

1-(Pyridin-3-ylmethyl)-3-(4-(pyridin-4-yl)thiazol-2-yl)urea

This was obtained as an off white solid (0.072 g, 0.231 mmol, 73%) from 9 (0.095 g, 0.319 mmol) and 3-(aminomethyl)pyridine (0.041 g, 0.383 mmol) in the same manner as described for 1an. $^1$H NMR (400 MHz, DMSO-d$_6$) δ 10.91 (s, 1H, disappeared on D$_2$O shake), 8.57 (d, J=6.1 Hz, 2H), 8.52 (d, J=1.6 Hz, 1H), 8.45 (dd, J=1.5, 4.7 Hz, 1H), 7.82 (s, 1H), 7.77 (d, J=6.1 Hz, 2H), 7.70 (dt, J=7.8, 1.8 Hz, 1H), 7.36 (dd, J=4.5, 8.1 Hz, 1H), 7.10 (t, J=6.0 Hz, 1H, disappeared on D$_2$O shake), 4.37 (d, J=6.0 Hz, 2H); HRMS (ESI+ve) m/z calculated for C$_{18}$H$_{17}$N$_4$OS (M+H)$^+$ 312.0913, found 312.0927.

Compound 1ap

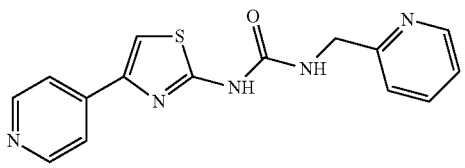 [SMILES: O=C(NCc1ccccn1)Nc1nc(-c2ccncc2)cs1]

1-(Pyridin-2-ylmethyl)-3-(4-(pyridin-4-yl)thiazol-2-yl)urea

This was obtained and as an off white solid (0.065 g, 0.209 mmol, 60%) from 9 (0.104 g, 0.349 mmol) and 2-(aminomethyl)pyridine (0.045 g, 0.419 mmol) in the same manner as described for 1an. $^1$H NMR (400 MHz, DMSO-d$_6$) δ 10.95 (s, 1H, disappeared on D$_2$O shake), 8.57 (d, J=6.1 Hz, 2H), 8.52 (d, J=4.8 Hz, 1H), 7.81 (s, 1H), 7.79 (d, J=6.1 Hz, 2H), 7.76 (dd, J=7.7, 1.8 Hz, 2H), 7.33 (t, J=7.88 Hz, 1H), 7.29-7.26 (m, 2H), 4.46 (d, J=5.6 Hz, 2H); HRMS (ESI+ve) m/z calculated for C$_{18}$H$_{17}$N$_4$OS (M+H)$^+$ 312.0913, found 312.0910.

Compound 1aq

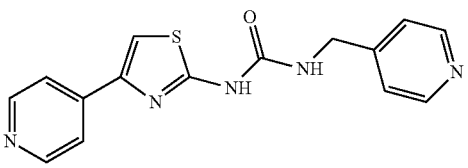 [SMILES: O=C(NCc1ccncc1)Nc1nc(-c2ccncc2)cs1]

1-(4-(Pyridin-4-yl)thiazol-2-yl)-3-(pyridin-4-ylmethyl)urea

This was obtained as an off white solid (0.059 g, 0.189 mmol, 66%) from 9 (0.086 g, 0.288 mmol) and 4-(aminomethyl)pyridine (0.037 g, 0.346 mmol) in the same manner as described for 1an. $^1$H NMR (400 MHz, DMSO-d$_6$) δ 11.02 (s, 1H, disappeared on D$_2$O shake), 8.58 (d, J=6.1 Hz, 2H), 8.50 (d, J=6.0 Hz, 2H), 7.82 (s, 1H), 7.78 (d, J=6.1 Hz, 2H), 7.27 (d, J=6.0 Hz, 2H), 7.13 (t, J=6.0 Hz, 1H, disappeared on D$_2$O shake), 4.38 (d, J=6.1 Hz, 2H); HRMS (ESI+ve) m/z calculated for C$_{18}$H$_{17}$N$_4$OS (M+H)$^+$ 312.0913, found 312.0915.

Compound 1aj

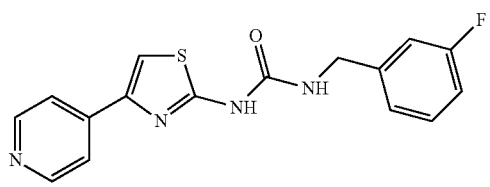 [SMILES: O=C(NCc1cccc(F)c1)Nc1nc(-c2ccncc2)cs1]

1-(3-Fluorobenzyl)-3-(4-(pyridin-4-yl)thiazol-2-yl)urea

This was obtained as an off white solid (0.072 g, 0.129 mmol, 73%) from 9 (0.089 g, 0.299 mmol) and 3-fluorobenzylamine (0.044 g, 0.358 mmol) in the same manner as described for 1an. $^1$H NMR (400 MHz, DMSO-d$_6$) δ 10.90 (s, 1H, disappeared on D$_2$O shake), 8.57 (d, J=6.1 Hz, 2H,), 7.82 (s, 1H), 7.78 (d, J=6.1 Hz, 2H,), 7.39-7.34 (m, 1H), 7.149-7.04 (m, 4H), 4.36 (d, J=6.0 Hz, 2H); HPLC purity 99.21% {$t_R$=6.507 min, Flow 1 ml/min, [(CH$_3$CN/(0.1% TFA in H$_2$O):30/70]}; purity 98.54% {$t_R$=7.107 min, Flow 1 ml/min, [(MeOH/(0.1% TFA in H$_2$O):50/50]}; HRMS (ESI+ve) m/z calculated for C$_{16}$H$_{14}$N$_4$FOS (M+H)$^+$ 329.0866, found 329.0868.

Compound 1ar

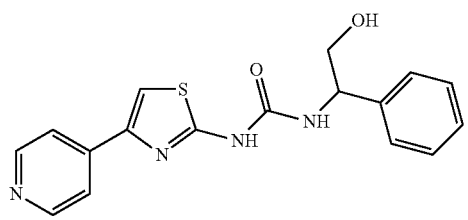 [SMILES: O=C(Nc1nc(-c2ccncc2)cs1)NC(CO)c1ccccc1]

1-(2-Hydroxy-1-phenylethyl)-3-(4-(pyridin-4-yl)thiazol-2-yl)urea

This was obtained as a white solid (0.032 g, 0.094 mmol, 27%) from 9 (0.105 g, 0.352 mmol) and DL-phenylglycinol (0.058 g, 0.423 mmol) in the same manner as described for 1an. $^1$H NMR (400 MHz, DMSO-d$_6$) δ 10.71 (s, 1H), 8.57 (d, J=5.9 Hz, 2H), 7.80 (s, 1H), 7.78 (d, J=6.1 Hz, 2H), 7.28 (m, 6H), 5.08 (t, J=5.1 Hz, 1H), 4.77 (dd, J=5.5, 12.9 Hz, 1H), 3.70-3.63 (m, 1H), 3.58-3.54 (m, 1H HPLC purity 99.82% {$t_R$=9.967 min, Flow 1 ml/min, [(CH$_3$CN/(0.1% TFA in H$_2$O):20/80]}; purity 99.72% {$t_R$=7.967 min, Flow 1 ml/min, [(MeOH/(0.1% TFA in H$_2$O):40/60]}; HRMS (ESI+ve) m/z calculated for C$_{17}$H$_{17}$N$_4$O$_2$S (M+H)$^+$ 341.1066, found 341.1065.

The enantiomeric excess was determined by HPLC using a Chiralcel OJ column [(Iso-propanol/Hexane:70/30), Flow 1 ml/min], $t_{R1}$=5.500 min, Area % 52.583, $t_{R2}$=11.733 min, Area % 46.508.

Compound 1as

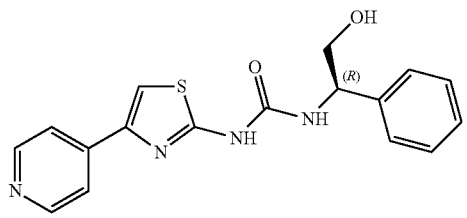

(R)-1-(2-Hydroxy-1-phenylethyl)-3-(4-(pyridin-4-yl)thiazol-2-yl)urea

This was obtained as an off white solid (0.060 g, 0.176 mmol, 39%) from 9 (0.134 g, 0.450 mmol) and (R)-(−)-2-amino-2-phenylethanol (0.074 g, 0.540 mmol) in the same manner as described for 1an. $^1$H NMR (400 MHz, DMSO-$d_6$) δ 10.69 (s, 1H), 8.57 (d, J=6.2 Hz, 2H), 7.80 (s, 1H), 7.78 (d, J=6.1 Hz, 2H), 7.34-7.22 (m, 6H), 5.07 (t, J=5.2 Hz, 1H), 4.77 (dd, J=6.8, 12.1 Hz, 1H), 3.70-3.74 (m, 1H), 3.60-3.54 (m, 1H); $^{13}$C NMR (100 MHz, DMSO-$d_6$) δ 160.87, 154.14, 150.84, 146.78, 141.94, 141.64, 128.87, 127.57, 127.29, 120.50, 111.69, 65.34, 56.01; HPLC purity 99.89% {$t_R$=9.960 min, Flow 1 ml/min, [(CH$_3$CN/(0.1% TFA in H$_2$O):20/80]}; purity 99.84% {$t_R$=7.940 min, Flow 1 ml/min, [(MeOH/(0.1% TFA in H$_2$O):40/60]}; HRMS (ESI+ve) m/z calculated for $C_{17}H_{17}N_4O_2S$ (M+H)$^+$ 341.1066, found 341.1074.

The enantiomeric excess was determined by HPLC using a Chiralcel OJ column [(Iso-propanol/Hexane:70/30), Flow 1 ml/min], $t_{R1}$=5.450 min, Area % 0.516 (minor), $t_{R2}$=11.550 min, Area % 98.547 (major).

Compound 1at

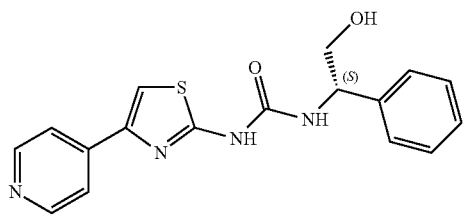

(S)-1-(2-Hydroxy-1-phenylethyl)-3-(4-(pyridin-4-yl)thiazol-2-yl)urea

This was obtained as an off white solid (0.090 g, 0.264 mmol, 55%) from 9 (0.144 g, 0.483 mmol) and (s)-(+)-2-phenylglycinol (0.079 g, 0.580 mmol) in the same manner as described for 1an. $^1$H NMR (400 MHz, DMSO-$d_6$) δ 10.71 (s, 1H), 8.57 (d, J=6.1 Hz, 2H), 7.80 (s, 1H), 7.78 (d, J=6.1 Hz, 2H,), 7.34-7.21 (m, 6H), 5.08 (t, J=5.2 Hz, 1H), 4.77 (dd, J=5.4, 12.4 Hz, 1H), 3.70-3.64 (s, 1H), 3.59-3.54 (m, 1H); HPLC purity 99.93% {$t_R$=9.927 min, Flow 1 ml/min, [(CH$_3$CN/(0.1% TFA in H$_2$O):20/80]}; purity 99.92% {$t_R$=7.893 min, Flow 1 ml/min, [(MeOH/(0.1% TFA in H$_2$O):40/60]}; HRMS (ESI+ve) m/z calculated for $C_{17}H_{17}N_4O_2S$ (M+H)$^+$ 341.1066, found 341.1067. The enantiomeric excess was determined by HPLC using a Chiralcel OJ column [(Iso-propanol/Hexane:70/30), Flow 1 ml/min], $t_{R1}$=5.467 min, Area % 98.777.

Compound 1au

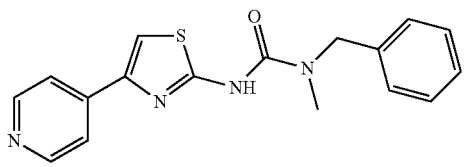 [SMILES: CN(Cc1ccccc1)C(=O)Nc1nc(-c2ccncc2)cs1]

1-Benzyl-1-methyl-3-(4-(pyridin-4-yl)thiazol-2-yl)urea

This was prepared from 9 (0.099 g, 0.332) and N-benzyl-methylamine (0.048 g, 0.399 mmol) in the same manner as described for 1an. After cooling to room temperature, the reaction mixture washed with NaOH (aq. 1M) and extracted with DCM. The combined organic extracts were dried over Na$_2$SO$_4$ and the solvent removed under reduced pressure. Chromatography on silica gel using a FlashMaster 3 purification station (AcOEt/Hexane) afforded pure 1au (0.068 g, 0.209 mmol, 63%) as an off white solid. $^1$H NMR (400 MHz, DMSO-$d_6$) δ 11.08 (s, 1H), 8.57 (d, J=6.1 Hz, 2H), 7.85 (s, 1H), 7.82 (d, J=4.6 Hz, 2H), 7.36-7.32 (m, 2H), 7.27-7.22 (m, 3H), 4.61 (s, 2H), 2.96 (s, 3H); HPLC purity 99.19% {$t_R$=6.787 min, Flow 1 ml/min, [(CH$_3$CN/(0.1% TFA in H$_2$O):30/70]}; purity 97.68% {$t_R$=7.560 min, Flow 1 ml/min, [(MeOH/(0.1% TFA in H$_2$O):50/50]}; HRMS (ESI+ve) m/z calculated for $C_{17}H_{17}N_4OS$ (M+H)$^+$ 325.1117, found 325.1112.

Compound 1av

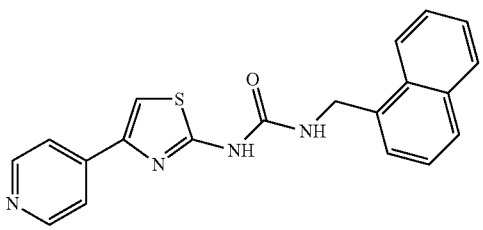 [SMILES: O=C(NCc1cccc2ccccc12)Nc1nc(-c2ccncc2)cs1]

1-(Naphthalen-1-ylmethyl)-3-(4-(pyridin-4-yl)thiazol-2-yl)urea

This was obtained as an off white solid (0.108 g, 0.300 mmol, 68%) from 9 (0.131 g, 0.440 mmol) and 1-naphthyl-methylamine (0.083 g, 0.528 mmol) in the same manner as described for 1an. $^1$H NMR (400 MHz, DMSO-$d_6$) δ 10.74 (s, 1H), 8.56 (d, J=6.1 Hz, 2H), 8.11 (d, J=8.5 Hz, 1H), 7.96 (d, J=7.7 Hz, 2H), 7.87-7.85 (m, 1H), 7.82 (s, 1H), 7.75 (d, J=6.1 Hz, 2H), 7.60-7.52 (m, 2H), 7.49-7.46 (m, 2H), 7.11 (t, J=5.9

Hz, 1H), 4.82 (d, J=5.7 Hz, 1H); HPLC purity 99.36% {$t_R$=16.800 min, Flow 1 ml/min, [(CH$_3$CN/(0.1% TFA in H$_2$O):30/70]}; purity 95.16% {$t_R$=6.467 min, Flow 1 ml/min, [(MeOH/(0.1% TFA in H$_2$O):50/50]}; HRMS (ESI+ve) m/z calculated for C$_{20}$H$_{17}$N$_4$OS (M+H)$^+$ 361.1117, found 361.1114.

Compound 1aw

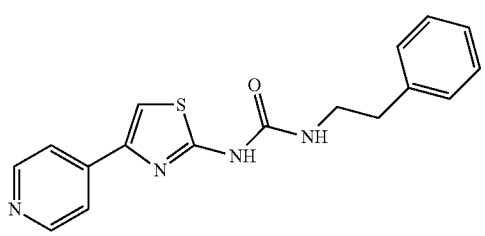 [SMILES: O=C(NCCc1ccccc1)Nc1nc(-c2ccncc2)cs1]

1-Phenethyl-3-(4-(pyridin-4-yl)thiazol-2-yl)urea

This was prepared from 9 (0.157 g, 0.527 mmol) and 2-phenylethylamine (0.076 g, 0.632 mmo) in the same manner as described for 1an. After cooling to room temperature, DCM (3 ml) and Hexane (3 ml) were added to the reaction mixture. The solid precipitate was filtered, dried under vacuum. The pure 1aw was obtained as an off white solid (0.142 g, 0.437 mmol, 83%). $^1$H NMR (400 MHz, DMSO-d$_6$) δ 10.69 (s, 1H), 8.56 (d, J=6.1 Hz, 2H), 7.79 (s, 1H), 7.75 (d, J=6.1 Hz, 2H), 7.30 (t, J=6.6 Hz, 2H), 7.23-7.18 (m, 3H), 6.53 (t, J=3.7 Hz, 1H), 3.38 (q, J=6.4 Hz, 2H), 2.76 (t, J=7.2 Hz, 2H); HPLC purity 98.95% {$t_R$=7.327 min, Flow 1 ml/min, [(CH$_3$CN/(0.1% TFA in H$_2$O):30/70]}; purity 97.38% {$t_R$=9.500 min, Flow 1 ml/min, [(MeOH/(0.1% TFA in H$_2$O): 50/50]}; HRMS (ESI+ve) m/z calculated for C$_{17}$H$_{17}$N$_4$OS (M+H)$^+$ 325.1117, found 325.1113.

Compound 1ax

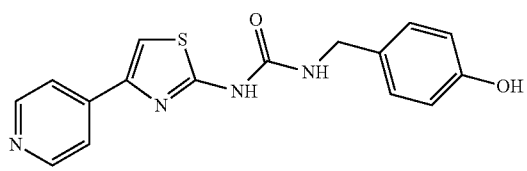 [SMILES: O=C(NCc1ccc(O)cc1)Nc1nc(-c2ccncc2)cs1]

1-(4-Hydroxybenzyl)-3-(4-(pyridin-4-yl)thiazol-2-yl)urea

This was obtained as an off white solid (0.085 g. 0.260 mmol, 74%) from 9 (0.105 g, 0.352 mmol) and 4-hydroxybenzylamine (0.052 g, 0.423 mmol) in the same manner as described for 1an. $^1$H NMR (400 MHz, DMSO-d$_6$) δ 10.68 (s, 1H), 9.31 (s, 1H), 8.56 (d, J=6.1 Hz, 2H), 7.80 (s, 1H), 7.76 (d, J=6.1 Hz, 2H), 7.09 (d, J=8.5 Hz, 2H), 6.87 (t, J=5.4 Hz, 2H), 6.70 (d, J=8.6 Hz, 2H), 4.21 (d, J=5.8 Hz, 2H); HPLC purity 99.70% {$t_R$=6.640 min, Flow 1 ml/min, [(CH$_3$CN/(0.1% TFA in H$_2$O):20/80]}; purity 99.58% {$t_R$=5.287 min, Flow 1 ml/min, [(MeOH/(0.1% TFA in H$_2$O):40/60]}; HRMS (ESI+ve) m/z calculated for C$_{16}$H$_{15}$N$_4$O$_2$S (M+H)$^+$ 327.0910, found 327.0905.

Compound 1ay

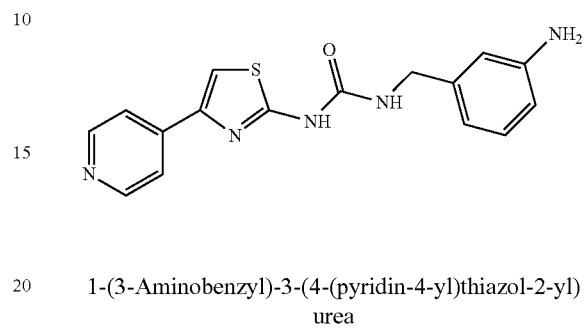

1-(3-Aminobenzyl)-3-(4-(pyridin-4-yl)thiazol-2-yl)urea

This was obtained as an off white solid (0.046 g, 0.141 mmol, 35%) from 9 (0.121 g, 0.406 mmol) and 3-aminobenzylamine (0.122 g, 0.487 mmol) in the same manner as described for 1an. $^1$H NMR (400 MHz, DMSO-d$_6$) δ 10.71 (s, 1H), 8.57 (d, J=6.1 Hz, 2H), 7.81 (s, 1H), 7.77 (d, J=6.1 Hz, 2H), 6.95 (t, J=7.7 Hz, 1H), 6.89 (t, J=5.2 Hz, 1H), 6.47 (s, 1H), 6.42 (t, J=7.0 Hz, 2H), 5.06 (s, 2H), 4.19 (d, J=5.8 Hz, 2H); HRMS (ESI+ve) m/z calculated for C$_{16}$H$_{16}$N$_5$OS (M+H)$^+$ 326.1070, found 326.1063.

Compound 1cr

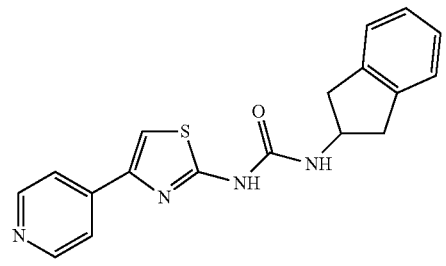 [SMILES: O=C(Nc1nc(-c2ccncc2)cs1)NC1Cc2ccccc2C1]

1-(2,3-Dihydro-1H-inden-2-yl)-3-(4-(pyridin-4-yl)thiazol-2-yl)urea

This was obtained as an off white solid (0.097 g, 0.288 mmol, 80%) from 9 (0.108 g, 0.362 mmol) and 2-aminoindan (0.057 g, 0.435 mmol) in the same manner as described for 1an. $^1$H NMR (400 MHz, DMSO-d$_6$) δ 10.42 (s, 1H), 8.56 (d, J=6.1 Hz, 2H), 7.81 (s, 1H), 7.74 (d, J=6.1 Hz, 2H), 7.25 (d, J=8.6 Hz, 2H), 7.25 (dd, J=3.3, 5.3 Hz, 2H), 6.95 (d, J=6.9 Hz, 1H), 4.45 (m, 1H), 3.21 (dd, J=7.1, 16.0 Hz, 2H), 2.80 (dd, J=5.1, 16.0 Hz, 2H); HPLC purity 99.24% {$t_R$=9.413 min, Flow 1 ml/min, [(CH$_3$CN/(0.1% TFA in H$_2$O):30/70]}; purity 97.83% {$t_R$=13.523 min, Flow 1 ml/min, [(MeOH/(0.1% TFA in H$_2$O):50/50]}; HRMS (ESI+ve) m/z calculated for C$_{16}$H$_{16}$N$_5$OS (M+H)$^+$ 312.0913, found 312.0922.

Compound 1az

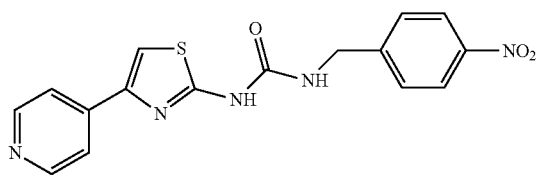 [SMILES: O=C(NCc1ccc([N+](=O)[O-])cc1)Nc1nc(-c2ccncc2)cs1]

1-(4-Nitrobenzyl)-3-(4-(pyridin-4-yl)thiazol-2-yl) urea

This was obtained as yellow solid from 9 (0.126 g, 0.423 mmol) and 4-nitrobenzyl amine (0.095 g, 0.508 mmol) in the same manner as described for 1an. $^1$H NMR (400 MHz, DMSO-$d_6$) δ 10.95 (s, 1H), 8.57 (d, J=6.1 Hz, 2H), 8.20 (d, J=8.7 Hz, 2H), 7.82 (s, 1H), 7.78 (d, J=6.1 Hz, 2H), 7.55 (d, J=8.7 Hz, 2H), 7.20 (t, J=6.0 Hz, 1H), 4.48 (d, J=6.1 Hz, 2H); HPLC purity 99.45% {$t_R$=5.880 min, Flow 1 ml/min, [(CH$_3$CN/(0.1% TFA in H$_2$O):30/70]}; purity 98.23% {$t_R$=5.440 min, Flow 1 ml/min, [(MeOH/(0.1% TFA in H$_2$O): 50/50]}; HRMS (ESI+ve) m/z calculated for $C_{16}H_{14}N_5O_3S$ (M+H)$^+$ 356.0811, found 356.0819.

Compound 1ba

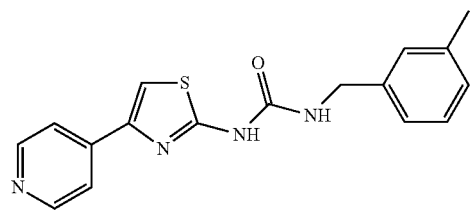 [SMILES: Cc1cccc(CNC(=O)Nc2nc(-c3ccncc3)cs2)c1]

1-(3-Methylbenzyl)-3-(4-(pyridin-4-yl)thiazol-2-yl) urea

This was prepared from 9 (0.111 g, 0.372 mmol) and 3-methyl amine (0.054 g, 0.447 mmol) in the same manner as described for 1an. After cooling to room temperature, THF (1.5-2 ml) and hexane (1.5-2 ml) were added. The solid precipitate was filtered, washed with a solution THF/hexane (1/9, 1 ml), dried under vacuum. The pure 1ba was obtained as a white solid (0.0.071 g, 0.219 mmol, 59%). $^1$H NMR (400 MHz, DMSO-$d_6$) δ 10.78 (s, 1H), 8.57 (d, J=6.1 Hz, 2H), 7.81 (s, 1H), 7.77 (d, J=6.1 Hz, 2H), 7.21 (t, J=7.5 Hz, 2H), 7.09-7.04 (m, 3H), 6.98 (t, J=5.4 Hz, 1H), 4.30 (d, J=5.9 Hz, 2H), 2.27 (s, 3H); HPLC purity 97.73% {$t_R$=11.627 min, Flow 1 ml/min, [(MeOH/(0.1% TFA in H$_2$O):50/50]}; HRMS (ESI+ve) m/z calculated for $C_{16}H_{14}N_5O_3S$ (M+H)$^+$ 325.1117, found 325.1104.

Compound 1bb

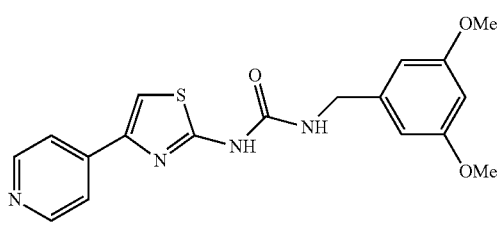 [SMILES: COc1cc(CNC(=O)Nc2nc(-c3ccncc3)cs2)cc(OC)c1]

1-(3,5-Dimethoxybenzyl)-3-(4-(pyridin-4-yl)thiazol-2-yl)urea

This was obtained as a white solid (0.114 g, 0.308 mmol, 83%) from 9 (0.110 g, 0.369 mmol) and 3,5-dimethoxybenzyl amine (0.074 g, 0.443 mmol) in the same manner as described for 1an. $^1$H NMR (400 MHz, DMSO-$d_6$) δ 10.78 (s, 1H), 8.57 (d, J=6.1 Hz, 2H), 7.82 (s, 1H), 7.77 (d, J=6.1 Hz, 2H), 6.99 (t, J=6.4 Hz, 2H), 6.45 (d, J=2.3 Hz, 2H), 6.37 (t, J=2.2 Hz, 1H), 4.27 (d, J=5.9 Hz, 2H), 3.70 (s, 6H); HPLC purity 99.39% {$t_R$=7.227 min, Flow 1 ml/min, [(MeOH/(0.1% TFA in H$_2$O):50/50]}; HRMS (ESI+ve) m/z calculated for $C_{18}H_{19}N_4O_3S$ (M+H)$^+$ 371.1172, found 371.1163.

Compound 1bc

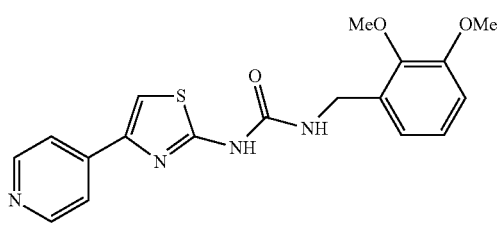 [SMILES: COc1cccc(CNC(=O)Nc2nc(-c3ccncc3)cs2)c1OC]

1-(2,3-Dimethoxybenzyl)-3-(4-(pyridin-4-yl)thiazol-2-yl)urea

This was obtained as an off white solid (0.101 g, 0.279 mmol, 78%) from 9 (0.104 g, 0.349 mmol) and 2,3-dimethoxybenzyl amine (0.070 g, 0.419 mmol) in the same manner as described for 1an. $^1$H NMR (400 MHz, DMSO-$d_6$) δ 10.75 (s, 1H), 8.57 (d, J=6.1 Hz, 2H), 7.81 (s, 1H), 7.77 (d, J=6.1 Hz, 2H), 7.04-7.00 (m, 1H), 6.96 (dd, J=1.6, 8.2 Hz, 1H), 6.90 (t, J=5.6 Hz, 1H), 6.83 (dd, J=1.6, 7.6 Hz, 1H), 4.32 (d, J=5.9 Hz, 2H), 3.78 (s, 3H), 3.75 (s, 3H); HPLC purity 99.38% {$t_R$=6.200 min, Flow 1 ml/min, [(MeOH/(0.1% TFA in H$_2$O):50/50]}; HRMS (ESI+ve) m/z calculated for $C_{18}H_{19}N_4O_3S$ (M+H)$^+$ 371.1172, found 371.1161.

Compound 1bd

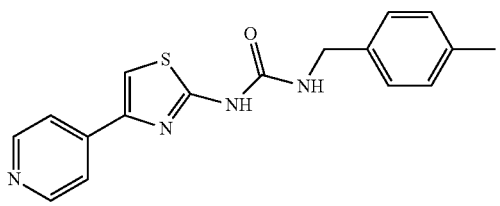 [SMILES: Cc1ccc(CNC(=O)Nc2nc(-c3ccncc3)cs2)cc1]

1-(4-Methylbenzyl)-3-(4-(pyridin-4-yl)thiazol-2-yl)urea

This was obtained as a off white solid (0.082 g, 0.250 mmol, 77%) from 9 (0.097 g, 0.325 mmol) and 4-methylbenzyl amine (0.047 g, 0.391 mmol) in the same manner as described for 1an. $^1$H NMR (400 MHz, DMSO-$d_6$) δ 10.78 (s, 1H), 8.57 (d, J=6.2 Hz, 2H), 7.81 (s, 1H), 7.77 (d, J=6.2 Hz, 2H), 7.18 (d, J=8.1 Hz, 2H), 7.13 (d, J=8.0 Hz, 2H), 6.95 (t, J=6.0 Hz, 1H), 4.29 (d, J=5.9 Hz, 2H), 2.26 (s, 3H); HPLC purity 98.46% {$t_R$=11.707 min, Flow 1 ml/min, [(MeOH/(0.1% TFA in H$_2$O):50/50]}; HRMS (ESI+ve) m/z calculated for $C_{17}H_{17}N_4OS$ (M+H)$^+$ 325.1117, found 325.1110.

Compound 1be

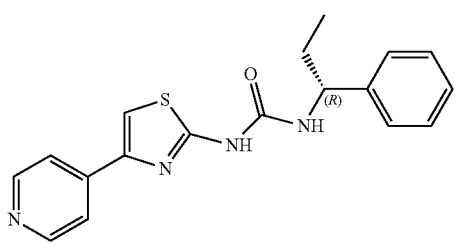

(R)-1-(1-Phenylpropyl)-3-(4-(pyridin-4-yl)thiazol-2-yl)urea

This was prepared from 9 (0.107 g, 0.359 mmol) and (R)-(+)-1-phenylpropylamine (0.071 g, 0.431 mmol) in the same manner as described for 1an. After cooling to room temperature, the reaction mixture washed with NaOH (2M, aq., 5 ml) and extracted with DCM (2×10 ml). The combined organic extracts were dried over Na$_2$SO$_4$ and the solvent removed under reduced pressure. The remaining solid was triturated with diethyl ether, filtered, and dried under vacuum. The pure 1be obtained as a white solid (0.045 g, 0.133 mmol, 37%). $^1$H NMR (400 MHz, DMSO-$d_6$) δ 8.57 (d, J=6.0 Hz, 2H), 7.80 (s, 1H), 7.76 (d, J=6.0 Hz, 2H), 7.35-7.28 (m, 4H,), 7.26-7.21 (m, 1H), 7.04 (d, J=7.4 Hz, 1H), 4.65-4.58 (m, 1H), 1.76-1.79 (m, 2H), 0.83 (t, J=7.3 Hz); HPLC purity 99.20% {$t_R$=14.480 min, Flow 1 ml/min, [(MeOH/(0.1% TFA in H$_2$O):50/50]}; HRMS (ESI+ve) m/z calculated for $C_{18}H_{19}N_4OS$ (M+H)$^+$ 339.1274, found 339.1272.

The enantiomeric excess was determined by HPLC using a Chiralcel OJ column [(Iso-propanol/Hexane:30/70), Flow 1 ml/min], $t_{R1}$=16.600 min, Area % 99.196.

Compound 1bf

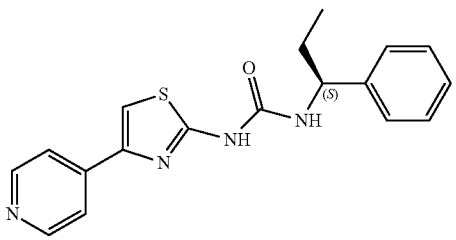

(S)-1-(1-Phenylpropyl)-3-(4-(pyridin-4-yl)thiazol-2-yl)urea

This was prepared from 9 (0.111 g, 0.372 mmol) and (S)-(−)-1-phenylpropylamine (0.073 g, 0.447 mmol) in the same manner as described for 1an. After cooling to room temperature, the reaction mixture washed with NaOH (2M, aq., 5 ml) and extracted with DCM (2×10 ml). The combined organic extracts were dried over Na$_2$SO$_4$ and the solvent removed under reduced pressure. The remaining solid was triturated with diethyl ether, filtered, and dried under vacuum. The pure 1bf obtained as a white solid (0.082 g, 0.242 mmol, 65%). $^1$H NMR (400 MHz, DMSO-$d_6$) δ 8.57 (d, J=6.2 Hz, 2H), 7.80 (s, 1H), 7.77 (d, J=6.1 Hz, 2H), 7.32-7.29 (m, 4H), 7.26-7.21 (m, 1H), 7.04 (d, J=6.7 Hz, 1H), 4.65-4.59 (m, 1H), 1.77-1.79 (m, 2H), 0.83 (t, J=7.3 Hz, 3H); HPLC purity 99.32% {$t_R$=14.467 min, Flow 1 ml/min, [(MeOH/(0.1% TFA in H$_2$O):50/50]}; HRMS (ESI+ve) m/z calculated for $C_{18}H_{19}N_4OS$ (M+H)$^+$ 339.1274, found 339.1273.

The enantiomeric excess was determined by HPLC using a Chiralcel OJ column [(Iso-propanol/Hexane:30/70), Flow 1 ml/min], $t_{R1}$=13.1333 min, Area % 99.317.

Compound 1bg

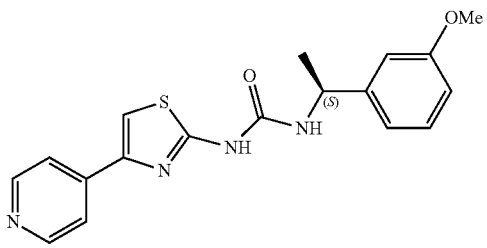

(S)-1-(1-(3-Methoxyphenyl)ethyl)-3-(4-(pyridin-4-yl)thiazol-2-yl)urea

This was prepared from 9 (0.109 g, 0.359 mmol) and (S)-(−)-1-(3-methoxylphenyl)ethylamine (0.065 g, 0.431 mmol) in the same manner as described for 1an. After cooling to room temperature, the solvent was removed under reduced pressure. The remaining solid was triturated diethyl ether, filtered and dried under vacuum. The pure 1bg was obtained as a white solid (0.069 g, 0.194 mmol, 54%). $^1$H NMR (400 MHz, DMSO-d$_6$) δ 10.52 (s, 1H), 8.57 (d, J=6.0 Hz, 2H), 7.80 (s, 1H), 7.76 (d, J=6.1 Hz, 2H), 7.25 (t, J=7.9 Hz, 1H), 7.02 (d, J=8.3 Hz, 1H), 6.90-6.88 (m, 2H), 6.81 (dd, J=2.2, 8.5 Hz, 1H), 4.80 (q, J=6.4 Hz, 1H), 1.39 (d, J=6.9 Hz, 3H); $^{13}$C NMR (400 MHz, DMSO-d$_6$) δ 160.79, 160.03, 153.70, 150.85, 146.75, 146.73, 141.64, 130.25, 120.47, 118.59, 112.77, 112.37, 111.74, 55.69, 49.71, 23.60. HPLC purity 99.73% {t$_R$=7.900 min, Flow 1 ml/min, [(CH$_3$CN/(0.1% TFA in H$_2$O):30/70]}; purity 96.33% {t$_R$=9.240 min, Flow 1 ml/min, [(MeOH/(0.1% TFA in H$_2$O):50/50]}; HRMS (ESI+ve) m/z calculated for C$_{18}$H$_{19}$N$_4$O$_2$S (M+H)$^+$ 355.1223, found 355.1216.

The enantiomeric excess was determined by HPLC using a Chiralcel OJ column [(Iso-propanol/Hexane:40/60), Flow 1 ml/min], t$_{R1}$=15.400 min, Area % 96.320.

Compound 1bh

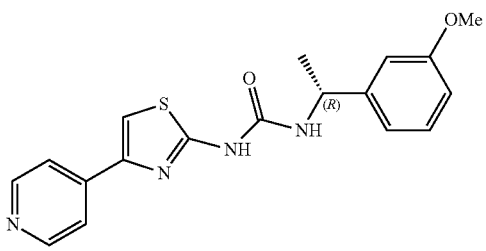

(R)-1-(1-(3-Methoxyphenyl)ethyl)-3-(4-(pyridin-4-yl)thiazol-2-yl)urea

This was prepared from 9 (0.100 g, 0.336 mmol) and (R)-(+)-1-(3-methoxylphenyl)ethylamine (0.060 g, 0.403 mmol) in the same manner as described for 1an. After cooling to room temperature, the solvent was removed under reduced pressure. The remaining solid was triturated diethyl ether, filtered and dried under vacuum. The pure 1bh was obtained as a white solid (0.060 g, 0.169 mmol, 50%). $^1$H NMR (400 MHz, DMSO-d$_6$) δ 10.51 (s, 1H), 8.57 (d, J=6.1 Hz, 2H), 7.80 (s, 1H), 7.76 (d, J=6.1 Hz, 2H), 7.25 (t, J=7.8 Hz, 1H), 7.02 (d, J=7.6 Hz, 1H), 6.90-6.88 (m, 2H), 6.81 (dd, J=2.0, 7.9 Hz, 1H), 4.80 (q, J=7.1 Hz, 1H), 1.39 (d, J=6.9 Hz, 3H); HPLC purity 99.92% {t$_R$=7.913 min, Flow 1 ml/min, [(CH$_3$CN/(0.1% TFA in H$_2$O):30/70]}; purity 96.84% {t$_R$=9.127 min, Flow 1 ml/min, [(MeOH/(0.1% TFA in H$_2$O):50/50]}; HRMS (ESI+ve) m/z calculated for C$_{18}$H$_{19}$N$_4$O$_2$S (M+H)$^+$ 355.1223, found 355.1220.

The enantiomeric excess was determined by HPLC using a Chiralcel OJ column [(Iso-propanol/Hexane:40/60), Flow 1 ml/min], t$_{R1}$=24.700 min, Area % 97.373.

Compound 1bi

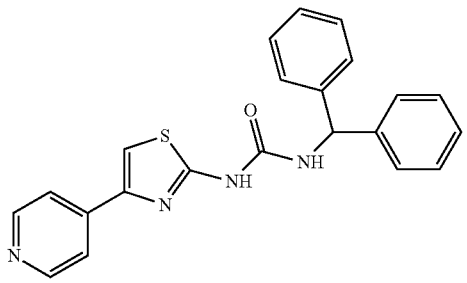 [SMILES: O=C(Nc1nc(-c2ccncc2)cs1)NC(c1ccccc1)c1ccccc1]

1-Benzhydryl-3-(4-(pyridin-4-yl)thiazol-2-yl)urea

This was prepared from 9 (0.131 g, 0.440 mmol) and aminodiphenylmethane (0.096 g, 0.528 mmol) in the same manner as described for 1an. The solid precipitate was filtered, dried under vacuum. The organic solution was concentrated to dryness and the remaining solid was triturated with a solution of THF/Hexane (2/1, 3 ml), filtered, dried under vacuum. The two batches were combined and pure 1bi was obtained as a white solid (0.114 g, 0.295 mmol, 67%). $^1$H NMR (400 MHz, DMSO-d$_6$) δ 10.52 (s, 1H), 8.57 (d, J=6.1 Hz, 2H), 7.83 (s, 1H), 7.76 (d, J=6.1 Hz, 2H), 7. (d, J=7.7 Hz, 1H), 7.37-7.27 (m, 8H), 7.26 (m, 2H), 5.99 (d, J=8.1 Hz, 1H); HPLC purity 99.91% {t$_R$=8.453 min, Flow 1 ml/min, [(MeOH/(0.1% TFA in H$_2$O):50/50]}; HRMS (ESI+ve) m/z calculated for C$_{18}$H$_{19}$N$_4$O$_2$S (M+H)$^+$ 387.1274, found 387.1264.

Compound 12a

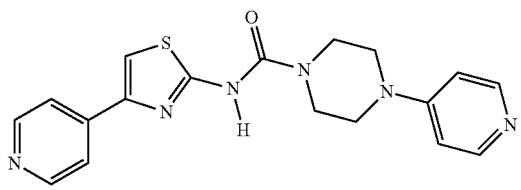 [SMILES: O=C(Nc1nc(-c2ccncc2)cs1)N1CCN(c2ccncc2)CC1]

4-(Pyridin-4-yl)-N-(4-(pyridin-4-yl)thiazol-2-yl) piperazine-1-carboxamide

This was prepared from 9 (0.096 g, 0.332 mmol) and 1-(pyridin-4-yl)piperazine (0.052 g, 0.322 mmol) in the same manner as described for 1an. After cooling to room temperature, the solid precipitate was filtered, and dried under vacuum. The pure 12a was obtained as an off white solid (0.080 g, 0.219 mmol, 66%). $^1$H NMR (400 MHz, DMSO-d$_6$) δ 11.23 (s, 1H), 8.59 (d, J=6.1 Hz, 2H), 8.16 (d, J=6.5 Hz, 2H), 7.85 (s, 1H), 7.82 (d, J=6.1 Hz, 2H), 6.85 (d, J=6.6 Hz, 2H), 3.66 (t, J=5.1 Hz, 4H), 3.39 (t, J=5.1 Hz, 4H). HRMS (ESI+ve) m/z calculated for C$_{18}$H$_{19}$N$_6$OS (M+H)$^+$ 367.1335, found 367.1334.

Compound 12b

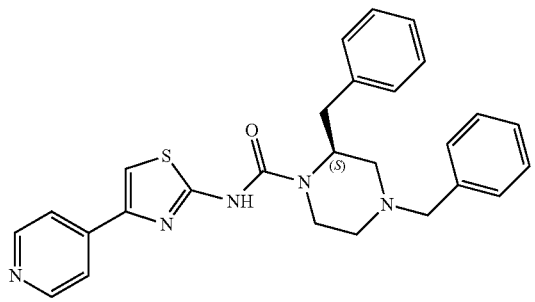

(S)-2,4-Dibenzyl-N-(4-(pyridin-4-yl)thiazol-2-yl)piperazine-1-carboxamide

This was prepared from 9 (0.047 g, 0.161 mmol) and (S)-1,3-dibenzylpiperazine (0.049 g, 0.161 mmol) in the same manner as described for 1an. After cooling to room temperature, the reaction mixture washed with NaOH (2M, aq., 5 ml) and extracted with DCM (2×10 ml). The combined organic extracts were dried over $Na_2SO_4$ and the solvent removed under reduced pressure. The remaining solid was triturated with MeOH, filtered, and dried under vacuum. The pure 12b was obtained as a white solid (0.024 g, 0.051 mmol, 32%). $^1$H NMR (400 MHz, CDCl$_3$) δ 8.57 (s, J=Hz, 2H), 8.00 (s, 1H), 7.57 (d, J=6.2 Hz, 2H), 7.32-7.23 (m, 5H), 7.16-7.12 (m, 2H), 7.07-7.03 (m, 3H), 4.09 (s, 1H), 3.86 (s, 1H), 3.50 (d, J=7.6 Hz, 1H), 3.42 (d, J=5.0 Hz, 1H), 3.35 (d, J=12.9 Hz, 1H), 3.08-3.05 (m, 1H), 2.90-2.87 (m, 1H), 2.72 (d, J=12.8 Hz, 1H), 2.09 (td, J=3.6, 12.1 Hz, 1H), 2.00 (dd, J=3.7, 11.3 HZ, 1H); HPLC purity 98.51% {t$_R$=5.380 min, Flow 1 ml/min, [(MeOH/(0.1% TFA in H$_2$O):60/40]}; HRMS (ESI+ve) m/z calculated for $C_{18}H_{24}N_5O_2S$ (M+H)$^+$ 470.2009, found 470.2011.

Compound 1bj

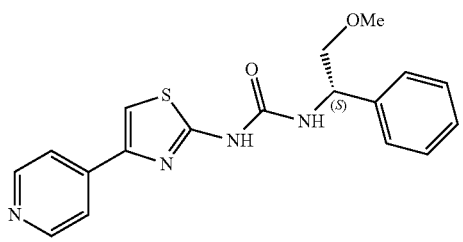

(S)-1-(2-Methoxy-1-phenylethyl)-3-(4-(pyridin-4-yl)thiazol-2-yl)urea

This was prepared from 9 (0.119 g, 0.339 mmol) and (S)-(+)-1-Amino-1-phenyl-2-methoxyethane (0.075 g, 0.479 mmol) in the same manner as described for 1an. After cooling to room temperature, the solvent was removed under reduced pressure. The remaining solid was triturated diethyl ether, filtered and dried under vacuum. The pure 1bj was obtained as a white solid (0.084 g, 0.236 mmol, 70%). $^1$H NMR (400 MHz, DMSO-d$_6$) δ 10.66 (s, 1H), 8.57 (d, J=6.1 Hz, 2H), 7.81 (s, 1H), 7.78 (d, J=6.1 Hz, 2H), 7.34-7.30 (m, 5H), 7.24-7.22 (m, 1H), 4.96-7.91 (m, 1H,), 3.58 (d, J=5.4 Hz, 2H,), 3.26 (s, 3H); $^{13}$C NMR (100 MHz, DMSO-d$_6$) δ 160.82, 154.00, 150.85, 146.81, 141.61, 141.37, 128.96, 127.76, 127.24, 120.48, 111.73, 75.74, 59.00, 53.59; HPLC purity 99.35% {t$_R$=5.827 min, Flow 1 ml/min, [(CH$_3$CN/(0.1% TFA in H$_2$O):30/70]}; HRMS (ESI+ve) m/z calculated for $C_{18}H_{18}N_4O_2S$ (M+H)$^+$ 354.1223, found 354.1222.

Compound 1bk

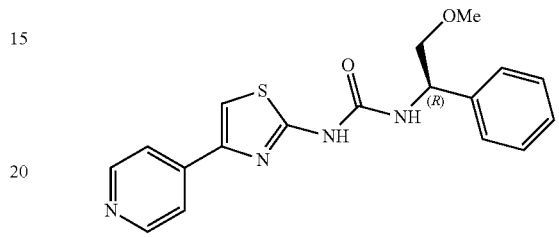

(R)-1-(2-Methoxy-1-phenylethyl)-3-(4-(pyridin-4-yl)thiazol-2-yl)urea

This was prepared from 9 (0.113 g, 0.379 mmol) and (R)-(−)-1-Amino-1-phenyl-2-methoxyethane (0.068 g, 0.455 mmol) in the same manner as described for 1an. After cooling to room temperature, the solvent was removed under reduced pressure. The remaining solid was triturated diethyl ether, filtered and dried under vacuum. The pure 1bk was obtained as a white solid (0.079 g, 0.223 mmol, 59%). $^1$H NMR (400 MHz, DMSO-d$_6$) δ 10.66 (s, 2H), 8.57 (d, J=6.1 Hz, 2H,), 7.81 (s, 1H), 7.78 (d, J=6.1 Hz, 2H), 7.37-7.30 (m, 5H), 7.28-7.22 (m, 1H), 4.96-4.89 (m, 1H), 3.58 (d, J=5.2 Hz, 2H), 3.26 (s, 3H); HPLC purity 98.90% {t$_R$=5.820 min, Flow 1 ml/min, [(CH$_3$CN/(0.1% TFA in H$_2$O):30/70]}; HRMS (ESI+ve) m/z calculated for $C_{18}H_{19}N_4O_2S$ (M+H)$^1$ 355.1223, found 355.1226.

Compound 1bl

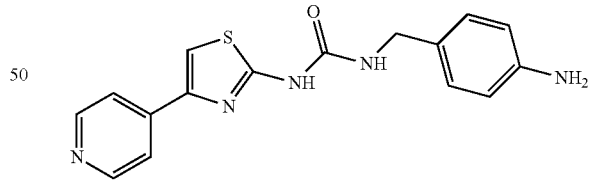

1-(4-Aminobenzyl)-3-(4-(pyridin-4-yl)thiazol-2-yl)urea

This was prepared from 9 (0.097 g, 0.325 mmol) and 4-aminobenzyl amine (0.043 g, 0.358 mmol) in the same manner as described for 1an. After cooling to room temperature, the solid precipitate was filtered and dried under vacuum. The pure 1bl was obtained as a white solid (0.053 g, 0.163 mmol, 50%). $^1$H NMR (400 MHz, DMSO-d$_6$) δ 10.63 (s, 1H), 8.56 (d, J=6.2 Hz, 2H), 7.81 (s, 1H), 7.76 (d, J=6.1 Hz, 2H), 6.95 (d, J=8.4 Hz, 2H), 6.76 (bs, 1H), 6.50 (d, J=8.4 Hz, 2H), 5.00 (bs, 2H), 4.14 (d, J=5.7 Hz, 2H); HRMS (ESI+ve) m/z calculated for $C_{16}H_{16}N_5OS$ (M+H)$^+$ 326.1070, found 326.1070.

Compound 1bm

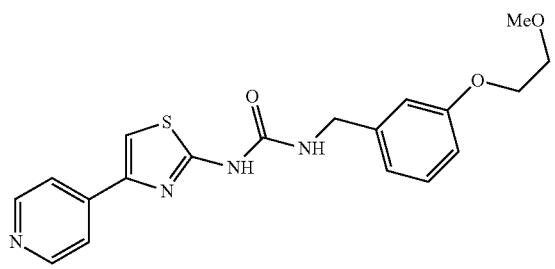 [SMILES: COCCOc1cccc(CNC(=O)Nc2nc(-c3ccncc3)cs2)c1]

1-(3-(2-Methoxyethoxy)benzyl)-3-(4-(pyridin-4-yl)thiazol-2-yl)urea

This was prepared from 9 (0.097 g, 0.325 mmol) and 1-[3-(2-methoxyethoxyl)phenyl]methanamine (0.043 g, 0.358 mmol) in the same manner as described for 1an. After cooling to room temperature, the reaction mixture washed with NaOH (2M, aq., 5 ml) and extracted with DCM (2×10 ml). The combined organic extracts were dried over $Na_2SO_4$ and the solvent removed under reduced pressure. The remaining solid was triturated with diethyl ether, filtered, and dried under vacuum. The pure 1bm was obtained as a white solid (0.053 g, 0.163 mmol, 50%). $^1$H NMR (400 MHz, DMSO-d$_6$) δ 10.88 (s, 1H), 8.57 (d, J=6.0 Hz, 2H), 7.81 (s, 1H), 7.78 (d, J=6.1 Hz, 2H), 7.23 (t, J=8.0 Hz, 1H), 7.07 (s, 1H), 6.86-6.80 (m, 3H), 4.31 (d, J=5.9 Hz, 2H), 4.05 (t, J=4.6 Hz, 2H), 3.62 (t, J=4.5 Hz, 2H), 3.28 (s, 3H); HRMS (ESI+ve) m/z calculated for $C_{19}H_{21}N_4O_3S$ (M+H)$^+$ 385.1328, found 385.1332.

Compound 1bn

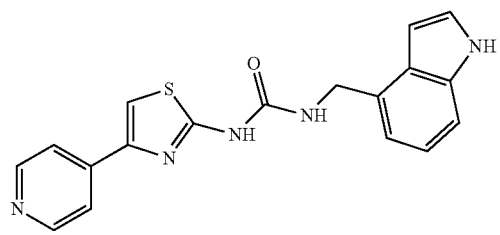 [SMILES: O=C(NCc1cccc2[nH]ccc12)Nc1nc(-c2ccncc2)cs1]

1-((1H-indol-4-yl)methyl)-3-(4-(pyridin-4-yl)thiazol-2-yl)urea

This was prepared from 9 (0.103 g, 0.346 mmol) and 4-aminomethylindole (0.055 g, 0.376 mmol) in the same manner as described for 1an. After cooling to room temperature, the solid precipitate was filtered and dried under vacuum. The pure 1bn was obtained as a white solid (0.099 g, 0.283 mmol, 82%). $^1$H NMR (400 MHz, DMSO-d$_6$) 11.17 (s, 1H), 10.63 (s, 1H), 8.56 (d, J=6.1 Hz, 2H), 7.81 (s, 1H), 7.75 (d, J=6.2 Hz, 2H), 7.35 (t, J=2.8 Hz, 1H), 7.31 (d, J=8.1 Hz, 1H), 7.05 (t, J=7.7 Hz, 1H), 6.97 (bs, 1H), 6.92 (d, J=7.2 Hz, 1H), 6.52-6.51 (m, 1H), 4.59 (d, J=5.7 Hz, 2H,), HPLC purity 98.50% {$t_R$=4.307 min, Flow 1 ml/min, [(MeOH/(0.1% TFA in $H_2O$):50/50]}; HRMS (ESI+ve) m/z calculated for $C_{18}H_{16}N_5OS$ (M+H)$^+$ 350.1070, found 350.1069.

Compound 1bo

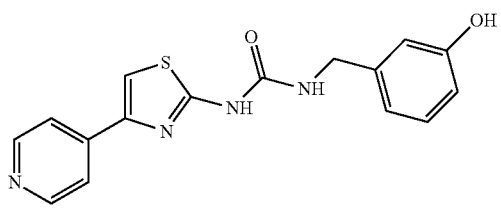 [SMILES: O=C(NCc1cccc(O)c1)Nc1nc(-c2ccncc2)cs1]

1-(3-Hydroxybenzyl)-3-(4-(pyridin-4-yl)thiazol-2-yl)urea

This was prepared from 9 (0.099 g, 0.332 mmol), 3-hydroxybenzyl amine (0.078 g, 0.365 mmol), and $Et_3N$ (0.1 ml) in the same manner as described for 1an. After cooling to room temperature, the solid precipitate was filtered, washed with water, and dried under vacuum. The pure 1bo was obtained as a white solid (0.064 g, 0.196 mmol, 59%). $^1$H NMR (400 MHz, DMSO-d$_6$) δ 9.37 (s, 1H), 8.57 (d, J=6.1 Hz, 2H), 7.82 (s, 1H), 7.77 (d, J=6.2 Hz, 2H), 7.11 (t, J=8.0 Hz, 1H), 6.96 (s, 1H), 6.70-6.68 (m, 2H), 6.63-6.60 (m, 1H), 4.26 (d, J=5.9 Hz, 2H); $^{13}$C NMR (100 MHz, DMSO-d$_6$) δ 160.66, 153.21, 150.84, 48.20, 146.67, 141.65, 128.83, 126.90, 125.39, 120.47, 111.50, 55.46, 30.13; HPLC purity 99.82% {$t_R$=8.513 min, Flow 1 ml/min, [(CH$_3$CN/(0.1% TFA in $H_2O$):20/80]}; purity 99.83% {$t_R$=6.727 min, Flow 1 ml/min, [(MeOH/(0.1% TFA in $H_2O$):40/60]}; HRMS (ESI+ve) m/z calculated for $C_{16}H_{15}N_4O_2S$ (M+H)$^+$ 327.0910, found 327.0909.

Compound 1bp

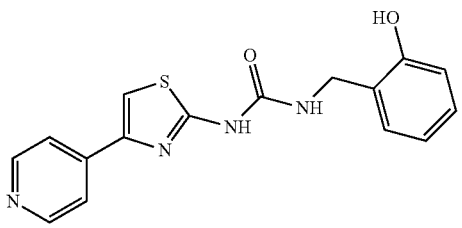 [SMILES: O=C(NCc1ccccc1O)Nc1nc(-c2ccncc2)cs1]

1-(2-Hydroxybenzyl)-3-(4-(pyridin-4-yl)thiazol-2-yl)urea

This was prepared from 9 (0.103 g, 0.346 mmol) and 2-hydroxybenzyl amine (0.042 g, 0.346 mmol) in the same manner as described for 1an. After cooling to room temperature, the solid precipitate was filtered, and dried under vacuum. The pure 1bp was obtained as a white solid (0.087 g, 0.266 mmol, 77%). $^1$H NMR (400 MHz, DMSO-d$_6$) δ 10.75 (s, 1H), 9.65 (s, 1H), 8.57 (d, J=6.1 Hz, 2H), 7.80 (s, 1H), 7.77 (d, J=6.2 Hz, 2H,), 7.13 (dd, J=1.6, 7.4 Hz, 1H), 7.09-7.05 (m, 1H), 6.90 (s, 1H), 6.82-6.80 (m, 1H), 6.76-6.73 (m, 1H), 4.26

(d, J=6.0 Hz, 2H); HRMS (ESI+ve) m/z calculated for $C_{16}H_{15}N_4O_2S$ (M+H)$^+$ 327.0910, found 327.0910.

Compound 1bq

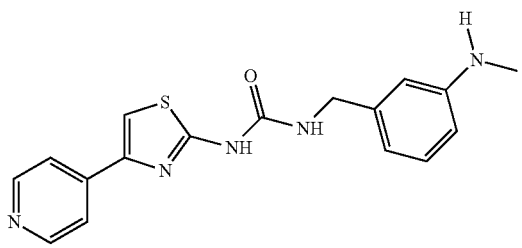 [SMILES: CNc1cccc(CNC(=O)Nc2nc(-c3ccncc3)cs2)c1]

1-(3-(Methylamino)benzyl)-3-(4-(pyridin-4-yl)thiazol-2-yl)urea

This was prepared from 9 (0.096 g, 0.322 mmol) and N-[3-(aminomethyl)phenyl]-N-methylamine (0.048 g, 0.354 mmol) in the same manner as described for 1an. After cooling to room temperature, the solvent was removed under reduced pressure. The remaining solid was triturated diethyl ether, filtered and dried under vacuum. The pure 1bq was obtained as a white solid (0.084 g, 0.247 mmol, 77%). $^1$H NMR (400 MHz, DMSO-d$_6$) δ 8.57 (d, J=6.2 Hz, 2H), 7.81 (s, 1H), 7.77 (d, J=6.1 Hz, 2H), 7.03 (t, J=8.0 Hz, 2H), 6.89 (s, 1H), 6.46-6.44 (m, 2H), 6.41-6.38 (m, 1H), 5.65 (q, J=5.0 Hz, 1H), 4.22 (d, J=5.9 Hz, 2H), 2.63 (d, J=5.1 Hz, 3H); HRMS (ESI+ve) m/z calculated for $C_{17}H_{18}N_5OS$ (M+H)$^+$ 340.1226, found 340.1228.

Compound 1br

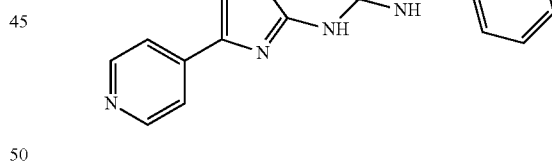

1-(4-(Pyridin-4-yl)thiazol-2-yl)-3-(3-(trifluoromethoxy)benzyl)urea

This was prepared from 9 (0.097 g, 0.325 mmol) and 3-(trifluoromethoxy)benzylamine (0.068 g, 0.358 mmol) in the same manner as described for 1an. After cooling to room temperature, the solvent was removed under reduced pressure. The remaining solid was triturated diethyl ether, filtered and dried under vacuum. The pure 1br was obtained as a white solid (0.098 g, 0.248 mmol, 76%). $^1$H NMR (400 MHz, DMSO-d$_6$) δ 10.88 (s, 1H), 8.57 (d, J=6.1 Hz, 2H), 7.82 (s, 1H), 7.78 (d, J=6.1 Hz, 2H), 7.47 (t, J=7.9 Hz, 1H), 7.33 (d, J=7.8 Hz, 1H), 7.28 (s, 1H), 7.24 (d, J=7.2 Hz, 1H), 7.12 (t, J=6.2 Hz, 1H), 4.39 (d, J=6.0 Hz, 2H); HRMS (ESI+ve) m/z calculated for $C_{17}H_{14}F_3N_4O_2S$ (M+H)$^+$ 395.0784, found 395.0789.

Compound 1bs

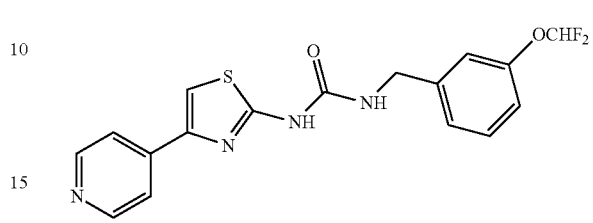

1-(3-(Difluoromethoxy)benzyl)-3-(4-(pyridin-4-yl)thiazol-2-yl)urea

This was prepared from 9 (0.096 g, 0.322 mmol) and 3-(difluoromethoxy)benzylamine (0.061 g, 0.354 mmol) in the same manner as described for 1an. After cooling to room temperature, the solvent was removed under reduced pressure. The remaining solid was triturated diethyl ether, filtered and dried under vacuum. The pure 1bs was obtained as a white solid (0.085 g, 0.224 mmol, 69%). $^1$H NMR (400 MHz, DMSO-d$_6$) δ 10.88 (s, 1H), 8.57 (d, J=6.1 Hz, 2H), 7.82 (s, 1H), 7.78 (d, J=6.2 Hz, 2H), 7.39 (t, J=7.9 Hz, 1H), 0.21 (t, J=74.1 Hz, 1H), 7.17 (d, J=6.9 Hz, 1H), 7.09-7.04 (m, 3H), 4.36 (d, J=6.0 Hz, 2H); HRMS (ESI+ve) m/z calculated for $C_{17}H_{15}F_2N_4O_2S$ (M+H)$^+$ 377.0878, found 377.0879.

Compound 1bt 1-(2-Methylbenzyl)-3-(4-(pyridin-4-yl)thiazol-2-yl)urea

This was prepared from 9 (0.086 g, 0.288 mmol) and 2-methylbenzyl amine (0.038 g, 0.317 mmol) in the same manner as described for 1an (Method C). After cooling to room temperature, the solvent was removed under reduced pressure. The remaining solid was triturated diethyl ether, filtered and dried under vacuum. The pure 1bt was obtained as a white solid (0.045 g, 0.138 mmol, 48%). $^1$H NMR (400 MHz, DMSO-d$_6$) δ 10.19 (s, 1H), 8.57 (d, J=6.0 Hz, 2H), 7.81 (s, 1H), 7.77 (d, J=6.0 Hz, 2H), 7.23-7.21 (m, 1H), 7.16-7.14 (m, 3H), 6.93 (bs, 1H), 4.33 (d, J=5.8 Hz, 2H), 2.28 (s, 3H); HRMS (ESI+ve) m/z calculated for $C_{17}H_{17}N_4OS$ (M+H)$^+$ 325.1117, found 325.1117.

Compound 1bu

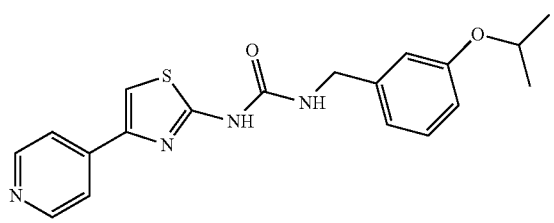 [SMILES: CC(C)Oc1cccc(CNC(=O)Nc2nc(-c3ccncc3)cs2)c1]

1-(3-Isopropoxybenzyl)-3-(4-(pyridin-4-yl)thiazol-2-yl)urea

This was prepared from 9 (0.053 g, 0.178 mmol) and 3-isopropylbenzyl amine (0.035 g, 0.213 mmol) in the same manner as described for 1an. After cooling to room temperature, the solvent was removed under reduced pressure. The remaining solid was triturated diethyl ether, filtered and dried under vacuum. The pure 1bu was obtained as a white solid (0.055 g, 0.149 mmol, 84%). $^1$H NMR (400 MHz, DMSO-$d_6$) δ 10.68 (s, 1H), 8.57 (d, J=6.1 Hz, 2H), 7.82 (s, 1H), 7.77 (d, J=6.1 Hz, 2H), 7.21 (t, J=8.0 Hz, 1H), 6.99 (s, 1H), 6.82-6.77 (m, 3H), 4.60-4.45 (m, 1H), 4.30 (d, J=5.9 Hz, 2H), 1.23 (d, J=6.0 Hz, 6H); HPLC purity 99.83% {$t_R$=14.883 min, Flow 1 ml/min, [(CH$_3$CN/(0.1% TFA in H$_2$O):30/70]}; purity 97.71% {$t_R$=15.867 min, Flow 1 ml/min, [(MeOH/(0.1% TFA in H$_2$O):50/50]}; HRMS (ESI+ve) m/z calculated for C$_{19}$H$_{21}$N$_4$O$_2$S (M+H)$^+$369.1379, found 369.1388.

Compound 1bv

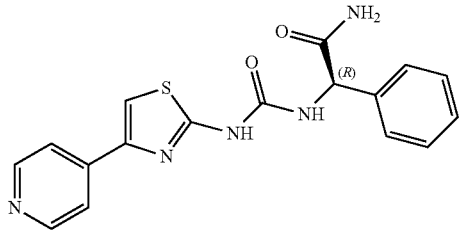

(R)-2-Phenyl-2-(3-(4-(pyridin-4-yl)thiazol-2-yl)ureido)acetamide

A mixture of 9 (0.108 g, 0.362 mmol), D(−)-phenylglycinamide (0.065 g, 0.435 mmol) in anhydrous THF (0.5 ml) was stirred in a CEM microwave under the following conditions: power 150 W, ramp time 2 min, hold time 40 min, temperature 100° C., pressure 220 PSI. After cooling to room temperature, the solid precipitate was filtered, washed with THF, and dried in vacuo, triturated with acetone, filtered, and dried under vacuum to afford pure 1bv as an off white solid (0.070 g, 0.198 mmol, 55%). $^1$H NMR (400 MHz, DMSO-$d_6$) δ 10.77 (s, 1H), 8.57 (d, J=6.0 Hz, 2H), 7.85 (s, 1H), 7.81 (s, 1H), 7.79 (d, J=6.1 Hz, 2H), 7.66 (s, 1H), 7.41 (d, J=7.2 Hz, 2H), 7.35 (t, J=7.5 Hz, 2H), 7.29-7.25 (m, 2H), 5.29 (d, J=7.5 Hz, 1H); HRMS (ESI+ve) m/z calculated for C$_{17}$H$_{16}$N$_5$O$_2$S (M+H)$^+$ 354.1019, found 354.1022.

Compound 1bw

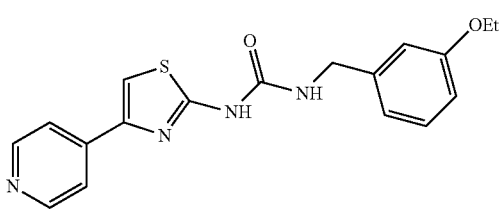 [SMILES: CCOc1cccc(CNC(=O)Nc2nc(-c3ccncc3)cs2)c1]

1-(3-ethoxybenzyl)-3-(4-(pyridin-4-yl)thiazol-2-yl) urea

This was prepared from 9 (0.075 g, 0.0.252 mmol) and 3-ethoxybenzyl amine (0.045 g, 0.302 mmol) in the same manner as described for 1an. After cooling to room temperature, the solvent was removed under reduced pressure. The remaining solid was triturated with ether, filtered, washed with ether, and dried under vacuum. The pure 1bw was obtained as an off white solid (0.078 g, 0.220 mmol, 87%). $^1$H NMR (400 MHz, DMSO-$d_6$) δ 10.47 (s, 1H), 8.57 (d, J=6.1 Hz, 2H), 7.82 (s, 1H), 7.77 (d, J=6.1 Hz, 2H), 7.22 (t, J=8.1 Hz, 1H), 7.00 (t, J=6.4 Hz, 1H), 6.85-6.83 (m, 2H), 6.80-6.78 (m, 1H), 4.31 (d, J=5.8 Hz, 2H), 3.99 (q, J=7.0 Hz, 2H), 1.29 (t, J=7.0 Hz, 3H). HPLC purity 99.48% {$t_R$=9.587 min, Flow 1 ml/min, [(CH$_3$CN/(0.1% TFA in H$_2$O):30/70]}; purity 99.18% {$t_R$=10.741 min, Flow 1 ml/min, [(MeOH/(0.1% TFA in H$_2$O):50/50]}; HRMS (ESI+ve) m/z calculated for C$_{18}$H$_{18}$N$_4$O$_2$S (M+H)$^+$ 355.1223, found 355.1221.

Compound 1bx

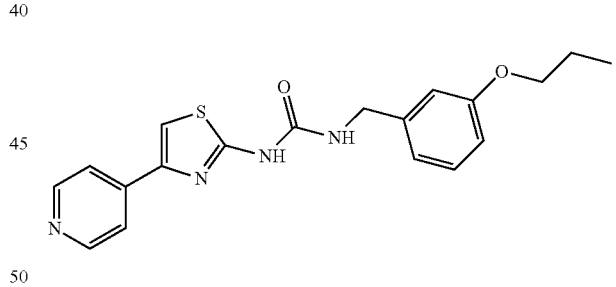

1-(3-propoxybenzyl)-3-(4-(pyridin-4-yl)thiazol-2-yl) urea

This was prepared from 9 (0.101 g, 0.339 mmol) and 3-propoxybenzyl amine (0.082 g, 0.407 mmol), in presence of DIPEA (0.080 ml) in the same manner as described for 1an. After cooling to room temperature, the reaction mixture washed with NaOH (1M, aq.) and extracted with DCM. The combined organic extracts were dried over Na$_2$SO$_4$ and the solvent removed under reduced pressure. The remaining solid was triturated with diethyl ether, filtered, and dried under vacuum. The pure 1bx was obtained as a white solid (0.100 g, 0.261 mmol, 80%). $^1$H NMR (400 MHz, DMSO-$d_6$) δ 11.08 (s, 1H), 8.57 (d, J=6.1 Hz, 2H), 7.85 (s, 1H), 7.82 (d, J=4.6 Hz, 2H), 7.36-7.32 (m, 2H), 7.27-7.22 (m, 3H), 4.61 (s, 2H), 2.96 (s, 3H); HPLC purity 99.94% {$t_R$=5.047 min, Flow 1 ml/min,

[(CH₃CN/(0.1% TFA in H₂O):40/60]}; purity 99.36% {$t_R$=7.093 min, Flow 1 ml/min, [(MeOH/(0.1% TFA in H₂O): 60/40]}; HRMS (ESI+ve) m/z calculated for $C_{19}H_{20}N_4O_2S$ (M+H)⁺ 369.1379, found 369.1377.

Compound 1by

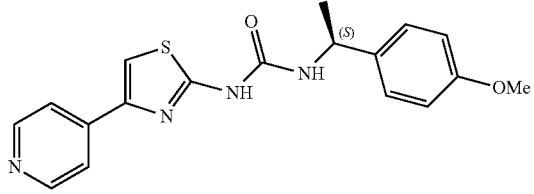

(S)-1-(1-(4-methoxyphenyl)ethyl)-3-(4-(pyridin-4-yl)thiazol-2-yl)urea

This was prepared from 9 (0.089 g, 0.299 mmol) and (S)-1-(4-methoxyphenyl)ethanamine (0.054 g, 0.358 mmol) in the same manner as described for 1an. After cooling to room temperature, the solvent was removed under reduced pressure. The remaining solid was triturated with ether, filtered, washed with ether, and dried under vacuum. The pure 1by was obtained as an off white solid (0.095 g, 0.268 mmol, 90%). ¹H NMR (400 MHz, DMSO-d₆) δ 10.48 (s, 1H), 8.57 (d, J=6.0 Hz, 2H), 7.80 (s, 1H), 7.76 (d, J=6.0 Hz, 2H), 7.25 (d, J=8.6 Hz, 2H), 6.93 (d, J=8.8 Hz, 1H), 6.90 (d, J=8.6 Hz, 2H), 4.79 (p, J=7.0 Hz, 1H), 3.71 (s, 3H), 1.38 (d, J=6.9 Hz, 3H), HPLC purity 99.42% {$t_R$=7.713 min, Flow 1 ml/min, [(CH₃CN/(0.1% TFA in H₂O):30/70]}; purity 99.29% {$t_R$=8.747 min, Flow 1 ml/min, [(MeOH/(0.1% TFA in H₂O): 50/50]}; HRMS (ESI+ve) m/z calculated for $C_{18}H_{18}N_4O_2S$ (M+H)⁺ 355.1223, found 355.1232.

Compound 1bz

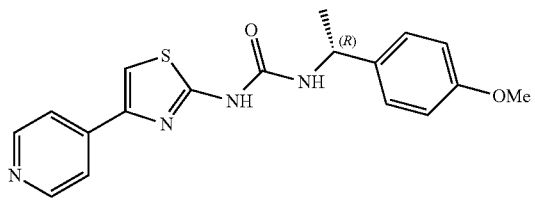

(R)-1-(1-(4-methoxyphenyl)ethyl)-3-(4-(pyridin-4-yl)thiazol-2-yl)urea

This was prepared from 9 (0.092 g, 0.309 mmol) and (R)-1-(4-methoxyphenyl)ethanamine (0.056 g, 0.370 mmol) in the same manner as described for 1an. After cooling to room temperature, the solvent was removed under reduced pressure. The remaining solid was triturated with ether, filtered, washed with ether, and dried under vacuum. The pure 1bz was obtained as an off white solid (0.088 g, 0.248 mmol, 80%). ¹H NMR (400 MHz, DMSO-d₆) δ 10.46 (s, 1H), 8.56 (d, J=6.1 Hz, 2H), 7.80 (s, 1H), 7.76 (d, J=6.1 Hz, 2H), 7.25 (d, J=8.7 Hz, 2H), 6.93 (d, J=8.7 Hz, 1H), 6.89 (d, J=8.7 Hz, 2H), 4.82-4.74 (m, 1H), 3.70 (s, 3H), 1.38 (d, J=6.9 Hz, 3H) HPLC purity 99.49% {$t_R$=7.667 min, Flow 1 ml/min,

[(CH₃CN/(0.1% TFA in H₂O):30/70]}; purity 98.93% {$t_R$=8.647 min, Flow 1 ml/min, [(MeOH/(0.1% TFA in H₂O): 50/50]}; HRMS (ESI+ve) m/z calculated for $C_{18}H_{18}N_4O_2S$ (M+H)⁺ 355.1223, found 355.1234.

Compound 1ca

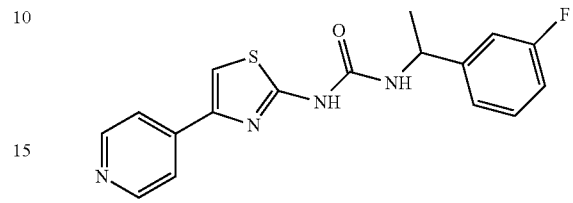

1-(1-(3-fluorophenyl)ethyl)-3-(4-(pyridin-4-yl)thiazol-2-yl)urea

This was prepared from 9 (0.089 g, 0.299 mmol) and 1-(3-fluorophenyl)ethanamine (0.049 g, 0.358 mmol) in the same manner as described for 1an. After cooling to room temperature, the solvent was removed under reduced pressure. The remaining solid was triturated with ether, filtered, washed with hexane, and dried under vacuum. The pure 1ca was obtained as an off white solid (0.085 g, 0.248 mmol, 83%). ¹H NMR (400 MHz, DMSO-d₆) δ 10.57 (s, 1H), 8.57 (d, J=6.1 HZ, 2H), 7.80 (s, 1H), 7.77 (d, J=6.2 Hz, 2H), 7.40-7.32 (m, 1H), 7.18-7.15 (m, 2H), 7.11 (d, J=7.2 Hz, 1H), 7.06 (m, 1H), 4.86 (p, J=7.2 Hz, 1H), 1.40 (d, J=7.0 Hz, 3H); HPLC purity 96.45% {$t_R$=9.380 min, Flow 1 ml/min, [(CH₃CN/(0.1% TFA in H₂O):30/70]}; purity 96.30% {$t_R$=10.053 min, Flow 1 ml/min, [(MeOH/(0.1% TFA in H₂O):50/50]}; HRMS (ESI+ve) m/z calculated for $C_{17}H_{15}N_4FOS$ (M+H)⁺ 343.1023, found 343.1024.

Compound 1cb

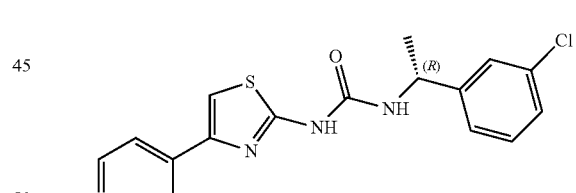

(R)-1-(1-(3-chlorophenyl)ethyl)-3-(4-(pyridin-4-yl)thiazol-2-yl)urea

This was prepared from 9 (0.090 g, 0.302 mmol) and (R)-1-(3-chlorophenyl)ethanamine (0.056 g, 0.362 mmol) in the same manner as described for 1an. After storing the reaction mixture at −20° C. overnight, the solid precipitate was filtered, washed with ether, hexane, and dried under vacuum. The pure 1cb was obtained as a white solid (0.070 g, 0.195 mmol, 65%). ¹H NMR (400 MHz, DMSO-d₆) δ 10.57 (s, 1H), 8.57 (d, J=6.1 Hz, 2H), 7.81 (s, 1H), 7.77 (d, J=6.1 Hz, 2H), 7.40-7.35 (m, 2H), 7.31-7.29 (m, 2H), 7.10 (d, J=6.4 Hz, 1H), 4.87-7.80 (m, 1H), 1.40 (d, J=7.0 Hz, 3H); HPLC purity 99.68% {$t_R$=16.027 min, Flow 1 ml/min, [(CH₃CN/(0.1%

TFA in H$_2$O):30/70]}; purity 99.72% {t$_R$=18.667 min, Flow 1 ml/min, [(MeOH/(0.1% TFA in H$_2$O):50/50]}; HRMS (ESI+ve) m/z calculated for C$_{17}$H$_{15}$ClN$_4$OS (M+H)$^+$ 359.0727, found 359.0726.

Compound 1cc

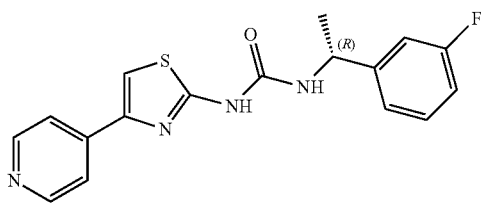

(R)-1-(1-(3-fluorophenyl)ethyl)-3-(4-(pyridin-4-yl)thiazol-2-yl)urea

This was prepared from 9 (0.095 g, 0.319 mmol) and (R)-1-(3-fluorophenyl)ethanamine (0.053 g, 0.389 mmol) in the same manner as described for 1an. After cooling to room temperature, the solvent was removed under reduced pressure. The remaining solid was triturated with ether, filtered, washed with hexane, and dried under vacuum. The pure 1cc was obtained as an off white solid (0.090 g, 0.263 mmol, 83%). $^1$H NMR (400 MHz, DMSO-d$_6$) δ 10.58 (s, 1H), 8.57 (d, J=6.1 Hz, 2H), 7.81 (s, 1H), 7.77 (d, J=6.1 Hz, 2H), 7.40-7.33 (m, 1H), 7.18-7.15 (m, 2H,), 7.12 (bs, 1H), 7.08-7.03 (m, 1H), 4.87-7.81 (m, 1H), 1.40 (d, J=7.0 Hz, 3H), HPLC purity 98.67% {t$_R$=9.360 min, Flow 1 ml/min, [(CH$_3$CN/(0.1% TFA in H$_2$O):30/70]}; purity 98.68% {t$_R$=10.100 min, Flow 1 ml/min, [(MeOH/(0.1% TFA in H$_2$O):50/50]}; HRMS (ESI+ve) m/z calculated for C$_{17}$H$_{15}$N$_4$FOS (M+H)$^+$ 343.1023, found 343.1023.

Compound 1cd

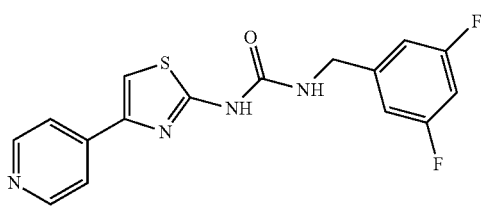 [SMILES: O=C(NCc1cc(F)cc(F)c1)Nc1nc(-c2ccncc2)cs1]

1-(3,5-difluorobenzyl)-3-(4-(pyridin-4-yl)thiazol-2-yl)urea

This was prepared from 9 (0.090 g, 0.302 mmol) and 3,5-difluorobenzyl amine (0.051 g, 0.362 mmol) in the same manner as described for 1an. After cooling to room temperature, the solvent was removed under reduced pressure. The remaining solid was triturated with ether, filtered, washed with hexane, and dried under vacuum. The pure 1cd was obtained as an off white solid (0.079 g, 0.228 mmol, 75%). $^1$H NMR (400 MHz, DMSO-d$_6$) δ 10.97 (s, 1H), 8.57 (d, J=6.2 Hz, 2H), 7.82 (s, 1H), 7.78 (d, J=6.1 Hz, 2H), 7.14-7.07 (m, 2H), 7.01-6.99 (m, 2H), 4.36 (d, J=6.0 Hz, 2H), HPLC purity 98.88% {t$_R$=8.513 min, Flow 1 ml/min, [(CH$_3$CN/(0.1% TFA in H$_2$O):30/70]}; purity 98.68% {t$_R$=9.613 min, Flow 1 ml/min, [(MeOH/(0.1% TFA in H$_2$O):50/50]}; HRMS (ESI+ve) m/z calculated for C$_{16}$H$_{12}$N$_4$F$_4$OS (M+H)$^+$ 347.0772, found 347.077.

Compound 1ce

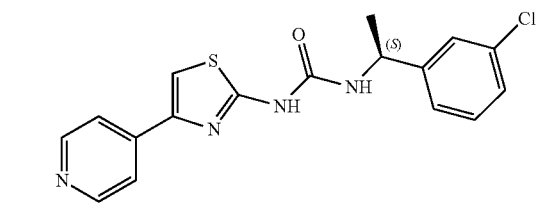

(S)-1-(1-(3-chlorophenyl)ethyl)-3-(4-(pyridin-4-yl)thiazol-2-yl)urea

This was prepared from 9 (0.093 g, 0.312 mmol) and (S)-1-(3-chlorophenyl)ethanamine (0.057 g, 0.364 mmol) in the same manner as described for 1an. After cooling to room temperature, the solvent was removed under reduced pressure. The remaining solid was triturated with ether, filtered, washed with hexane, and dried under vacuum. The pure 1ce was obtained as an off white solid (0.045 g, 0.125 mmol, 40%). $^1$H NMR (400 MHz, DMSO-d$_6$) δ 10.58 (s, 1H), 8.57 (d, J=6.0 Hz, 2H), 7.80 (s, 1H), 7.77 (d, J=6.1 Hz, 2H), 7.40-7.35 (m, 2H), 7.31-7.28 (m, 2H), 7.10 (d, J=8.7 Hz, 1H), 4.88-7.80 (m, 1H), 1.40 (d, J=7.0 Hz, 3H), HPLC purity 99.45% {t$_R$=16.020 min, Flow 1 ml/min, [(CH$_3$CN/(0.1% TFA in H$_2$O):30/70]}; purity 99.47% {t$_R$=18.660 min, Flow 1 ml/min, [(MeOH/(0.1% TFA in H$_2$O):50/50]}; HRMS (ESI+ve) m/z calculated for C$_{17}$H$_{15}$ClN$_4$OS (M+H)$^+$ 359.0727, found 359.0724.

Compound 1cf

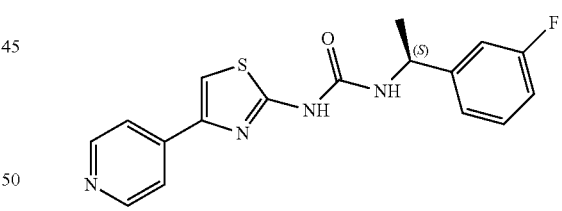

(S)-1-(1-(3-fluorophenyl)ethyl)-3-(4-(pyridin-4-yl)thiazol-2-yl)urea

This was prepared from 9 (0.093 g, 0.312 mmol) and (S)-1-(3-fluorophenyl)ethanamine (0.050 g, 0.359 mmol) in the same manner as described for 1an. After cooling to room temperature, the solvent was removed under reduced pressure. The remaining solid was triturated with ether, filtered, washed with hexane, and dried under vacuum. The pure 1cf was obtained as an off white solid (0.085 g, 0.244 mmol, 78%). $^1$H NMR (400 MHz, DMSO-d$_6$) δ 10.56 (s, 1H), 8.57 (d, J=6.1 Hz, 2H), 7.80 (s, 1H), 7.77 (d, J=6.1 Hz, 2H), 7.40-7.34 (m, 1H), 7.18-7.15 (m, 2H), 7.09-7.03 (s, 2H), 4.90-7.83 (m, 1H), 1.41 (d, J=7.0 Hz, 3H); HPLC purity 98.43% {$t_R$=9.400 min, Flow 1 ml/min, [(CH$_3$CN/(0.1% TFA in H$_2$O):30/70]}; purity 98.40% {$t_R$=10.120 min, Flow 1 ml/min, [(MeOH/(0.1% TFA in H$_2$O):50/50]}; HRMS (ESI+ve) m/z calculated for C$_{17}$H$_{15}$N$_4$FOS (M+H)$^+$ 343.1023, found 343.1051.

Compound 1cg

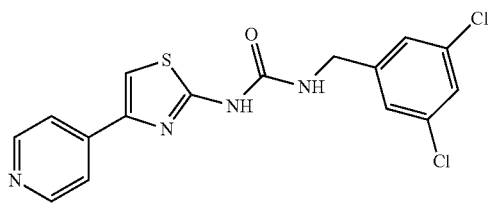 [SMILES: O=C(NCc1cc(Cl)cc(Cl)c1)Nc1nc(-c2ccncc2)cs1]

1-(3,5-dichlorobenzyl)-3-(4-(pyridin-4-yl)thiazol-2-yl)urea

This was prepared from 9 (0.122 g, 0.409 mmol) and (3,5-dichlorobenzylamine (0.050 g, 0.359 mmol) in the same manner as described for 1an. After cooling to room temperature, the solid precipitate was filtered, washed with THF, ether, hexane, and dried under vacuum. The pure 1cg was obtained as an offwhite solid (0.125 g, 0.330 mmol, 81%). $^1$H NMR (400 MHz, DMSO-d$_6$) δ 10.98 (s, 1H), 8.57 (d, J=6.2 Hz, 2H), 7.82 (s, 1H), 7.78 (d, J=6.2 Hz, 2H), 7.48 (t, J=1.9 Hz, 1H), 7.34 (d, J=1.9 Hz, 2H), 7.16 (t, J=5.9 Hz, 1H), 4.34 (d, J=6.0 Hz, 2H); HPLC purity 98.75% {$t_R$=5.627 min, Flow 1 ml/min, [(CH$_3$CN/(0.1% TFA in H$_2$O):30/70]}; purity 98.38% {$t_R$=10.313 min, Flow 1 ml/min, [(MeOH/(0.1% TFA in H$_2$O):60/40]}; HRMS (ESI+ve) m/z calculated for C$_{16}$H$_{12}$N$_4$Cl$_2$OS (M+H)$^+$ 379.01816, found 379.0182.

Compound 1ch

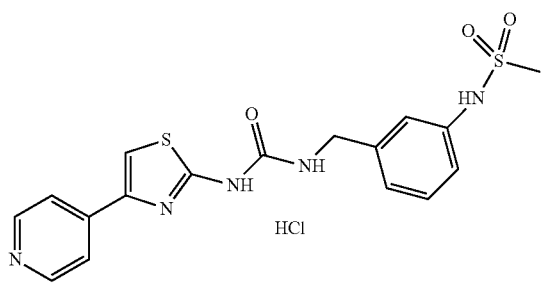 [SMILES: CS(=O)(=O)Nc1cccc(CNC(=O)Nc2nc(-c3ccncc3)cs2)c1 ; Cl]

N-(3-β3-(4-(pyridin-4-yl)thiazol-2-yl)ureido)methyl)phenyl)-methanesulfonamide hydrochloride This was prepared from 9 (0.085 g, 0.285 mmol) and N-(3-(aminomethyl)phenyl)methanesulfonamide hydrochloride (0.067 g, 0.283 mmol) in presence of DIPEA (0.070 ml) in the same manner as described for 1an. After cooling to room temperature, water (2 ml), NaOH (1M, aq., 5 ml) and ethyl acetate (5 ml) were added. The aqueous phase was separated and acidified with HCl (1M, aq., 10 ml). After standing at room temperature overnight, the solid precipitate was filtered, dried under vacuum. The pure 1ch was obtained as an off white solid (0.055 g, 0.125 mmol, 44%). $^1$H NMR (400 MHz, DMSO-d$_6$) δ 1.09 (s, 1H), 9.76 (s, 1H), 8.83 (d, J=6.6 Hz, 2H), 8.32 (s, 1H), 8.29 (d, J=6.6 Hz, 2H), 7.30-7.24 (m, 2H), 7.13 (s, 1H), 7.08 (d, J=9.5 Hz, 1H), 7.02 (d, J=7.6 Hz, 1H), 4.32 (d, J=5.9 Hz, 2H), 2.97 (s, 3H) HPLC purity 99.48% {$t_R$=10.600 min, Flow 1 ml/min, [(CH$_3$CN/(0.1% TFA in H$_2$O):20/80]}; purity 99.06% {$t_R$=5.887 min, Flow 1 ml/min, [(MeOH/(0.1% TFA in H$_2$O):40/60]}; HRMS (ESI+ve) m/z calculated for C$_{17}$H$_{17}$N$_5$O$_3$S$_2$ (M+H)$^+$ 404.0845, found 404.0842.

Compound 1ci

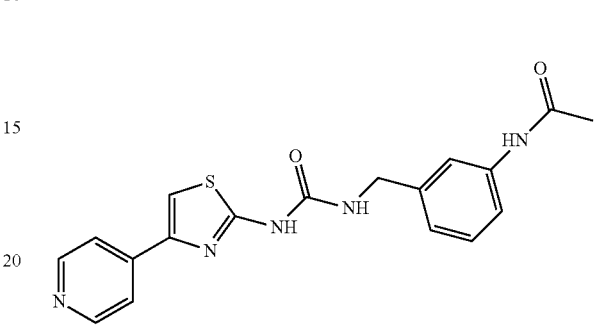

N-(3-((3-(4-(pyridin-4-yl)thiazol-2yl)ureido)methyl)phenyl)acetamide hydrochloride This was prepared from 9 (0.090 g, 0.302 mmol) and N-(3-(aminomethyl)phenyl)acetamide hydrochloride (0.072 g, 0.360 mmol) in presence of DIPEA (0.070 ml) in the same manner as described for 1an. After cooling to room temperature, ethyl acetate (5 ml), MeOH (1 ml). The solvent was slowly evaporated at room temperature. When the volume of the solvent was evaporated to ca. 1 ml, the solid precipitate was filtered, washed with THF (2 ml), washed with ethanol, and dried under vacuum. The pure 1ci was obtained as an off white solid (0.025 g, 0.068 mmol, 22%). $^1$H NMR (400 MHz, DMSO-d$_6$) δ 10.83 (s, 1H), 9.93 (s, 1H), 8.57 (d, J=4.6 Hz, 2H), 7.82 (s, 1H), 7.77 (d, J=6.1 Hz, 2H), 7.47-7.46 (m, 2H), 7.24 (t, J=8.5 Hz, 1H), 6.99 (bs, 1H), 6.95 (d, J=7.5 Hz, 1H), 4.31 (d, J=6.0 Hz, 2H), 2.00 (s, 3H) HPLC purity 98.36% {$t_R$=7.153 min, Flow 1 ml/min, [(CH$_3$CN/(0.1% TFA in H$_2$O):20/80]}; purity 98.01% {$t_R$=6.367 min, Flow 1 ml/min, [(MeOH/(0.1% TFA in H$_2$O):40/60]}; HRMS (ESI+ve) m/z calculated for C$_{17}$H$_{17}$N$_5$O$_2$S (M+H)$^+$ 368.1175, found 368.1171.

Compound 1cj

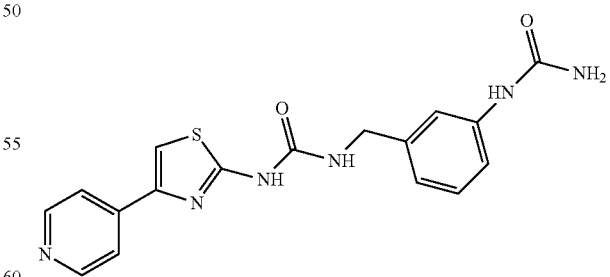

N-(3-((3-(4-(pyridin-4-yl)thiazol-2yl)ureido)methyl)phenyl)acetamide hydrochloride A mixture of 9 (0.052 g, 0.174 mmol), 1-(3-(aminomethyl)phenyl)urea (0.030 g, 0.181 mmol), in anhydrous THF (0.5 ml) was stirred in a sealed tube at 159° C. for 4 h. After cooling to room temperature, THF (1 ml) was added, and the solid precipitate was filtered, washed with THF (1 ml), and dried under vacuum. The pure 1cj was obtained as an off white solid (0.058 g, 0.157 mmol, 90%). $^1$H NMR (400 MHz, DMSO-$d_6$) δ 10.81 (s, 1H), 8.57 (d, J=6.1 Hz, 2H), 8.53 (s, 1H), 7.82 (s, 1H), 7.77 (d, J=6.1 Hz, 2H), 7.30-7.28 (m, 2H), 7.17-7.13 (m, 1H), 6.98 (s, 1H), 6.82 (d, J=7.4 Hz, 1H), 5.80 (s, 2H), 4.28 (d, J=5.9 Hz, 2H) HPLC purity 97.62% {$t_R$=4.953 min, Flow 1 ml/min, [(CH$_3$CN/(0.1% TFA in H$_2$O):30/70]}; purity 97.75% {$t_R$=4.739 min, Flow 1 ml/min, [(MeOH/(0.1% TFA in H$_2$O):40/60]}; HRMS (ESI+ve) m/z calculated for $C_{17}H_{16}N_6O_2S$ (M+H)$^+$ 369.1128, found 369.1130.

Compound 1cs

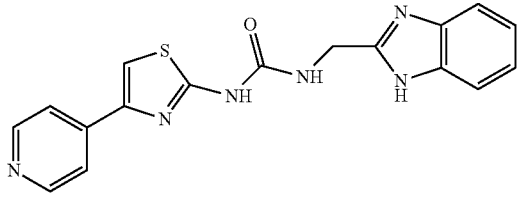 [SMILES: O=C(NCc1nc2ccccc2[nH]1)Nc1nc(-c2ccncc2)cs1]

1-((1H-Benzo[d]imidazol-2-yl)methyl)-3-(4-(pyridin-4-yl)thiazol-2-yl)urea

A mixture of 9 (0.115 g, 0.386 mmol), 2-(aminomethyl)benzimidazole dihydrochloride salt (0.102 g, 0.463 mmol), and DIPEA (0.050 ml) in anhydrous THF (0.6 ml) was stirred in a CEM microwave under the following conditions: power 150 W, ramp time 2 min, hold time 20 min, temperature 100° C., pressure 220 PSI. After cooling to room temperature, the solvent was removed under reduced pressure. The remaining solid was triturated in water, filtered, triturated in CH$_3$CN, filtered and dried under vacuum. The pure 1cs was obtained as a yellow solid (0.092 g, 0.262 mmol, 68%). $^1$H NMR (400 MHz, DMSO-$d_6$) δ 12.34 (s, 1H), 10.99 (s, 1H), 8.58 (d, J=5.9 Hz, 2H), 7.83 (s, 1H), 7.80 (d, J=6.1 Hz, 2H), 7.55 (d, J=6.4 Hz, 1H), 7.44 (d, J=7.6 Hz, 1H), 7.27 (s, 1H), 7.16-7.10 (m, 2H), 4.59 (d, J=5.5 Hz, 2H); HRMS (ESI+ve) m/z calculated for $C_{17}H_{15}N_6OS$ (M+H)$^+$ 351.1022, found 351.1026.

Compound 1ck

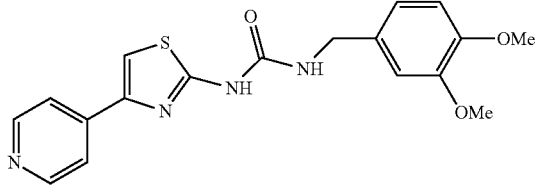 [SMILES: COc1ccc(CNC(=O)Nc2nc(-c3ccncc3)cs2)cc1OC]

1-(3,4-Dimethoxybenzyl)-3-(4-(pyridin-4-yl)thiazol-2-yl)urea

A mixture of 9 (0.116 g, 0.389 mmol), 3,4-dimethoxybenzyl amine (0.078 g, 0.467 mmol), in anhydrous THF (0.5 ml) was stirred in a sealed tube at 112° C. for 1 h. After cooling to room temperature, DCM (2 ml) and Hexane (2 ml) were added. The solid precipitate was filtered, dried under vacuum. The pure 1ck obtained as a white solid (0.105 g, 0.283 mmol, 73%). $^1$H NMR (400 MHz, DMSO-$d_6$) δ 10.75 (s, 1H), 8.57 (d, J=6.1 Hz, 2H), 7.81 (s, 1H), 7.77 (d, J=6.1 Hz, 2H), 6.92-6.88 (m, 3H), 6.81 (dd, J=1.6, 8.5 Hz, 1H), 4.26 (d, J=5.6 Hz, 2H), 3.72 (s, 3H), 3.71 (s, 3H); HPLC purity 98.72% {$t_R$=4.000 min, Flow 1 ml/min, [(MeOH/(0.1% TFA in H$_2$O): 50/50]}; HRMS (ESI+ve) m/z calculated for $C_{18}H_{19}N_4O_3S$ (M+H)$^+$ 371.1172, found 371.1165.

Compound 1cl

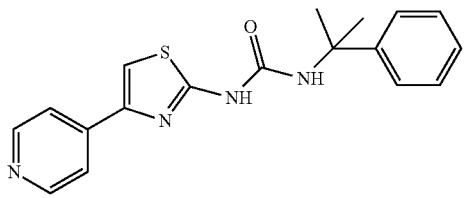 [SMILES: CC(C)(NC(=O)Nc1nc(-c2ccncc2)cs1)c1ccccc1]

1-(2-Phenylpropan-2-yl)-3-(4-(pyridin-4-yl)thiazol-2-yl)urea

This was prepared from 9 (0.096 g, 0.322 mmol) and cumylamine (0.052 g, 0.387 mmol) in the same manner as described for 1ck. After cooling to room temperature, the solid precipitate was filtered, dried under vacuum. The pure 1cl was obtained as a white solid (0.041 g, 0.121 mmol, 37%). $^1$H NMR (400 MHz, DMSO-$d_6$) δ 10.47 (s, 1H), 8.57 (d, J=6.1 Hz, 2H), 7.78 (s, 1H), 7.76 (d, J=6.1 Hz, 2H), 7.39 (d, J=7.3 Hz, 2H), 7.31 (t, J=7.7 Hz, 2H), 7.20 (t, J=7.8 Hz, 1H), 7.04 (s, 1H), 1.61 (s, 6H); $^1$H NMR (400 MHz, DMSO-$d_6$) δ 160.66, 153.21, 150.84, 148.20, 146.67, 141.65, 128.83, 126.90, 125.39, 120.47, 111.50, 55.46, 30.13; HPLC purity 98.92% {$t_R$=11.507 min, Flow 1 ml/min, [(MeOH/(0.1% TFA in H$_2$O):50/50]}; HRMS (ESI+ve) m/z calculated for $C_{18}H_{19}N_4OS$ (M+H)$^+$ 339.1274, found 339.1262.

Compound 1ct

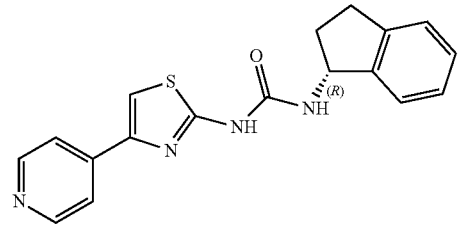

(R)-1-(2,3-Dihydro-1H-inden-1-yl)-3-(4-(pyridin-4-yl)thiazol-2-yl)urea

This was from 9 (0.096 g, 0.322 mmol) and (R)-(−)-1-aminoindane (0.051 g, 0.387 mmoo) in the same manner as described for 1ck. After cooling to room temperature, the solvent was removed under reduced pressure. The remaining solid was triturated with diethyl ether, filtered, and dried under vacuum. The pure 1ct was obtained as a white solid (0.069 g, mmol, %). ¹H NMR (400 MHz, DMSO-d₆) δ 10.51 (s, 1H), 8.57 (d, J=6.1 Hz, 2H), 7.84 (s, 1H), 7.77 (d, J=6.1 Hz, 2H,), 7.27-7.18 (m, 4H), 6.88 (d, J=8.1 Hz, 1H,), 5.18 (q, J=7.9 Hz, 1H,), 2.96-2.89 (m, 1H), 2.85-2.77 (m, 1H), 1.84-1.74 (d, 1H); HPLC; purity 96.39% {t_R=13.980 min, Flow 1 ml/min, [(MeOH/(0.1% TFA in H₂O):50/50]}; HRMS (ESI+ve) m/z calculated for C₁₈H₁₇N₄OS (M+H)⁺ 337.1117, found 337.1121.

was obtained as a white solid (0.088 g, 0.251 mmol, 79%). ¹H NMR (400 MHz, DMSO-d₆) δ 10.42 (s, 1H), 8.56 (d, J=6.1 Hz, 2H), 7.83 (s, 1H), 7.76 (d, J=6.1 Hz, 2H), 7.27-7.24 (m, 1H), 7.19-7.15 (m, 2H,), 7.11-7.09 (m, 1H), 6.90 (d, J=8.6 Hz, 1H), 4.88 (q, J=9.3 Hz, 1H), 2.81-2.64 (m, 2H), 1.99-1.90 (m, 1H), 1.81-1.71 (m, 3H); HPLC purity 95.70% {t_R=6.993 min, Flow 1 ml/min, [(MeOH/(0.1% TFA in H₂O):60/40]}; HRMS (ESI+ve) m/z calculated for C₁₉H₁₉N₄OS (M+H)⁺ 351.1274, found 351.1273.

Compound 1cu

Compound 1cw

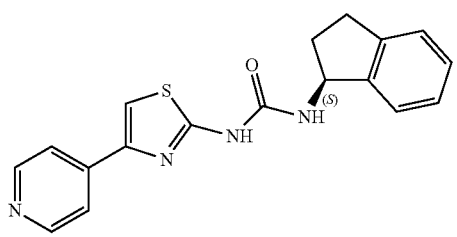

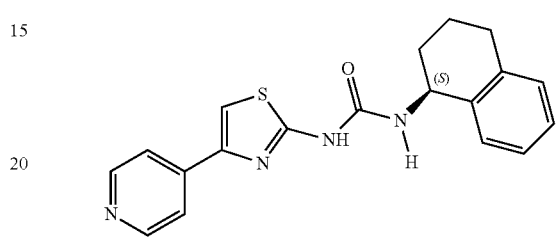

(S)-1-(2,3-Dihydro-1H-inden-1-yl)-3-(4-(pyridin-4-yl)thiazol-2-yl)urea (S)-1-(4-(Pyridin-4-yl)thiazol-2-A-3-(1,2,3,4-tetrahydronaphthalen-1-yl)urea This was prepared from 9 (0.109 g, 0.366 mmol) and (S)-(+)-1-aminoindane (0.058 g, 0.439 mmol) in the same manner as described for 1ck. After cooling to room temperature, the solvent was removed under reduced pressure. The remaining solid was triturated diethyl ether, filtered and dried under vacuum. The pure 1cu was obtained as a white solid (0.072 g, 0.213 mmol, 58%). ¹H NMR (400 MHz, DMSO-d₆) δ 10.53 (s, 1H), 8.57 (d, J=6.1 Hz, 2H,), 7.84 (s, 1H), 7.77 (d, J=6.1 Hz, 2H,), 7.28-7.18 (m, 4H), 6.88 (d, J=7.8 Hz, 1H), 5.20 (q, J=7.8 Hz, 1H), 2.96-2.88 (m, 1H), 2.85-2.77 (m, 1H), 1.84-1.75 (m, 1H); HPLC purity 96.89% {t_R=14.080 min, Flow 1 ml/min, [(MeOH/(0.1% TFA in H₂O):50/50]}; HRMS (ESI+ve) m/z calculated for C₁₈H₁₇N₄OS (M+H)⁺ 337.1117, found 337.1117.

This was prepared from 9 (0.098 g, 0.329 mmol) and (S)-(+)-1,2,3,4-tetrahydro-1-naphthylamine (0.058 g, 0.395 mmol) in the same manner as described for 1ck. After cooling to room temperature, the solvent was removed under reduced pressure. The remaining solid was triturated with diethyl ether, filtered, dried under vacuum. The pure 1cw was obtained as a white solid (0.088 g, 0.250 mmol, 76%). ¹H NMR (400 MHz, DMSO-d₆) δ 10.41 (s, 1H), 8.57 (d, J=5.6 Hz, 2H), 7.84 (s, 1H), 7.76 (d, J=6.0 Hz, 2H), 7.27-7.24 (m, 1H), 7.19-7.15 (m, 2H), 7.12-7.09 (m, 1H), 6.90 (d, J=8.2 Hz, 1H), 4.88 (q, J=6.1 Hz, 1H), 2.80-2.65 (m, 2H), 1.99-1.88 (m, 1H), 1.82-1.71 (m, 3H); HPLC purity 99.40% {t_R=15.273 min, Flow 1 ml/min, [(CH₃CN/(0.1% TFA in H₂O):30/70]}; HRMS (ESI+ve) m/z calculated for C₁₉H₁₉N₄OS (M+H)⁺ 351.1274, found 351.1278.

Compound 1cv

Compound 12c

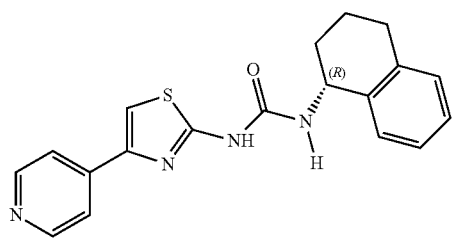

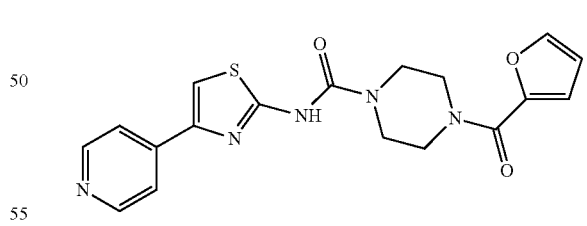

(R)-1-(4-(Pyridin-4-yl)thiazol-2-yl)-3-(1,2,3,4-tetrahydronaphthalen-1-yl)urea 4-(Furan-2-carbonyl)-N-(4-(pyridin-4-yl)thiazol-2-yl)piperazine-1-carboxamide This was prepared from 9 (0.095 g, 0.319 mmol) and (R)-(−)-1,2,3,4-tetrahydro-1-naphthylamine (0.056 g, 0.385 mmol) in the same manner as described for 1ck. The solid precipitate was filtered, dried under vacuum. The organic solution was concentrated to dryness and the remaining solid was triturated with a solution of diethyl ether, filtered, dried under vacuum. The two batches were combined and pure 1cv This was prepared from 9 (0.126 g, 0.423 mmol) and 1-(2-furoyl)piperazine (0.076 g, 0.423 mmol) in the same manner as described for 1ck. After cooling to room temperature, the solid precipitate was filtered, and dried under vacuum. The pure 12c was obtained as a white solid (0.081 g, 0.211 mmol, 50%). ¹H NMR (400 MHz, DMSO-d₆) δ 11.22 (s, 1H), 8.58 (d, J=6.2 Hz, 2H), 7.86 (m, 2H), 7.81 (d, J=6.1

Hz, 2H), 7.03 (dd, J=0.8, 3.4 Hz, 1H), 6.64 (dd, J=1.7, 3.5 Hz, 1H), 3.75-3.66 (m, 4H), 3.62-3.59 (m, 4H); HRMS (ESI+ve) m/z calculated for $C_{18}H_{18}N_5O_3S$ (M+H)$^+$ 384.1124, found 384.1127.

Compound 12d

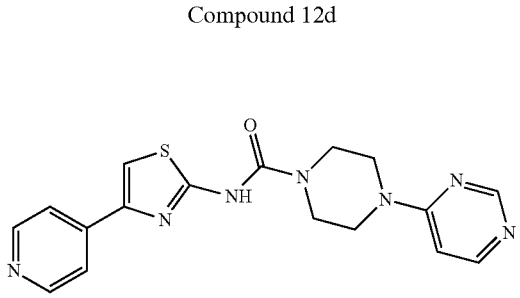

N-(4-(Pyridin-4-yl)thiazol-2-yl)-4-(pyrimidin-4-yl)piperazine-1-carboxamide

This was prepared from 9 (0.104 g, 0.349 mmol) and 1-(2-pyrazinyl)-piperazine (0.057 g, 0.349 mmol) in the same manner as described for 1ck. After cooling to room temperature, the solid precipitate was filtered, dried under vacuum. The pure 12d was obtained as a white solid (0.100 g, 0.271 mmol, 78%). $^1$H NMR (400 MHz, DMSO-d$_6$) δ 11.23 (s, 1H), 8.59 (d, J=6.1 Hz, 2H), 8.36 (d, J=1.4 Hz, 1H), 8.09 (dd, J=1.5, 2.6 Hz, 1H), 7.86-7.85 (m, 2H), 7.82 (d, J=6.1 Hz, 2H), 3.65-3.61 (m, 8H); HRMS (ESI+ve) m/z calculated for $C_{17}H_{18}N_7OS$ (M+H)$^+$ 368.1288, found 368.1284.

Compound 12e

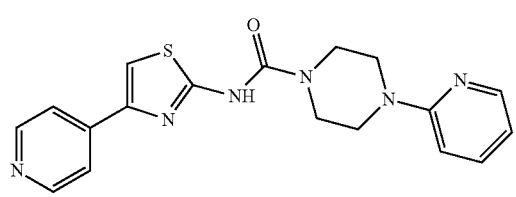 [SMILES: O=C(Nc1nc(-c2ccncc2)cs1)N1CCN(c2ccccn2)CC1]

4-(Pyridin-3-yl)-N-(4-(pyridin-4-yl)thiazol-2-yl)piperazine-1-carboxamide

This was prepared from 9 (0.107 g, 0.359 mmol) and 1-pyridin-3-yl-piperazine (0.058 g, 0.359 mmol) in the same manner as described for 1ck. After cooling to room temperature, the solid precipitate was filtered, and dried under vacuum. The pure 12e was obtained as an off white solid (0.069 g, 0.188 mmol, 53%). $^1$H NMR (400 MHz, DMSO-d$_6$) δ 11.22 (s, 1H), 8.59 (d, J=6.1 Hz, 2H), 8.33 (d, J=2.8 Hz, 1H), 8.01 (dd, J=1.0, 4.5 Hz, 1H), 7.85 (s, 1H), 7.82 (d, J=6.1 Hz, 2H), 7.36 (d, J=6.7 Hz, 1H), 7.22 (dd, J=4.6, 8.4 Hz, 1H), 3.68 (t, J=4.8 Hz, 4H), 3.22 (d, J=4.9 Hz, 4H); HRMS (ESI+ve) m/z calculated for $C_{18}H_{19}N_6OS$ (M+H)$^+$ 367.1335, found 367.1332.

Compound 12f

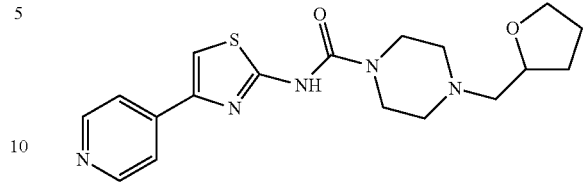

N-(4-(Pyridin-4-yl)thiazol-2-yl)-4-((tetrahydrofuran-2-yl)methyl)piperazine-1-carboxamide This was prepared from 9 (0.099 g, 0.332 mmol) and 1-((tetrahydrofuran-2-yl)methyl)piperazine (0.054 g, 0.317 mmol) in the same manner as described for 1ck. After cooling to room temperature, the solid precipitate was filtered, and dried under vacuum. The pure 12f was obtained as an off white solid (0.064 g, 0.171 mmol, 54%). $^1$H NMR (400 MHz, DMSO-d$_6$) δ 10.97 (s, 1H), 8.58 (d, J=6.1 Hz, 2H), 7.83 (s, 1H), 7.80 (d, J=6.1 Hz, 2H), 3.95-3.88 (m, 1H), 3.72-3.69 (m, 1H), 3.60-3.59 (m, 1H), 3.48 (t, J=4.9 Hz, 4H), 2.42-2.30 (m, 4H), 1.93-1.84 (m, 1H), 1.80-1.71 (m, 2H), 1.47-1.38 (m, 1H); HRMS (ESI+ve) m/z calculated for $C_{18}H_{24}N_5O_2S$ (M+H)$^+$ 374.1645, found 374.1641.

Compound 1 cm

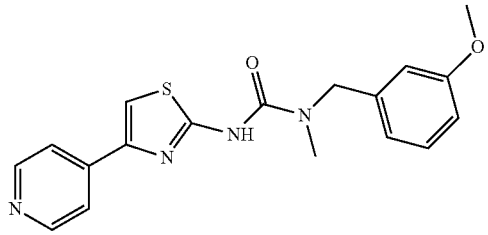 [SMILES: COc1cccc(CN(C)C(=O)Nc2nc(-c3ccncc3)cs2)c1]

1-(3-Methoxybenzyl)-1-methyl-3-(4-(pyridin-4-yl)thiazol-2-yl)urea

This was prepared from 9 (0.113 g, 0.379 mmol) and 3-methoxy-N-methylbenzylamine (0.068 g, 0.455 mmol) in the same manner as described for 1ck. After cooling to room temperature, the solvent was removed under reduced pressure. The remaining solid was triturated with diethyl ether, filtered, dried under vacuum. The pure 1 cm was obtained as a white solid (0.091 g, 0.256 mmol, 68%). $^1$H NMR (400 MHz, DMSO-d$_6$) δ 11.05 (s, 1H), 8.58 (d, J=6.1 Hz, 2H), 7.85 (s, 1H), 7.81 (d, J=6.1 Hz, 2H), 7.26 (t, J=7.9 Hz, 1H), 6.84-6.78 (m, 3H), 4.57 (s, 2H), 3.71 (s, 3H), 2.95 (s, 3H); $^{13}$C NMR (400 MHz, DMSO-d$_6$) δ 162.16, 160.10, 155.33, 150.73, 146.73, 141.83, 140.06, 130.38, 120.54, 119.95, 113.65, 112.91, 112.22, 55.60, 51.92, 35.07; HPLC purity 99.59% {$t_R$=7.213 min, Flow 1 ml/min, [CH$_3$CN/(0.1% TFA in H$_2$O):30/70]}; HRMS (ESI+ve) m/z calculated for $C_{18}H_{19}N_4O_2S$ (M+H)$^+$ 355.1223, found 355.1214.

Compound 1cn

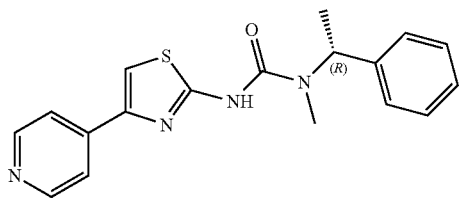

(R)-1-Methyl-1-(1-phenylethyl)-3-(4-(pyridin-4-yl)thiazol-2-yl)urea

This was prepared from 9 (0.104 g, 0.349 mmol) and 3(R)-(+)-N,α-dimethylbenzylamine (0.056 g, 0.419 mmol) in the same manner as described for 1ck. After cooling to room temperature, the solvent was removed under reduced pressure. The remaining solid was triturated with diethyl ether, filtered, dried under vacuum. The pure 1cn was obtained as a white solid (0.089 g, 0.262 mmol, 75%). $^1$H NMR (400 MHz, DMSO-$d_6$) δ 11.00 (s, 1H), 8.58 (d, J=6.1 Hz, 2H), 7.85 (s, 1H), 7.82 (d, J=6.1 Hz, 2H), 7.37-7.34 (m, 2H), 7.29-7.26 (m, 3H), 5.64 (q, J=7.1 Hz, 1H), 2.70 (s, 3H), 1.49 (d, J=7.0 Hz, 3H); $^{13}$C NMR (400 MHz, DMSO-$d_6$) δ 162.16, 155.24, 150.84, 146.89, 141.92, 141.47, 129.14, 127.84, 127.53, 120.54, 112.40, 52.66, 29.34, 17.03; HPLC purity 98.96% {$t_R$=10.487 min, Flow 1 ml/min, [(CH$_3$CN/(0.1% TFA in H$_2$O):30/70]}; purity 97.92% {$t_R$=11.860 min, Flow 1 ml/min, [(MeOH/(0.1% TFA in H$_2$O):50/50]}; HRMS (ESI+ve) m/z calculated for $C_{18}H_{19}N_4OS$ (M+H)$^+$ 339.1274, found 339.1268.

The enantiomeric excess was determined by HPLC using a Chiralcel OJ column [(Iso-propanol/Hexane:80/20), Flow 1 ml/min], $t_{R1}$=7.250 min, Area % 97.019.

Compound 1co

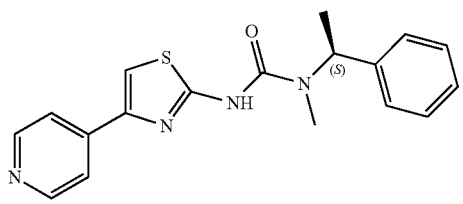

(S)-1-Methyl-1-(1-phenylethyl)-3-(4-(pyridin-4-yl)thiazol-2-yl)urea

This was prepared from 9 (0.106 g, 0.356 mmol) and (S)-(−)—N,α-dimethylbenzylamine (0.057 g, 0.427 mmol) in the same manner as described for 1ck. After cooling to room temperature, the reaction mixture washed with NaOH (2M, aq., 5 ml) and extracted with DCM (2×10 ml). The combined organic extracts were dried over Na$_2$SO$_4$ and the solvent removed under reduced pressure. The remaining solid was triturated with diethyl ether, filtered, and dried under vacuum. The pure 1co was obtained as a white solid (0.070 g, 0.206 mmol, 58%). $^1$H NMR (400 MHz, DMSO-$d_6$) δ; $^{13}$C NMR (200 MHz, DMSO-$d_6$) δ 162.19, 155.24, 150.84, 146.85, 141.93, 141.47, 129.14, 127.83, 127.52, 120.54, 112.40, 52.66, 29.34, 17.03; HPLC purity 99.43% {$t_R$=10.447 min, Flow 1 ml/min, [(CH$_3$CN/(0.1% TFA in H$_2$O):30/70]}; HRMS (ESI+ve) m/z calculated for $C_{18}H_{19}N_4OS$ (M+H)$^+$ 339.1274, found 339.1269.

The enantiomeric excess was determined by HPLC using a Chiralcel OJ column [(Iso-propanol/Hexane:80/20), Flow 1 ml/min], $t_{R1}$=7.165 min, Area % 0.495 (minor); $t_{R2}$=33.000 min, Area % 98.216 (major).

Compound 1cp

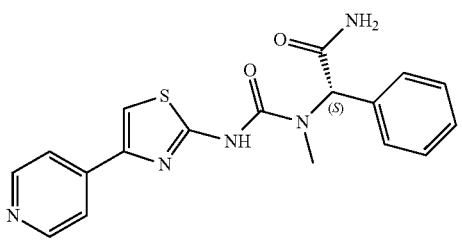

(S)-2-Phenyl-2-(3-(4-(pyridin-4-yl)thiazol-2-yl)ureido)acetamide

A mixture of 9 (0.116 g, 0.389 mmol), 2-phenylglycine amide hydrochloride salt (0.065 g, 0.346 mmol), and DIPEA (0.050 ml) in anhydrous THF (0.5 ml) was stirred in a CEM microwave under the following conditions: power 150 W, ramp time 2 min, hold time 20 min, temperature 100° C., pressure 220 PSI. After cooling to room temperature, the solid precipitate was filtered, washed with THF, and dried under vacuum to afford pure 1cp as an off white solid (0.037 g, 0.104 mmol, 30%). $^1$H NMR (400 MHz, DMSO-$d_6$) δ 10.79 (s, 1H), 8.57 (d, J=6.1 Hz, 2H), 7.86 (s, 1H), 7.81 (bs, 1H), 7.79 (d, J=6.1 Hz, 2H), 7.68 (bs, 1H), 7.42-7.40 (m, 2H), 7.35 (t, J=7.4 Hz, 2H), 7.29-7.26 (m, 1H), 5.29 (d, J=7.4 Hz, 1H); HRMS (ESI+ve) m/z calculated for $C_{17}H_{16}N_5O_2S$ (M+H)$^+$ 354.1019, found 354.1019.

Compound 1af-Mes

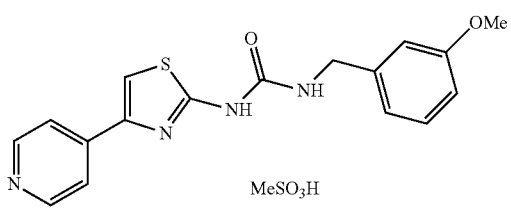 [SMILES: "MeSO3H" ; COc1cccc(CNC(=O)Nc2nc(-c3ccncc3)cs2)c1]

1-(3-methoxybenzyl)-3-(4-(pyridin-4-yl)thiazol-2-yl)urea methanesulfonate

A solution of methansulfonic acid (1.53 M in acetone, 0.250 ml, freshly prepared) was added to solution of 1af (0.107 g, 0.314 mmol) in acetone (3 ml) at 80° C. (oil bath T.) under Argon. The mixture was then stirred 80° C. (oil bath T.) under Argon for 15 min. After cooling to room temperature, acetone (1.5 ml) was added. The solid precipitate was filtered, washed with acetone (3×1.5 ml), hexane (5 ml), and dried under vacuum. The pure 1af-Mes was obtained as an off white solid (0.129 g, 0.293 mmol, 94%) $^1$H NMR (400 MHz, DMSO-d$_6$) δ 10.99 (s, 1H), 8.86 (d, J=8.2 Hz, 2H), 8.36-8.32 (m, 3H), 7.24 (t, J=8.1 HZ, 1H), 7.17 (s, 1H), 6.87-6.85 (m, 2H), 6.82-6.79 (m, 1H), 4.32 (d, J=6.0 Hz, 2H), 3.72 (s, 3H), 2.32-2.31 (m, 3H) HPLC purity 99.29% {t$_R$=6.080 min, Flow 1 ml/min, [(MeOH/(0.1% TFA in H$_2$O):50/50]}; HRMS (ESI+ve) m/z calculated for C$_{17}$H$_{16}$N$_5$O$_2$S (M+H)$^+$ 341.1066, found 341.1057.

Compound 1bo-Mes

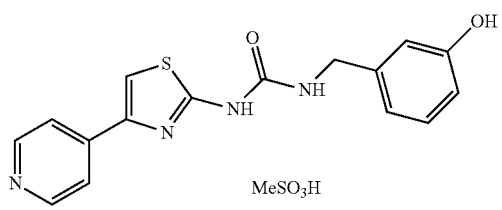 [SMILES: "MeSO3H" ; O=C(NCc1cccc(O)c1)Nc1nc(-c2ccncc2)cs1]

1-(3-hydroxybenzyl)-3-(4-(pyridin-4-yl)thiazol-2-yl) urea methanesulfonate

A solution of methansulfonic acid (1.53 M in acetone, 0.200 ml, freshly prepared) was added to mixture of 1bo (0.091 g, 0.279 mmol) in acetone (3 ml) and methanol (1 ml) at 80° C. (oil bath T.) under Argon. The solution was then stirred 80° C. (oil bath T.) under Argon for 15 min. After cooling to room temperature, acetone (5 ml) was added. The solution was stored in the fridge overnight. The solid precipitate was then filtered, washed with acetone (2 ml), hexane (5 ml), and dried under vacuum. The pure 1bo-Mes was obtained as an off white solid (0.090 g, 0.213 mmol, 76%). $^1$H NMR (400 MHz, DMSO-d$_6$) δ 10.96 (s, 1H), 9.36 (m, 1H), 8.86 (d, J=6.8 Hz, 2H), 8.36 (s, 1H), 8.33 (d, J=6.8 Hz, 2H), 7.11 (t, J=7.9 Hz, 1H), 7.08 (s, 1H), 6.70-6.68 (m, 2H), 6.63-6.61 (m, 1H), 4.26 (d, J=6.0 Hz, 2H), 2.31 (s, 3H); HPLC purity 99.69% {t$_R$=6.560 min, Flow 1 ml/min, [(MeOH/(0.1% TFA in H$_2$O):40/60]}; HRMS (ESI+ve) m/z calculated for C$_{16}$H$_{14}$N$_4$O$_2$S (M+H)$^+$ 327.0910, found 327.0938.

Compound 1am-Mes

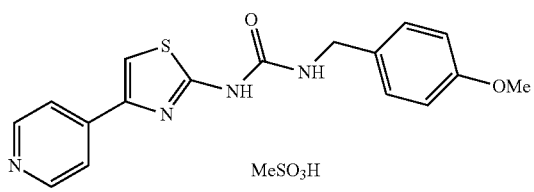 [SMILES: "MeSO3H" ; COc1ccc(CNC(=O)Nc2nc(-c3ccncc3)cs2)cc1]

1-(4-methoxybenzyl)-3-(4-(pyridin-4-yl)thiazol-2-yl) urea methanesulfonate

A solution of methansulfonic acid (1.53 M in acetone, 0.250 ml, freshly prepared) was added to mixture of 1am (0.082 g, 0.241 mmol) in acetone (4 ml) and methanol (1 ml) at 80° C. (oil bath T.) under Argon. The solution was then stirred 80° C. (oil bath T.) under Argon for 15 min. After cooling to room temperature, the solid precipitate was filtered, washed with acetone (3×1.5 ml), and dried under vacuum. The pure 1am-Mes was obtained as an off white solid (0.094 g, 0.215 mmol, 89%). $^1$H NMR (400 MHz, DMSO-d$_6$) δ 10.88 (s, 1H), 8.80 (d, J=5.8 Hz, 2H), 8.25-8.22 (m, 3H), 7.23 (d, J=8.7 Hz, 2H), 7.00 (bs, 1H), 6.89 (d, J=8.7 Hz, 2H), 4.27 (d, J=5.7 Hz, 2H), 3.72 (s, 3H), 2.28 (s, 3H), HPLC purity 99.51% {t$_R$=5.900 min, Flow 1 ml/min, [(MeOH/(0.1% TFA in H$_2$O):50/50]}; HRMS (ESI+ve) m/z calculated for C$_{17}$H$_{16}$N$_5$O$_2$S (M+H)$^+$ 354.1066, found 341.1092.

Compound 1af-HCl

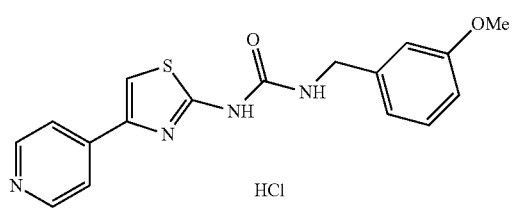 [SMILES: COc1cccc(CNC(=O)Nc2nc(-c3ccncc3)cs2)c1 ; Cl]

1-(3-methoxybenzyl)-3-(4-(pyridin-4-yl)thiazol-2-yl) urea hydrochloride

A solution of HCl (4 M in dioxane, 0.090 ml) was added to a solution of 1af (0.120 g, 0.329 mmol) in acetone (3 ml) at 80° C. (oil bath T.) under Argon. The solution was then stirred 80° C. (oil bath T.) under Argon for 15 min. After cooling to room temperature, the solid precipitate was then filtered, washed with acetone (4×1.5 ml), hexane (5 ml), and dried under vacuum. The pure 1af-HCl was obtained as an off white solid (0.124 g, 0.213 mmol, 93%). $^1$H NMR (400 MHz, DMSO-d$_6$) δ 11.10 (s, 1H), 8.82 (d, J=4.9 Hz, 2H), 8.30-8.26 (m, 3H), 7.39 (t, J=6.0 Hz, 1H), 7.24 (t, J=8.1 Hz, 1H), 6.87-6.86 (m, 2H), 6.87-6.80 (m, 1H), 4.32 (d, J=5.9 Hz, 2H), 3.72 (s, 1H); HPLC purity 99.11% {t$_R$=6.033 min, Flow 1 ml/min, [(MeOH/(0.1% TFA in H$_2$O):50/50]}; HRMS (ESI+ve) m/z calculated for C$_{17}$H$_{16}$N$_5$O$_2$S (M+H)$^+$ 341.1066, found 341.1094.

Compound 1bo-HCl

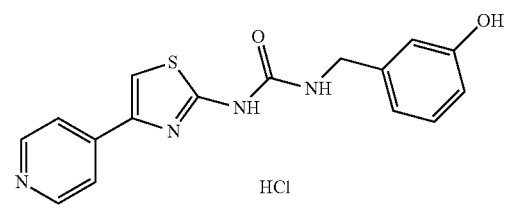 [SMILES: O=C(NCc1cccc(O)c1)Nc1nc(-c2ccncc2)cs1 ; Cl]

1-(3-hydroxybenzyl)-3-(4-(pyridin-4-yl)thiazol-2-yl) urea

A solution of HCl (4 M in dioxane, 0.100 ml) was added to a solution of 1bo (0.115 g, 0.352 mmol) in acetone (3 ml) at 80° C. (oil bath T.) under Argon. The solution was then stirred 80° C. (oil bath T.) under Argon for 20 min. After cooling to room temperature, the solid precipitate was then filtered, washed with acetone (6 ml), hexane (6 ml), and dried under vacuum. The pure 1bo-HCl was obtained as a pale yellow (0.123 g, 0.339 mmol, 96%). $^1$H NMR (400 MHz, DMSO-$d_6$) 11.06-10.99 (m, 1H), 9.39 (bs, 1H), 8.82-8.84 (m, 2H), 8.32-8.28 (m, 3H), 7.23 (bs, 1H), 7.11 (t, J=8.3 Hz, 1H), 6.70-6.78 (m, 2H), 6.64-6.61 (m, 1H), 4.27 (d, J=5.9 Hz, 2H); HPLC purity 99.35% {$t_R$=6.553 min, Flow 1 ml/min, [(MeOH/(0.1% TFA in H$_2$O):40/60]}.

Compound 1am-HCl

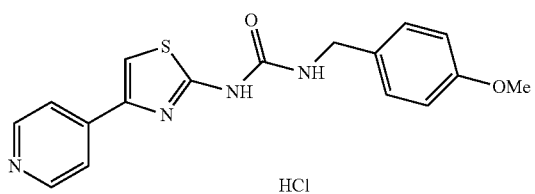 [SMILES: COc1ccc(CNC(=O)Nc2nc(-c3ccncc3)cs2)cc1 ; Cl]

1-(4-methoxybenzyl)-3-(4-(pyridin-4-yl)thiazol-2-yl) urea hydrochloride

A solution of HCl (4 M in dioxane, 0.050 ml) was added to mixture of 1am (0.055 g, 0.161 mmol) in acetone (3 ml) and methanol (6 ml) under reflux under Argon. The solution was then stirred under reflux under Argon for 1 h. After cooling to room temperature, the solution was stirred in the fridge for 24 h. The solid precipitate was then filtered, washed with cold methanol (1.5 ml), and dried under vacuum. The pure 1am-HCl was obtained as an off white solid (0.026 g, 0.069 mmol, 43%). $^1$H NMR (400 MHz, DMSO-$d_6$) δ 11.01-10.99 (m, 1H), 8.83-8.80 (m, 2H), 8.32-8.27 (m, 3H,), 7.22 (d, J=8.7 Hz, 2H), 7.17 (s, 1H), 6.88 (d, J=8.7 Hz, 2H), 4.27 (d, J=5.8 Hz, 2H), 3.71 (s, 3H); HPLC purity 99.68% {$t_R$=5.820 min, Flow 1 ml/min, [(MeOH/(0.1% TFA in H$_2$O):50/50]}; HRMS (ESI+ve) m/z calculated for $C_{17}H_{16}N_5O_2S$ (M+H)$^+$ 354.1066, found 341.1094.

Assays

Figure 4:
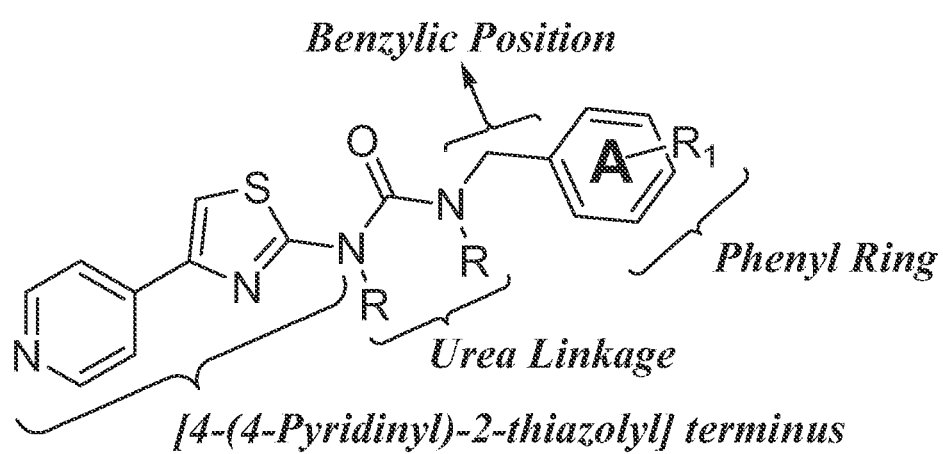
FIG. 4 shows structure-activity relationship (SAR) around the scaffold of 1aa.

Attention was focused on exploring, in turn, the SAR around the phenyl ring A, branching and substitution at the benzylic position, urea linkage of 1aa, without varying the [4-(4-pyridinyl)-2-thiazolyl] terminus (FIG. 4). The [4-(4-pyridinyl)-2-thiazolyl] group was believed to act as a hinge-binding moiety with the nitrogen of the pyridyl H-bonding to the back bone NH of the hinge Met156, as seen in the crystal complex of ROCK1 with Fasudil (PDB ID 2ESM) (Jacobs, et al., "The structure of dimeric ROCK I reveals the mechanism for ligand selectivity," *J Biol Chem*, 2006, 281:260-8).

All compounds were systematically screened against ROCK1 and ROCK2. IC$_{50}$ values were systematically determined only for compounds that inhibit 40% of ROCK1 kinase activities at 50 µM. The results are summarized in Tables 3, 4, 5, and 6 and discussed below and refer to FIG. 4.

Simple variations at the benzylic position and urea linkage were investigated at early stage and structural analysis of 1aa prompted the synthesis of three key analogs 6a, 8, and 1aw (Table 3). This preliminary SAR gave insight into the key features of 1aa for ROCK1 activity. Homologation of the benzylic methylene group to an ethylene group 1aw decreased the ROCK1 inhibition 3-fold. The dramatic loss of binding affinity of 8 can be attributable to the reduced degree of flexibility of the —NH(CO)-Ph group which negatively effects the binding orientation of the phenyl ring.

Replacement of the benzyl moiety of 1aa with a phenyl ring (6a) was not tolerated. The removal of the benzylic methylene group and the insertion of a direct bond between the sp$^2$ hybridized carbon and the sp$^2$ hybridized nitrogen produced a shorter more rigid structure (compared to the parent compound 1aa), thus impeding the phenyl ring to adopt an optimal binding orientation. Based on the initial SAR study, the benzylurea derivative 1aa remained the most promising lead.

TABLE 3

Preliminary SAR around compound 1aa.

| Compound | X | R | IC$_{50}$ ± SD (µM) ROCK1 | IC$_{50}$ ± SD (µM) ROCK2 |
|---|---|---|---|---|
| 1aa$^a$ | NH | benzyl | 0.15 ± 0.01 (n = 6) | 0.09 ± 0.02 (n = 6) |
| 1aa$^b$ | NH | benzyl | 0.17 ± 0.01 (n = 6) | 0.05 ± 0 (n = 6) |

TABLE 3-continued

Preliminary SAR around compound 1aa.

| Compound | X | R | IC$_{50}$ ± SD (μM) ROCK1 | IC$_{50}$ ± SD (μM) ROCK2 |
|---|---|---|---|---|
| 6a | NH | phenyl | ROCK1 % inhibition @ 50 μM: 10.43 ± 3.14 | ND |
| 8 | NH | C(O)-phenyl | ROCK1 % inhibition @ 50 μM: 16.30 ± 3.31 | ND |
| 1aw | NH | CH$_2$CH$_2$-phenyl | 0.48 ± 0.037 (n = 6) | 0.38 ± 0.107 (n = 6) |

Key: a) prepared via route described in Scheme 1;
b) prepared via route described in Scheme 2;
n = number of repeats Next, the effect of the substitution on the phenyl ring A was studied and systematically evaluated (FIG. 4). The results are summarized in Table 4. Groups located at the meta position appeared in general to be favored for optimal activity. The meta-chloro (1an), and meta-fluoro (1aj) derivatives showed potency (IC$_{50}$ values of 0.10 and 0.14 μM, respectively) comparable to the activity of the parent compound 1aa whereas the meta-methyl substitution (1ba) resulted in a 3-fold decrease in activity. A significant enhancement in potency resulted for the 3-hydroxy derivative 1bo (IC$_{50}$ 8 nM). The corresponding methyl ether (1af) did not dramatically reduce the activity. However, larger alkoxy groups such as ethoxy (1bw), propoxy (1bx), and iso-propoxy (1bu) and ethoxymethoxy (1bm) were not tolerated. When the methoxy group of 1af was replaced with OCHF$_2$ and OCF$_3$ groups all activity was lost. These results generally indicate that only polar groups adding a limited steric hindrance at the meta position do not lead to a significant loss of potency compared to the parent compound 1bo. In addition, whereas the binding affinity of 1af could derive from the ability the methoxy group of acting as a hydrogen bond acceptor, the greater potency of 1bo might be due to the H-bond donor/acceptor properties of phenol.

Next, the bioisosteric replacement of the 3-hydroxy group was studied with the aim of retaining the high binding affinity and improving the pharmacological properties of 1bo and further probing the importance of the OH group. First, the OH→NH$_2$ (1ay) replacement resulted in a 6-fold decrease in activity compared to 1bo. Additionally, monomethylation of the NH$_2$ of compound 1ay resulted in further loss of activity (1bq). The indole analog 1bn displayed showed 470-fold decrease in activity for ROCK1.

The SAR around the phenyl ring A indicated that changes are not generally tolerated at the ortho- and para-position of 1aa. The introduction of a methoxy (1am), nitro (1za), amino (1bl), chloro (1ab), and methyl (1bd) at the para-position resulted in a dramatic loss in activity. The corresponding para-fluoro (1ak) and para-hydroxy (1ax) analogs were also less active than 1aa, but remained submicromlar. A similar, but less detrimental trend was also observed for the ortho substitution (compare compounds 1ad, 1ac, and 1ae). The 2-methyl analog 1bt was found to be equipotent with the parent compound 1aa. The di-substituted analogs 1bb, 1bc, 1ck, 1ag, 1cd, and 1cq were less active than 1aa. Finally, replacement of the phenyl ring by a naphthyl (1av), pyridyl (1ao, 1ap, and 1aq,) and furan ring (1ak1) led to a 6-fold to 14-fold loss in potency.

TABLE 4

Effect of the substitution of the aromatic ring A

| Compound | R | $R_1$ | $R_2$ | IC$_{50}$ ± SD (μM) ROCK1 | IC$_{50}$ ± SD (μM) ROCK2 |
|---|---|---|---|---|---|
| 1aa[a] | H | H | benzyl | 0.15 ± 0.01 (n = 6) | 0.09 ± 0.02 (n = 6) |
| 1aa[b] | H | H | benzyl | 0.17 ± 0.01 (n = 6) | 0.05 ± 0 (n = 6) |
| 1au | H | Me | benzyl | 0.11 ± 0.003 (n = 6) | 0.07 ± 0.015 (n = 6) |
| 1af[a] | H | H | 3-OMe-benzyl | 0.06 ± 0.04 (n = 19) | 0.01 ± 0.003 (n = 15) |
| 1af[b] | H | H | 3-OMe-benzyl | 0.027 ± 0.005 (n = 8) | 0.011 ± 0.002 (n = 6) |
| 1af-Mes | H | H | 3-OMe-benzyl, MeSO$_3$H | 0.03 ± 0.01 (n = 3) | 0.01 ± 0.00 (n = 3) |
| 1af-HCl | H | H | 3-OMe-benzyl, HCl | 0.023 ± 0.01 (n = 3) | 0.014 ± 0.01 (n = 3) |
| 1ad | H | H | 2-OMe-benzyl | 1.40 ± 0.11 (n = 6) | 0.47 ± 0.03 (n = 6) |
| 1am | H | H | 4-OMe-benzyl | ROCK1 % inhibition @ 50 μM: 9.12 ± 1.62 | ND |

TABLE 4-continued
Effect of the substitution of the aromatic ring A
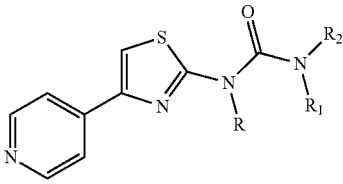
| Compound | R | R₁ | R₂ | IC$_{50}$ ± SD (μM) ROCK1 | IC$_{50}$ ± SD (μM) ROCK2 |
|---|---|---|---|---|---|
| 1am-Mes | H | H | 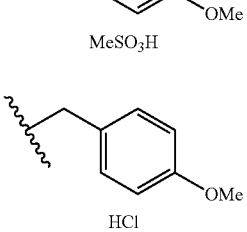 MeSO₃H | 36.19 ± 10.00 n = 3 | 7.42 ± 2.29 n = 3 |
| 1am-HCl | H | H | 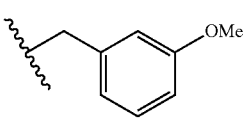 [SMILES: *Cc1cccc(OC)c1] HCl | ROCK1 % inhibition @ 50 μM: 15.26 ± 0.91 | ND |
| 1al | Me | H | 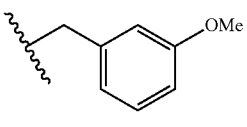 [SMILES: *Cc1cccc(OC)c1] | 0.06 ± 0.04 (n = 12) | 0.002 ± 0.0015 (n = 12) |
| 1cm | H | Me | 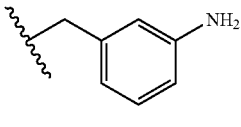 [SMILES: *Cc1cccc(N)c1] | 0.04 ± 0.01 (n = 12) | 0.015 ± 0.004 (n = 12) |
| 1ay | H | H | 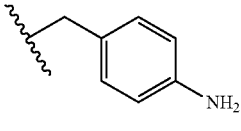 | 0.05 ± 0.009 (n = 12) | 0.02 ± 0.008 (n = 12) |
| 1bl | H | H | 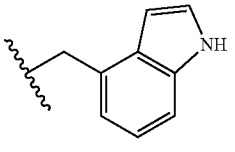 [SMILES: *Cc1cccc2[nH]ccc12] | 45.85 ± 5.15 (n = 6) | 17.40 ± 3.79 (n = 6) |
| 1bn | H | H | 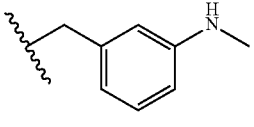 | 37.79 ± 7.81 (n = 6) | 31.09 ± 9.14 (n = 6) |
| 1bq | H | H | 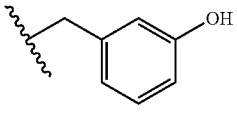 [SMILES: *Cc1cccc(O)c1] | 0.47 ± 0.013 (n = 6) | 0.24 ± 0.04 (n = 6) |
| 1bo | H | H |  | 0.008 ± 0.001 (n = 10) | 0.006 ± 0.001 (n = 9) |

TABLE 4-continued

Effect of the substitution of the aromatic ring A

| Compound | R | R₁ | R₂ | IC$_{50}$ ± SD (μM) ROCK1 | IC$_{50}$ ± SD (μM) ROCK2 |
|---|---|---|---|---|---|
| 1bo-Mes | H | H | 3-hydroxybenzyl; MeSO₃H | 0.013 ± 0.00 n = 3 | 0.008 ± 0.00 n = 3 |
| 1bo-HCl | H | H | 3-hydroxybenzyl; HCl | 0.009 ± 0.00 n = 3 | 0.006 ± 0.00 n = 3 |
| 1cj | H | H | 3-(ureido)benzyl | 1.15 ± 0.39 n = 3 | 0.18 ± 0.04 n = 3 |
| 1ci | H | H | 3-(acetamido)benzyl | 1.25 ± 0.21 n = 3 | 0.13 ± 0.02 n = 3 |
| 1ch | H | H | 3-(methanesulfonamido)benzyl | 0.56 ± 0.10 n = 3 | 0.10 ± 0.03 n = 3 |
| 1bp | H | H | 2-hydroxybenzyl | 0.62 ± 0.019 (n = 6) | 0.28 ± 0.05 (n = 6) |
| 1ax | H | H | 4-hydroxybenzyl | 0.38 ± 0.046 (n = 6) | 0.14 ± 0.029 (n = 6) |
| 1bm | H | H | 3-(2-methoxyethoxy)benzyl | 0.50 ± 0.05 (n = 6) | 0.24 ± 0.03 (n = 6) |
| 1bw | H | H | 3-ethoxybenzyl | 2.14 ± 0.62 (n = 3) | 0.29 ± 0.17 (n = 3) |

TABLE 4-continued
Effect of the substitution of the aromatic ring A
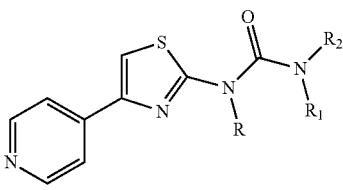
| Compound | R | R₁ | R₂ | IC$_{50}$ ± SD (μM) ROCK1 | IC$_{50}$ ± SD (μM) ROCK2 |
|---|---|---|---|---|---|
| 1bx | H | H | 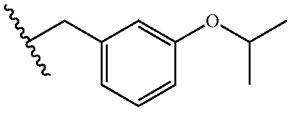 [SMILES: *Cc1cccc(OC(C)C)c1] | 3.36 ± 1.00 (n = 3) | 0.68 ± 0.43 (n = 3) |
| 1bu | H | H | 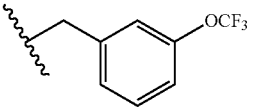 [SMILES: *Cc1cccc(OC(F)(F)F)c1] | 13.00 ± 1.38 (n = 6) | 3.44 ± 0.87 (n = 6) |
| 1br | H | H | 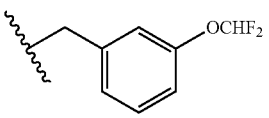 [SMILES: *Cc1cccc(OC(F)F)c1] | ROCK1 % inhibition @ 50 μM: 7.48 ± 5.21 | ND |
| 1bs | H | H | 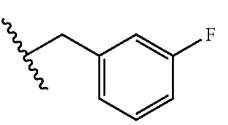 [SMILES: *Cc1cccc(F)c1] | 0.92 ± 0.10 (n = 6) | 0.35 ± 0.08 (n = 6) |
| 1aj[a] | H | H | 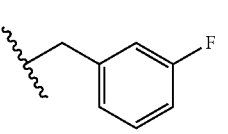 [SMILES: *Cc1cccc(F)c1] | 0.14 ± 0.03 (n = 14) | 0.06 ± 0.01 (n = 12) |
| 1aj[b] | H | H | 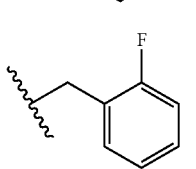 | 0.10 ± 0.02 (n = 6) | 0.05 ± 0.01 (n = 6) |
| 1ac | H | H | 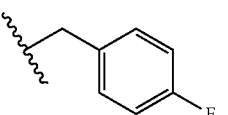 | 0.40 ± 0.03 (n = 6) | 0.12 ± 0.01 (n = 6) |
| 1ak | H | H | 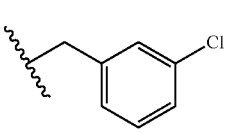 [SMILES: *Cc1cccc(Cl)c1] | 0.57 ± 0.05 (n = 6) | 0.19 ± 0.00 (n = 6) |
| 1an | H | H | 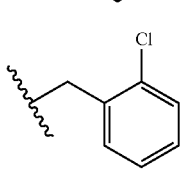 | 0.14 ± 0.02 (n = 6) | 0.06 ± 0.01 (n = 6) |
| 1ae | H | H |  | 0.34 ± 0.02 (n = 6) | 0.11 ± 0.01 (n = 6) |

TABLE 4-continued

Effect of the substitution of the aromatic ring A

| Compound | R | $R_1$ | $R_2$ | $IC_{50} \pm SD$ (μM) ROCK1 | $IC_{50} \pm SD$ (μM) ROCK2 |
|---|---|---|---|---|---|
| 1ab | H | H | 4-Cl-benzyl | 2.39 ± 0.53 (n = 6) | 1.10 ± 0.16 (n = 6) |
| 1ba | H | H | 3-Me-benzyl | 0.46 ± 0.08 (n = 6) | 0.12 ± 0.03 (n = 6) |
| 1bt | H | H | 2-Me-benzyl | 0.15 ± 0.03 (n = 6) | 0.12 ± 0.02 (n = 6) |
| 1bd | H | H | 4-Me-benzyl | 5.16 ± 0.51 (n = 6) | 2.05 ± 0.15 (n = 6) |
| 1az | H | H | 4-$NO_2$-benzyl | ROCK1 % inhibition @ 50 μM: 34.55 ± 2.07 | ND |
| 1bb | H | H | 3,5-(OMe)$_2$-benzyl | ROCK1 % inhibition @ 50 μM: 9.95 ± 3.40 | ND |
| 1bc | H | H | 2,3-(OMe)$_2$-benzyl | 35.42 ± 6.78 (n = 6) | 19.73 ± 2.94 (n = 6) |
| 1ck | H | H | 3,4-(OMe)$_2$-benzyl | 45.13 ± 5.57 (n = 6) | 25.02 ± 1.01 (n = 6) |
| 1ag | H | H | 2,4-Cl$_2$-benzyl | 1.88 ± 0.17 (n = 6) | 0.40 ± 0.07 (n = 6) |

TABLE 4-continued

Effect of the substitution of the aromatic ring A

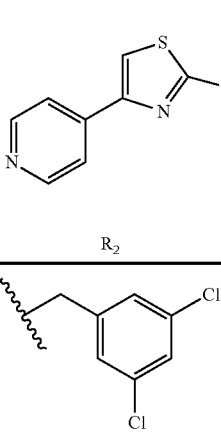

| Compound | R | $R_1$ | $R_2$ | $IC_{50} \pm SD\ (\mu M)$ ROCK1 | $IC_{50} \pm SD\ (\mu M)$ ROCK2 |
|---|---|---|---|---|---|
| 1cg | H | H | 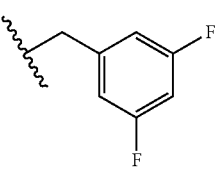 [SMILES: *Cc1cc(F)cc(F)c1] | ROCK1 % inhibition @ 50 μM: −6.26 ± 4.67 | ND |
| 1cd | H | H | 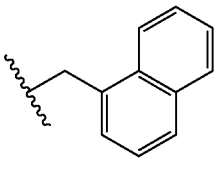 [SMILES: *Cc1cccc2ccccc12] | 4.07 ± 2.76 (n = 3) | 0.96 ± 0.56 (n = 3) |
| 1av | H | H | 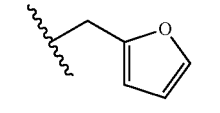 [SMILES: *Cc1ccco1] | 1.10 ± 0.202 (n = 6) | 0.58 ± 0.218 (n = 6) |
| 1ak1 | H | H | 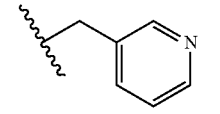 [SMILES: *Cc1cccnc1] | 1.17 ± 0.15 (n = 6) | 0.38 ± 0.03 (n = 6) |
| 1ao | H | H | 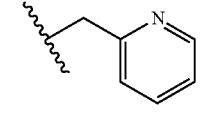 [SMILES: *Cc1ccccn1] | 0.91 ± 0.15 (n = 6) | 0.49 ± 0.07 (n = 6) |
| 1ap | H | H | 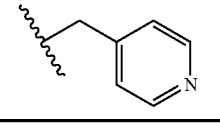 | 1.82 ± 0.18 (n = 6) | 1.44 ± 0.22 (n = 6) |
| 1aq | H | H |  | 2.07 ± 0.29 (n = 6) | 1.47 ± 0.13 (n = 6) |

Key: a) prepared via route described in Scheme 1;
b) prepared via route described in Scheme 2;
n = number of repeats Next, the effect of branching and substitution of the benzylic position of 1aa was investigated (Table 5). A small set of α-substituted benzylurea was prepared and tested. Within this series, a dramatic difference in ROCK inhibition of enantiomers was observed when a stereogenic center was introduced at the benzylic position.

The (R)-α-methylbenzylurea 1ah was found to be 7-fold more potent than the parent compound 1aa, and 215-fold more potent than its enantiomer 1ai. The (R)-α-ethylbenzylurea 1be was 3.5-fold less active than 1aa but remained much more active (745-fold) than its enantiomer 1bf. Further, the (S)-α-methylhydroxy analog 1at showed an $IC_{50}$ of 30 nM for ROCK1 inhibition. The S enantiomer 1at is clearly a more potent inhibitor than its R enantiomer 1as ($IC_{50}$=5.2 μM). The $IC_{50}$ of the racemate 1ar (60 nM) also shows that the activity results from the S enantiomer alone. Methylation of the hydroxy group of 1at resulted in 3.5-fold loss of potency (1bj). This result suggests that hydroxy group is serving as hydrogen bonding donor. Replacement of the —CH$_2$OH group by —CONH$_2$ group as an alternative H-bond donor caused an 11-fold reduction in potency (1cp). The α,α-dimethylbenzyl analog 1ba was slightly less active than the parent compound 1aa. Further, the incorporation of a phenyl ring at the benzylic position of 1aa led to a 12-fold loss in activity (1bi).

Lastly the importance of the NH functionalities was studied, limiting the examples to N-methylation. N1- and N2-methylation was generally tolerated as shown by analogs 1al, 1cm, 1au, 1co, and 1cn. This limited array of N-methylated compounds appears to exclude the engagement of NH in hydrogen bonding to the protein active site.

TABLE 5

Effect of the substitution and branching at the benzylic position

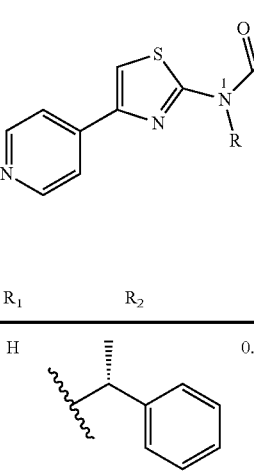

| Compound | R | R₁ | R₂ | IC₅₀ ± SD (μM) ROCK1 | IC₅₀ ± SD (μM) ROCK2 |
|---|---|---|---|---|---|
| 1ah[a] | H | H | 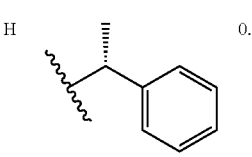 | 0.019 ± 0.03 (3/2009) (n = 16) to repeat | 0.012 ± 0.004 (3/2009) (n = 16) |
| 1ah[b] | H | H | 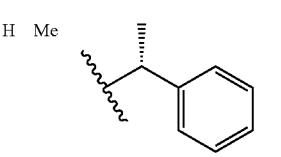 | 0.043 ± 0.007 (n = 6) | 0.012 ± 0.002 (n = 6) |
| 1cn | H | Me | 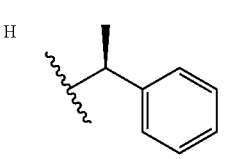 | 0.12 ± 0.04 (n = 12) | 0.047 ± 0.018 (n = 12) |
| 1ai[a] | H | H | 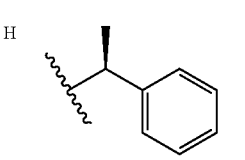 | 3.56 ± 0.77 (n = 12) | 1.6 ± 0.42 (n = 12) |
| 1ai[b] | H | H | 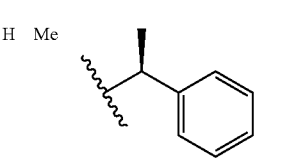 | 3.29 ± 0.4 (n = 6) | 1.9 ± 0.52 (n = 6) |
| 1co | H | Me | 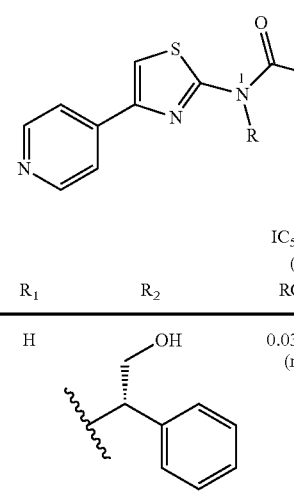 | 6.44 ± 1.67 (n = 12) | 2.67 ± 0.89 (n = 12) |

TABLE 5-continued

Effect of the substitution and branching at the benzylic position

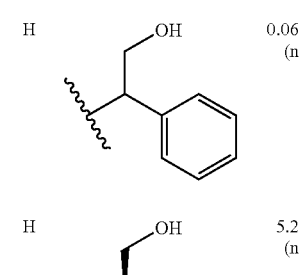

| Compound | R | R₁ | R₂ | IC₅₀ ± SD (μM) ROCK1 | IC₅₀ ± SD (μM) ROCK2 |
|---|---|---|---|---|---|
| 1at | H | H | 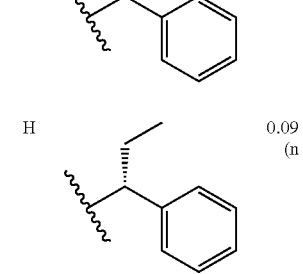 | 0.03 ± 0.018 (n = 16) | 0.03 ± 0.01 (n = 16) |
| 1ar | H | H | 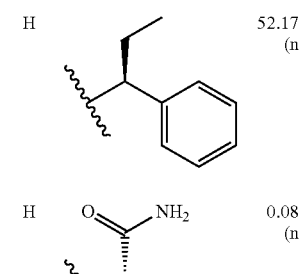 | 0.06 ± 0.02 (n = 12) | 0.03 ± 0.02 (n = 12) |
| 1as | H | H | 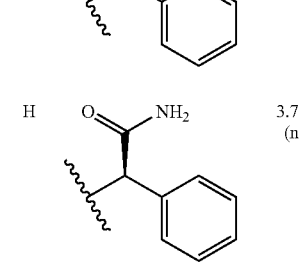 | 5.2 ± 0.62 (n = 12) | 2.5 ± 1 (n = 12) |
| 1be | H | H | 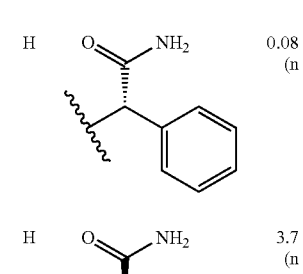 | 0.09 ± 0.02 (n = 12) | 0.03 ± 0.01 (n = 12) |
| 1bf | H | H | 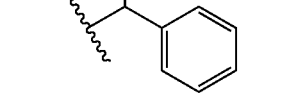 | 52.17 ± 3.64 (n = 6) | 22.04 ± 7.79 (n = 6) |
| 1cp | H | H |  | 0.08 ± 0.01 (n = 12) | 0.04 ± 0.016 (n = 12) |
| 1bv | H | H |  | 3.7 ± 0.5 (n = 6) | 2.1 ± 0.36 (n = 6) |

TABLE 5-continued

Effect of the substitution and branching at the benzylic position

| Compound | R | R₁ | R₂ | $IC_{50} \pm SD$ (µM) ROCK1 | $IC_{50} \pm SD$ (µM) ROCK2 |
|---|---|---|---|---|---|
| 1bj | H | H | (S)-CH(CH₂OMe)Ph | 0.07 ± 0.005 (n = 12) | 0.03 ± 0.009 (n = 12) |
| 1bk | H | H | (R)-CH(CH₂OMe)Ph | 29.48 ± 3.28 (n = 6) | 11.48 ± 1.244 (n = 6) |
| 1cl | H | H | C(CH₃)₂Ph | 0.19 ± 0.04 (n = 6) | 0.07 ± 0.02 (n = 6) |
| 1bi | H | H | CH(Ph)Ph | 1.87 ± 0.54 (n = 6) | 0.53 ± 0.10 (n = 6) |

Key: a) prepared via route described in Scheme 1;
b) prepared via route described in Scheme 2;
n = number of repeats

TABLE 6

Effect of the substitution and branching at the benzylic position

| Compound | R₁ | $IC_{50} \pm SD$ (µM) Rock1 | $IC_{50} \pm SD$ (µM) Rock2 |
|---|---|---|---|
| 1bh | (S)-1-(3-methoxyphenyl)ethyl | 0.030 ± 0.022 (n = 15) | 0.009 ± 0.007 (n = 15) |
| 1bg | (R)-1-(3-methoxyphenyl)ethyl | 18.71 ± 2.09 (n = 9) | 3.25 ± 0.96 (n = 9) |
| 1by | (R)-1-(4-methoxyphenyl)ethyl | ROCK1 % inhibition @ 50 µM: 1.09 ± 2.91 | ND |
| 1bz | (S)-1-(4-methoxyphenyl)ethyl | >50 n = 4 | 11.94 ± 4.69 (n = 3) |
| 1cf | (R)-1-(3-fluorophenyl)ethyl | 29.97 ± 10.04 (n = 4) | 10.97 ± 6.74 (n = 3) |
| 1cc | (S)-1-(3-fluorophenyl)ethyl | 0.11 ± 0.01 (n = 3) | 0.03 ± 0.01 (n = 3) |

Finally, the best features of the most potent compounds derived from the above described SAR studies were used to design new inhibitors (Table 4 and 5). A small set of additional phenylethyl analogs (1bh, 1bg, 1by, 1bz, 1cf, 1cc, 1ca, 1ce, 1cd) were synthesized and are shown with their ROCK inhibition activities in Table 6. Within this series, the same sense of enantiomeric selectivity is preserved with chiral selectivity ranging between 630- and 270-fold. None of the synthesized compounds exhibited greater potency compared to the parent compounds, and the desired "potency enhancement effect" was not observed. However, the activity of compound 1bh is still notable (ROCK1 $IC_{50}$ 30 nM) comparable with the $IC_{50}$s observed for 1af and 1ah. The H—F replacement in compound 1ah resulted in a 3-fold less potent analog (1cc), but similar in activity to 1aj.

TABLE 6-continued

Effect of the substitution and branching at the benzylic position

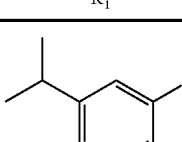

| Compound | R₁ | IC$_{50}$ ± SD (μM) Rock1 | IC$_{50}$ ± SD (μM) Rock2 |
|---|---|---|---|
| 1ca | 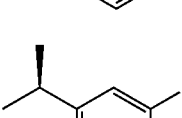 | 0.43 ± 0.13 (n = 3) | 0.28 ± 0.13 (n = 3) |
| 1ce | 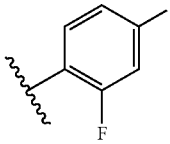 | >50 n = 2 | ND |

TABLE 6-continued

Effect of the substitution and branching at the benzylic position

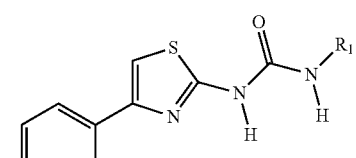

| Compound | R₁ | IC$_{50}$ ± SD (μM) Rock1 | IC$_{50}$ ± SD (μM) Rock2 |
|---|---|---|---|
| 1cb | 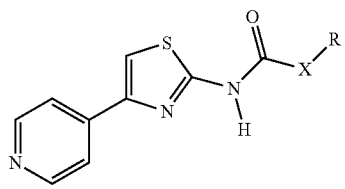 | 0.55 ± 0.32 (n = 3) | 0.07 ± 0.02 (n = 3) |

Key: a) prepared via route described in Scheme 1;
b) prepared via route described in Scheme 2;
n = number of repeats In order to expand the SAR around the urea scaffold, further analogs were synthesized. IC$_{50}$s are reported in Tables 7 and 8.

TABLE 7

SAR expansion of 1aa.

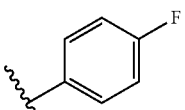

| Compound | X | R | IC$_{50}$ ± SD (μM) ROCK1 | IC$_{50}$ ± SD (μM) ROCK2 |
|---|---|---|---|---|
| 6b | NH | 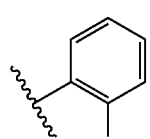 | ROCK1 % inhibition @ 50 μM: 14.54 ± 1.81 | ND |
| 6c | NH | 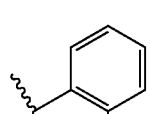 | ROCK1 % inhibition @ 50 μM: 8.06 ± 0.93 | ND |
| 6d | NH |  | ROCK1 % inhibition @ 50 μM: 13.33 ± 1.89 | ND |
| 6e | NH |  | 2.49 ± 1.07 (n = 3) | 3.75 ± 0.39 (n = 3) |

TABLE 7-continued

SAR expansion of 1aa.

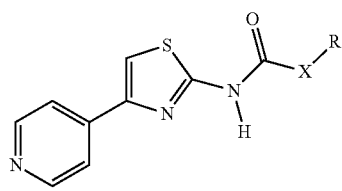

| Compound | X | R | IC$_{50}$ ± SD (μM) ROCK1 | IC$_{50}$ ± SD (μM) ROCK2 |
|---|---|---|---|---|
| 1cr | NH | 2,3-dihydro-1H-inden-2-yl | ROCK1 % inhibition @ 50 μM: 40.91 ± 3.03 | ND |
| 1cs | NH | (1H-benzimidazol-2-yl)methyl | ROCK1 % inhibition @ 50 μM: 40.91 ± 3.03 | ND |
| 1ct | NH | (R)-2,3-dihydro-1H-inden-1-yl | 28.24 ± 1.84 (n = 6) | 52.47 ± 1.75 (n = 3) |
| 1cu | NH | (S)-2,3-dihydro-1H-inden-1-yl | 3.21 ± 0.90 (n = 6) | 1.83 ± 0.56 (n = 6) |
| 1cv | NH | (R)-1,2,3,4-tetrahydronaphthalen-1-yl | 6.99 ± 1.61 (n = 6) | 3.82 ± 1.53 (n = 6) |
| 1cw | NH | (S)-1,2,3,4-tetrahydronaphthalen-1-yl | 6.25 ± 1.36 (n = 6) | 3.35 ± 0.87 (n = 6) |

TABLE 6

SAR expansion of 1aa

| Compound | | IC$_{50}$ ± SD (μM) ROCK1 | IC$_{50}$ ± SD (μM) ROCK2 |
|---|---|---|---|
| 1cq | N-(4-(pyridin-4-yl)thiazol-2-yl)-3,4-dihydroisoquinoline-2(1H)-carboxamide | 3.87 ± 0.351 (n = 6) | 1.95 ± 0.389 (n = 6) |

TABLE 6-continued

SAR expansion of 1aa

| Compound | Structure | IC$_{50}$ ± SD (µM) ROCK1 | IC$_{50}$ ± SD (µM) ROCK2 |
| --- | --- | --- | --- |
| 12a | | 16.89 ± 2.11 (n = 6) | 8.35 ± 2.36 (n = 6) |
| 12b | | ROCK1 % inhibition @ 50 µM: 24.27 ± 4.08 | ND |
| 12c | | ROCK1 % inhibition @ 50 µM: 35.05 ± 0.11 | ND |
| 12d | | ROCK1 % inhibition @ 50 µM: 41.39 ± 1.85 | ND |
| 12e | | ROCK1 % inhibition @ 50 µM: 14.01 ± 0.02 | ND |
| 12f | | ROCK1 % inhibition @ 50 µM: −0.21 ± 2.41 | ND |

In summary, meta substitution appeared to be optimal for good activity. Small and polar groups are tolerated and hydroxy, methoxy, amino group give rise to better activity. Changes at the benzylic position of 1aa are tolerated resulting in significant potency in the case of methyl and methylhydroxy groups.

Figure 5:
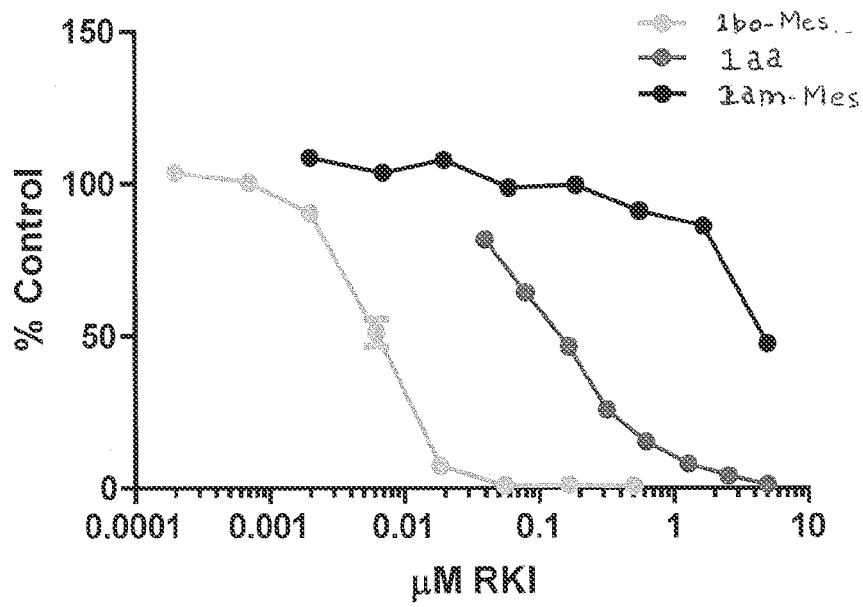
FIG. 5 shows the ROCK2 and ROCK1 inhibitory activity for 1bo-Mes, 1am-Mes, and 1aa.
Figure 5:
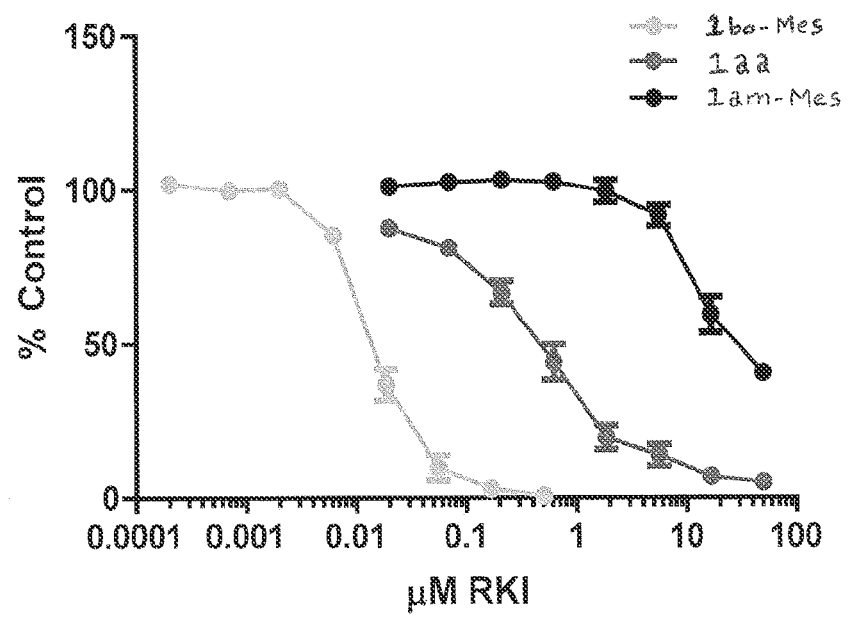

To achieve better compound solubility, the corresponding methanesulfonate salts of 1bo (1bo-mes) and 1am (1am-Mes) were prepared. The in vitro $IC_{50}$ values for 1bo-mes were 12 and 8 nM for ROCK 1 and 2, respectively (see FIG. 5). These values are very similar to those described immediately above for the corresponding 1bo in the free base form. The activities of the 2 forms of 1am were also similar (see FIG. 5 for 1am-Mes).

Figure 6:
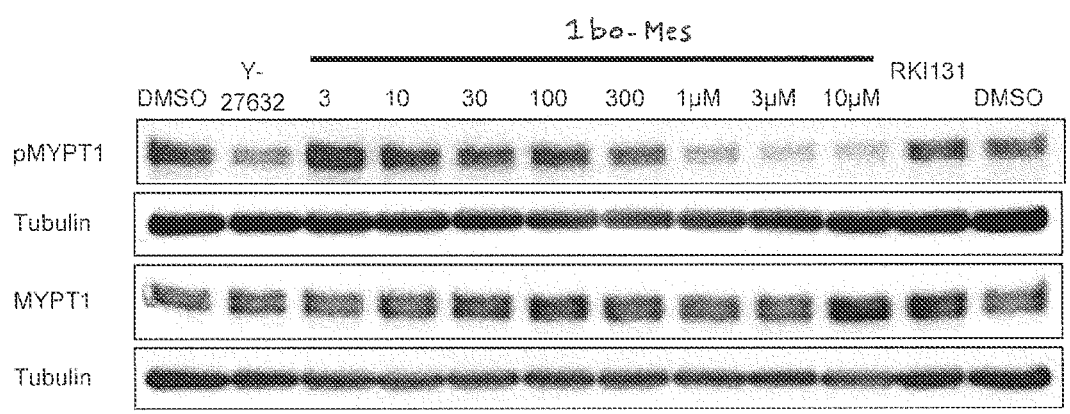
FIG. 6 shows 1bo-Mes inhibited the phosphorylation of MYPT1 in a concentration-dependent manner with an $IC_{50}$ value of 500 nM.

The ability of 1bo and the analog 1am were evaluated for their ability to inhibit ROCK in intact cells by determining their ability to decrease the phosphorylation levels of MYPT1, a substrate for ROCK kinase. To this end, the human lung cancer cell line H1299 was treated with either vehicle, a known ROCK inhibitor Y-27632 (10,000 nM), 1bo (0, 3, 10, 30, 100, 300, 1000, 3000 and 10,000 nM), or 1am at 10,000 nM, processed the cells for western blotting and immunoblotted with antibodies against P-MYPT1 and tubulin (loading control). FIG. 6 shows 1bo inhibited the phosphorylation of MYPT1 in a concentration-dependent manner with an $IC_{50}$ value 500 nM. In contrast, 1am at 10 μM did not affect the phosphorylation of MYPT1. Therefore, these studies are consistent with the in vitro studies of FIG. 5 and suggest that 1bo is able to enter cells and inhibit its intended target.

Figure 7:
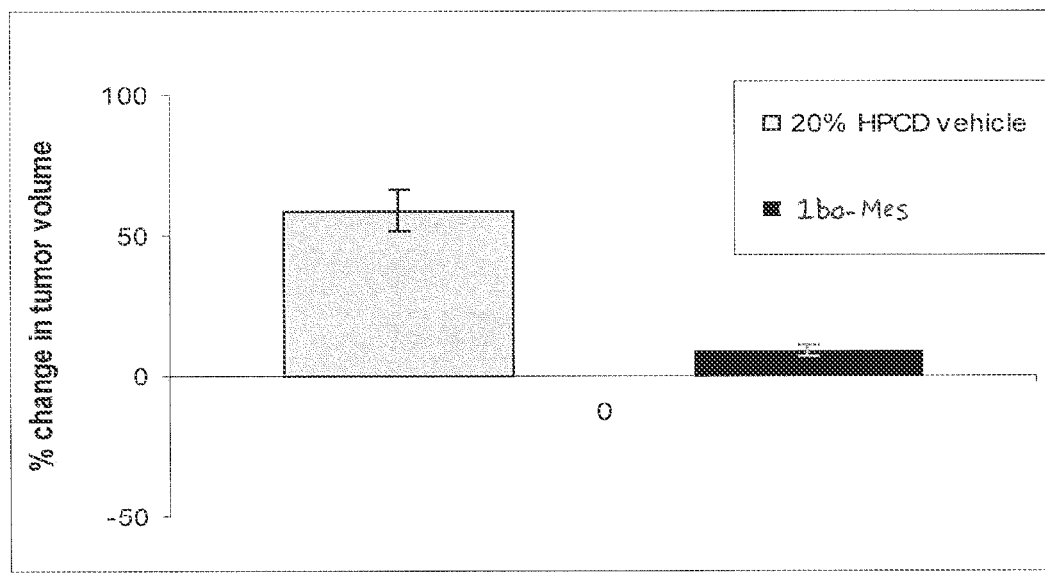
FIG. 7 shows the average percent change in tumor volume for 1bo-Mes in a mouse breast cancer model.

The anti tumor activity of 1bo was determined in vivo in a transgenic mouse breast cancer model. In this model, the mice harbor the rat Her2 gene under the control of the MMTV promoter. These mice therefore spontaneously develop tumors in their mammary tissues. Breast tumors were measured beginning at the time of tumor onset and treatment (once a day for 14 days) with vehicle (20% HPCD) or 1bo (200 mpk/day) began when tumor volumes reached about 200 to 2,300 mm³. A wide range of tumor volumes was used to ensure that responses were not volume dependent. FIG. 7 shows the average percent change for each treatment group. The percent change was calculated from the tumor volume on the last day of treatment relative to the volume on the day of initiation of treatment. Tumors from mice treated with vehicle increased in size with an average percent change in tumor volume of 58.8%+/−7.5% (FIG. 7). In contrast, tumors from mice treated with the 1bo increased in size with an average percent change in tumor volume of only 8.9%+/−1.7% %. Thus, on average the breast tumors from 1bo treated mice were 6.6 fold smaller compared to those tumors from mice treated with the vehicle control.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A compound having a chemical structure shown in Formula II

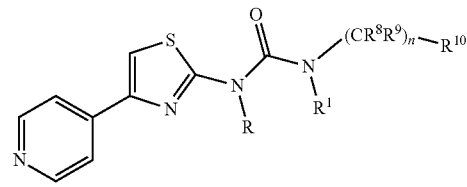

wherein
n is 1, 2, or 3;
R and $R^1$ are, independently of one another, H, alkyl, or acetyl;
$R^8$ and $R^9$ are, independently of one another, H, —OH, acetyl, —C(O)NH₂, alkyl or aryl, wherein the alkyl or aryl is optionally substituted with one or more of —OH, —NO₂, —NH₂, —NR⁶R⁷, carbonyl, alkoxy, alkyl, —OCX₃, —OCHX₂, —OCH₂X, or halogen, or both $R^8$ and $R^9$ together form a carbonyl;
$R^{10}$ is cycloalkyl or aryl, wherein the cycloalkyl or aryl is optionally substituted with one or more of —OH, —CO₂CH₃, —C(O)NH₂, —C(O)CH₃, —NO₂, —NH₂, —NR⁶R⁷, carbonyl, alkyl, alkoxy, alkylalkoxy, alkoxyalkoxy, cycloalkyl, aryl, —OCX₃, —OCHX₂, —OCH₂X, —OSO₂CH₃, -tosyl, or halogen;
$R^6$ and $R^7$ are, independently of one another, H, alkyl, —SO₂CH₃, —C(O)CH₃, or —C(O)NH₂;
X is independently H or halogen;
or a pharmaceutically acceptable salt thereof.

2. The compound of claim 1, wherein n is 1.

3. The compound of claim 1, wherein n is 2 or 3.

4. The compound of claim 1, $R^8$ and $R^9$ are, independently, H, alkyl, or alkyl substituted with —OH, —NH², alkoxy, or halogen.

5. The compound of claim 1, wherein n is 1, and $CR^8R^9$ is the R isomer of CHalkyl.

6. The compound of claim 1, wherein n is 1, and $CR^8R^9$ is the S isomer of CHalkyl, wherein the alkyl group is substituted with —OH, NH₂, alkoxy, or halogen.

7. The compound of claim 1, wherein $R^{10}$ is an aryl that is not substituted in the para position.

8. The compound of claim 1, wherein $R^{10}$ is an aryl which is optionally substituted in the meta-position with —OH, —CO₂CH₃, —C(O)NH₂, —NO₂, —NH₂, —NR⁶R⁷, alkoxy, alkylalkoxy, alkyl, —OSO₂CH₃, tosyl, or halogen.

9. The compound of claim 1, wherein n is 1 and $(CR^8R^9)R^{10}$ has the structure:

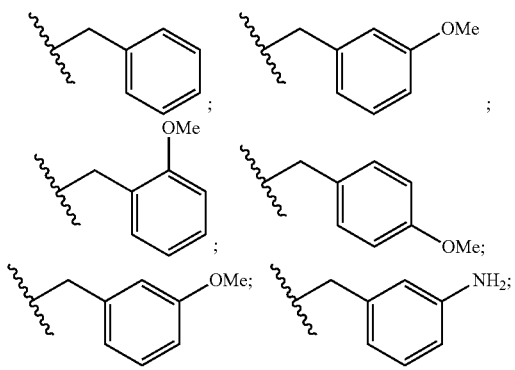

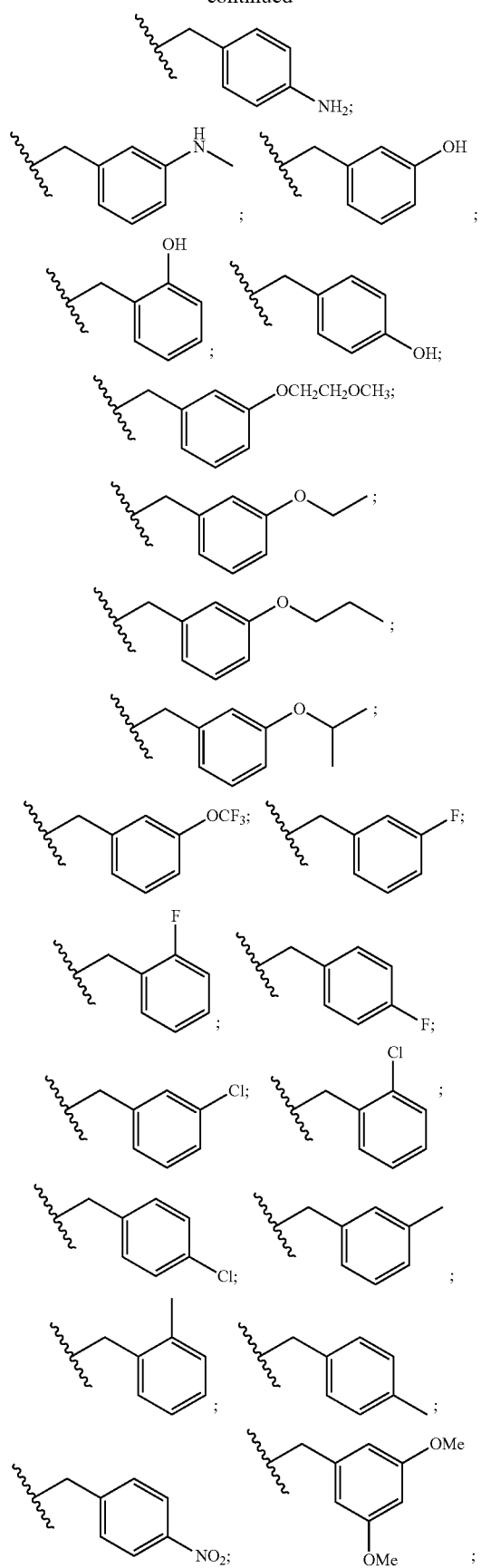
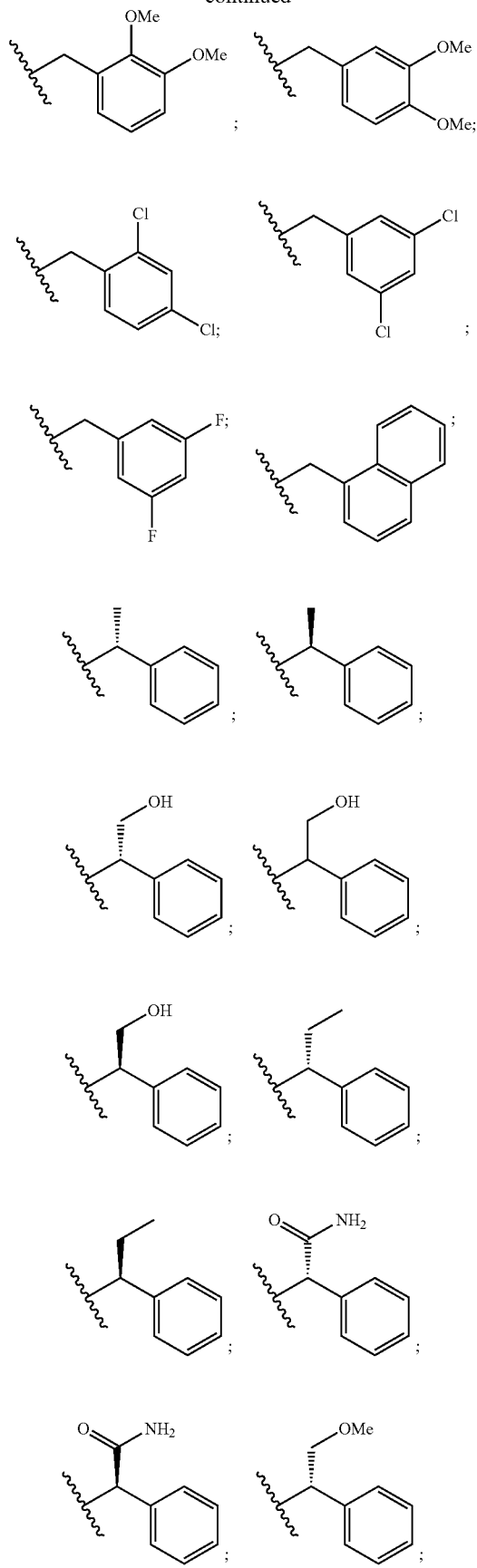

-continued
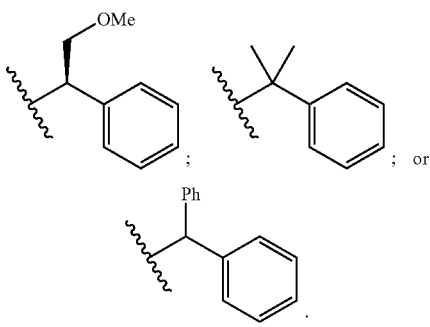
10. The compound of claim 1, wherein the compound has the formula:
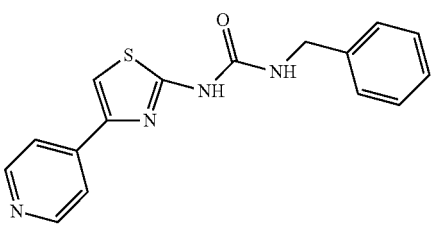 [SMILES: O=C(NCc1ccccc1)Nc1nc(-c2ccncc2)cs1]
or is a pharmaceutically acceptable salt thereof.
11. The compound of claim 1, wherein the compound has the formula:
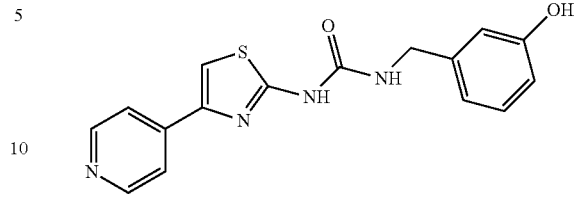
or is a pharmaceutically acceptable salt thereof.
12. The compound of claim 1, wherein the compound has the formula:
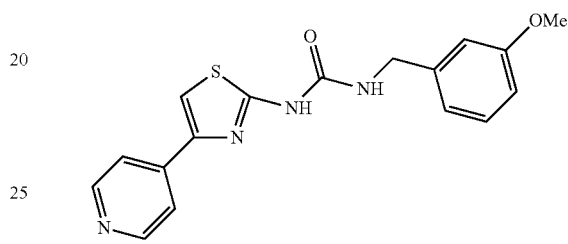
or is a pharmaceutically acceptable salt thereof.
* * * * *